US011875876B2

(12) United States Patent
Lu et al.

(10) Patent No.: US 11,875,876 B2
(45) Date of Patent: Jan. 16, 2024

(54) SYNTHETIC 5' UTR SEQUENCES, AND HIGH-THROUGHPUT ENGINEERING AND SCREENING THEREOF

(71) Applicant: Massachusetts Institute of Technology, Cambridge, MA (US)

(72) Inventors: Timothy Kuan-Ta Lu, Cambridge, MA (US); Manolis Kellis, Boston, MA (US); Jicong Cao, Cambridge, MA (US); Eva Maria Novoa Pardo, Cambridge, MA (US); Zhizhuo Zhang, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1251 days.

(21) Appl. No.: 16/441,647

(22) Filed: Jun. 14, 2019

(65) Prior Publication Data

US 2020/0066375 A1    Feb. 27, 2020

Related U.S. Application Data

(60) Provisional application No. 62/685,421, filed on Jun. 15, 2018.

(51) Int. Cl.
| | | |
|---|---|---|
| *C12N 15/11* | (2006.01) | |
| *G16B 20/50* | (2019.01) | |
| *G16B 40/00* | (2019.01) | |
| *C12N 15/10* | (2006.01) | |
| *C12N 15/85* | (2006.01) | |

(52) U.S. Cl.
CPC ......... *G16B 20/50* (2019.02); *C12N 15/1089* (2013.01); *C12N 15/11* (2013.01); *C12N 15/85* (2013.01); *G16B 40/00* (2019.02)

(58) Field of Classification Search
CPC ........ C12N 15/11; C12N 15/85; C12N 15/67; G16B 40/00
See application file for complete search history.

(56) References Cited

FOREIGN PATENT DOCUMENTS

| EP | 1176196 A1 | 1/2002 |
|---|---|---|
| WO | WO 89/00604 A1 | 1/1989 |
| WO | WO 01/55369 A1 | 8/2001 |
| WO | WO 01/55371 A1 | 8/2001 |
| WO | WO 2008/112127 A2 | 9/2008 |
| WO | WO 2009/042971 A2 | 4/2009 |
| WO | WO 2015/184466 A1 | 12/2015 |
| WO | WO 2017/127612 A1 | 7/2017 |

OTHER PUBLICATIONS

Dvir S et al. Proc Natl Acad Sci U S A. Jul. 23, 2013;110(30):E2792-801 (Year: 2013).*

Akhtar et al., Chromatin position effects assayed by thousands of reporters integrated in parallel. Cell. Aug. 15, 2013;154(4):914-27. doi: 10.1016/j.cell.2013.07.018.
Andreev et al., Translation of 5' leaders is pervasive in genes resistant to eIF2 repression. Elife. Jan. 26, 2015;4:e03971, 21 pages. doi:10.7554/eLife.03971.
Babendure et al., Control of mammalian translation by mRNA structure near caps. RNA. May 2006;12(5):851-61. doi:10.1261/rna.2309906.
Bai et al., Cytoplasmic transport and nuclear import of plasmid DNA. Biosci Rep. Nov. 29, 2017;37(6). pii: BSR20160616, 17 pages. doi: 10.1042/BSR20160616. Print Dec. 22, 2017.
Blundell et al., Structural biology and bioinformatics in drug design: opportunities and challenges for target identification and lead discovery. Philos Trans R Soc Lond B Biol Sci. Mar. 29, 2006;361(1467):413-23. doi: 10.1098/rstb.2005.1800. Epub Feb. 3, 2006.
Brown et al., Serine recombinases as tools for genome engineering. Methods. Apr. 2011;53(4):372-9. doi: 10.1016/j.ymeth.2010.12.031. Epub Dec. 30, 2010.
Chang et al., Lessons from Nature: microRNA-based shRNA libraries. Nat Methods. Sep. 2006;3(9):707-14.
Dronadula et al., Construction of a novel expression cassette for increasing transgene expression in vivo in endothelial cells of large blood vessels. Gene Ther. May 2011;18(5):501-8. doi: 10.1038/gt.2010.173. Epub Dec. 23, 2010.
Escors et al., Lentiviral vectors in gene therapy: Their current status and future potential. Arch Immunol Ther Exp (Warsz). Apr. 2010;58(2):107-19. doi: 10.1007/s00005-010-0063-4. Epub Feb. 9, 2010.
Ferraro et al., Clinical Applications of DNA Vaccines: Current Progress. Clin Infect Dis. Aug. 1, 2011;53(3):296-302. doi: 10.1093/cid/cir334.
Garmory et al., DNA vaccines: Improving expression of antigens. Genetic Vaccines and Therapy. Sep. 16, 2003;1(1):2, 5 pages. doi:10.1186/1479-0556-1-2.
Guye et al., Rapid, modular and reliable construction of complex mammalian gene circuits. Nucleic Acids Res. Sep. 2013;41(16):e156, 6 pages. doi: 10.1093/nar/gkt605. Epub Jul. 11, 2013.
Hacein-Bey-Abina et al., A Serious Adverse Event after Successful Gene Therapy for X-Linked Severe Combined Immunodeficiency. N Engl J Med. Jan. 16, 2003;348(3):255-6.
Hacein-Bey-Abina et al., Gene therapy of X-linked severe combined immunodeficiency. Int J Hematol. Nov. 2002;76(4):295-8. doi:10.1007/BF02982686.
Hanson et al., Tetracycline-aptamer-mediated translational regulation in yeast. Mol Microbiol. Aug. 11, 2003;49(6):1627-37. doi: 10.1046/j.1365-2958.2003.03656.x. Epub Sep. 2003.
Hardee et al., Advances in non-viral DNA vectors for gene therapy. Genes (Basel). Feb. 10, 2017;8(2). pii: E65, 22 pages. doi: 10.3390/genes8020065.

(Continued)

*Primary Examiner* — Neil P Hammell
*Assistant Examiner* — Douglas Charles Ryan
(74) *Attorney, Agent, or Firm* — Wolf, Greenfield & Sacks, P.C.

(57) ABSTRACT

Disclosed herein are novel 5' UTR sequences that can be used to control gene expression in various contexts. Also disclosed herein are methods of engineering 5' UTR sequences and methods and kits for screening 5' UTR sequences for a property of interest.

14 Claims, 22 Drawing Sheets

Specification includes a Sequence Listing.

(56) References Cited

OTHER PUBLICATIONS

Ho, The random subspace method for constructing decision forests. IEEE Trans Pattern Anal. Aug. 1998;20(8):832-44. doi: 10.1109/34.709601.

Hoelder et al., Discovery of small molecule cancer drugs: Successes, challenges and opportunities. Mol Oncol. Apr. 2012;6(2):155-76. doi: 10.1016/j.molonc.2012.02.004. Epub Mar. 3, 2012.

Hopkins et al., The druggable genome. Nat Rev Drug Discov. Sep. 2002;1(9):727-30. doi: 10.1038/nrd892.

Hsieh et al., The translational landscape of mTOR signalling steers cancer initiation and metastasis. Nature. Feb. 22, 2012;485(7396):55-61. doi: 10.1038/nature10912.

Imming et al., Drugs, their targets and the nature and number of drug targets. Nat Rev Drug Discov. Oct. 2006;5(10):821-34. doi:10.1038/nrd2132.

Jackson et al., The mechanism of eukaryotic translation initiation and principles of its regulation. Nat Rev Mol Cell Biol. Feb. 2010;11(2):113-27. doi: 10.1038/nrm2838.

Jones et al., Contemporary Approaches for Nonviral Gene Therapy. Discov Med. Jun. 2015;19(107):447-54.

Kozak, An analysis of 5'-noncoding sequences from 699 vertebrate messenger RNAs. Nucleic Acids Res. Oct. 26, 1987;15(20):8125-48. doi:10.1093/nar/15.20.8125. Ko.

Kozak, Downstream secondary structure facilitates recognition of initiator codons by eukaryotic ribosomes. PNAS. Nov. 1, 1990;87(21):8301-5. doi:10.1073/pnas.87.21.8301.

Kutzler et al., DNA vaccines: ready for prime time? Nat Rev Genet. Oct. 2008;9(10):776-88. doi: 10.1038/nrg2432.

Leader et al., Protein therapeutics: A summary and pharmacological classification. Nat Rev Drug Discov. Jan. 2008;7(1):21-39.

Lu et al., Non-viral gene delivery in skeletal muscle: a protein factory. Gene Ther. Jan. 2003;10(2):131-42.

Muthumani et al., Optimized and enhanced DNA plasmid vector based in vivo construction of a neutralizing anti-HIV-1 envelope glycoprotein Fab. Hum Vaccin Immunother. Oct. 2013;9(10):2253-62. doi: 10.4161/hv.26498. Epub Sep. 17, 2013.

Naldini, Gene therapy returns to centre stage. Nature. Oct. 15, 2015;526(7573):351-60. doi:10.1038/nature15818.

Overington et al., How many drug targets are there? Nat Rev Drug Discov. Dec. 2006;5(12):993-6.

Perez-Pinera et al., Synthetic biology and microbioreactor platforms for programmable production of biologics at the point-of-care. Nat Commun. Jul. 29, 2016;7:12211, 1-10 pages. doi:10.1038/ncomms12211.

Powell et al., Viral expression cassette elements to enhance transgene target specificity and expression in gene therapy. Discov Med. Jan. 2015;19(102):49-57.

Qin et al., Systematic Comparison of Constitutive Promoters and the Doxycycline-Inducible Promoter. Plos One. May 12, 2010;5(5):e10611, 4 pages. doi:ARTN e1061110.1371/journal.pone.0010611.

Ramamoorth et al., Non viral vectors in gene therapy—An overview. J Clin Diagn Res. Jan. 2015;9(1):GE01-6. doi:10.7860/JCDR/2015/10443.5394.

Reichert et al., Monoclonal antibody successes in the clinic. Nat Biotechnol. Sep. 2005;23(9):1073-8. doi: 10.1038/nbt0905-1073.

Rodrigues et al., Pharmaceutical Development of AAV-Based Gene Therapy Products for the Eye. Pharm Res. Dec. 27, 2018;36(2):29, 20 pages. doi: 10.1007/s11095-018-2554-7.

Roquet et al., Synthetic recombinase-based State machines in living cells. Science. Jul. 22, 2016;353(6297):aad8559, 15 pages. doi: 10.1126/science.aad8559. Epub Jul. 21, 2016.

Sahin, mRNA-based therapeutics—developing a new class of drugs. Nat Rev Drug Discov. Oct. 2014;13(10):759-80. doi: 10.1038/nrd4278. Epub Sep. 19, 2014.

Schmeer et al., Plasmid DNA Manufacturing for Indirect and Direct Clinical Applications. Hum Gene Ther. Oct. 2017;28(10):856-861. doi: 10.1089/hum.2017.159. Epub Aug. 21, 2017.

Scott et al., Small molecules, big targets: drug discovery faces the protein-protein interaction challenge. Nat Rev Drug Discov. Aug. 2016;15(8):1-59. doi: 10.1038/nrd.2016.29. Epub Apr. 11, 2016.

Scrucca, GA : A Package for Genetic Algorithms in R. J Stat Softw. Apr. 2013;53(4). 37 pages. doi:10.18637/jss.v053.i04.

Shalem et al., Genome-scale CRISPR-Cas9 knockout screening in human cells. Science. Jan. 3, 2014;343(6166):84-7. doi: 10.1126/science.1247005. Epub Dec. 12, 2013.

Shim et al., Nonviral Delivery Systems For Cancer Gene Therapy: Strategies And Challenges. Curr Gene Ther. 2018;18(1):3-20. doi: 10.2174/1566523218666180119121949.

Sudrik et al., Translational repression using BIV Tat peptide-TAR RNA interaction in mammalian cells. Chem Commun (Camb). Aug. 28, 2013;49(67):7457-9. doi: 10.1039/c3cc43086c.

Verdine et al., Stapled Peptides for Intracellular Drug Targets. Methods Enzymol. 2012;503:3-33. doi: 10.1016/B978-0-12-396962-0.00001-X.

Wein et al., Translation from a DMD exon 5 IRES results in a functional dystrophin isoform that attenuates dystrophinopathy in humans and mice. Nat Med. Sep. 2014;20(9):992-1000. doi: 10.1038/nm.3628. Epub Aug. 10, 2014.

Weinberger et al., Deciphering the rules by which 5'-UTR sequences affect protein expression in yeast. PNAS USA. Jul. 23, 2013;110(30):E2792-801. doi: 10.1073/pnas.1222534110. Epub Jul. 5, 2013.

Wilson et al., Position effects on eukaryotic gene expression. Annu Rev Cell Biol. 1990;6:679-714. doi:10.1146/annurev.cb.06.110190.003335.

Wong et al., Massively parallel high-order combinatorial genetics in human cells. Nat Biotechnol. Sep. 2015;33(9):952-61. doi: 10.1038/nbt.3326. Epub Aug. 17, 2015.

Yin et al., Non-viral vectors for gene-based therapy. Nat Rev Genet. Aug. 2014;15(8):541-55. doi: 10.1038/nrg3763. Epub Jul. 15, 2014.

Invitation to Pay Additional Fees mailed Sep. 6, 2019, for Application No. PCT/US2019/037269.

Asrani et al., Optimization of mRNA untranslated regions for improved expression of therapeutic mRNA. RNA Biol. 2018; 15(6):756-62. doi: 10.1080/15476286.2018.1450054. Epub Mar. 26, 2018.

Cuperus et al., Deep learning of the regulatory grammar of yeast 5' untranslated regions from 500,000 random sequences. Genome Res. Dec. 2017;27(12):2015-24. doi: 10.1101/gr.224964.117. Epub Nov. 2, 2017.

Davuluri et al., CART classification of human 5'UTR sequences. Genome Res. Nov. 2000;10(11):1807-16.

Decoene et al., Toward predictable 5'UTRs in *Saccharomyces cerevisiae*: development of a yUTR calculator. ACS Synth Biol. Feb. 16, 2018;7(2):622-634. doi: 10.1021/acssynbio.7b00366. Epub Feb. 5, 2018.

Ding et al., Engineering the 5' UTR-mediated regulation of protein abundance in yeast using nucleotide sequence activity relationships. ACS Synth Biol. Dec. 21, 2018;7(12):2709-2714. doi: 10.1021/acssynbio.8b00127. Epub Dec. 13, 2018.

Dvir et al., Deciphering the rules by which 5'-UTR sequences affect protein expression in yeast. Proc Natl Acad Sci USA. Jul. 23, 2013;110(30):E2792-801. doi: 10.1073/pnas.1222534110. Epub Jul. 5, 2013.

Jin et al., Rapid evolution of regulatory element libraries for tunable transcriptional and translational control of gene expression. Synth Syst Biotechnol. Oct. 19, 2017;2(4):295-301. doi: 10.1016/j.synbio.2017.10.003. eCollection Dec. 2017.

Kamura et al., Selection of 5'-untranslated sequences that enhance initial of translation in a cell-free protein synthesis system from wheat embryos. Bioorg Med Chem Lett. Dec. 15, 2005;15(24):5402-6. Epub Oct. 5, 2005.

Leppek et al., Functional 5'UTR mRNA structures in eukaryotic translation regulation and how to find them. Nature. Mar. 2018;19(3):158-74. doi: 10.1038/nrm.2017.103. Epub Nov. 22, 2017.

Mie et al., Selection of mRNA 5'-untranslatioed region sequences with high translation efficiency through ribosome display. Biochem Biophys Res Commun. Aug. 15, 2008;373(1):48-52. doi: 10.1016/j.bbrc.2008.05.173. Epub Jun. 9, 2008.

(56) References Cited

OTHER PUBLICATIONS

Sample et al., Human 5'UTR design and variant effect prediction from a massively parallel translation assay. bioRXiv. First posted online Apr. 29, 2018:1-10. doi: 10.1101/310375.

Sample et al., Human 5'UTR design and variant effect prediction from a massively parallel translation assay. Nat Biotechnol. Jul. 2019;37(7):803-9. doi: 10.1038/s41587-019-0164-5. Epub Jul. 1, 2019.

Specht et al., Synthetic oligonucleotide libraries reveal novel regulatory elements in chlamydomonas chloroplast mRNAs. ACS Synth Biol. Jan. 18, 2013;2(1):34-46. Epub Oct. 31, 2012.

Trinklein et al., Identification and functional analysis of human transcriptional promoters. Genome Res. Feb. 2003;13(2):308-12.

* cited by examiner

SEQUENCE LISTING

<160> NUMBER OF SEQ ID NOS: 13

<210> SEQ ID NO 1
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 1

```
cactcgcgct gccatcactc ttccgccgtc ttcgccgcca tcctcggcgc gactcgcttc      60
tttcggttct accaggtaga gtccgccgcc atcctccacc                           100
```

<210> SEQ ID NO 2
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 2

```
cattctgtgg tctgatcatc ctgtggtttc gtcgccgcca tcctcgtcgc gacacgctgt      60
tttcggttct cggcccgacg agccatcgcc atcctacagc                           100
```

<210> SEQ ID NO 3
<211> LENGTH: 100
<212> TYPE: DNA
<213> ORGANISM: Artificial Sequence
<220> FEATURE:
<223> OTHER INFORMATION: Synthetic polynucleotide

<400> SEQUENCE: 3

```
cttgtctcgc tccggggaac gctcggaaac tccggccgc cgccacccgc gtctgttctg      60
ttacacaagg gaagaaaagc cgctgccgca ctccgagtgt                           100
```

<210> SEQ ID NO 4
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 4

```
taaacttaag cttggtaccg                                                  20
```

<210> SEQ ID NO 5
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 5

```
gccaccatgg tgagcaaggg                                                  20
```

<210> SEQ ID NO 6
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 6

```
aacttaagct tggtaccg                                                    18
```

<210> SEQ ID NO 7
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 7
ctcgcccttg ctcaccatgg tggc                                            24

<210> SEQ ID NO 8
<211> LENGTH: 206
<212> TYPE: DNA
<213> ORGANISM: Artificial Sequence
<220> FEATURE:
<223> OTHER INFORMATION: Synthetic polynucleotide

<400> SEQUENCE: 8
cactcgcgct gccatcactc ttccgccgtc ttcgccgcca tcctcggcgc gactcgcttc      60
tttcggttct accaggtaga gtccgccgcc atcctccacc caacaacttg tctcgctccg     120
gggaacgctc ggaaactccc ggccgccgcc acccgcgtct gttctgttac acaagggaag    180
aaaagccgct gccgcactcc gagtgt                                          206

<210> SEQ ID NO 9
<211> LENGTH: 206
<212> TYPE: DNA
<213> ORGANISM: Artificial Sequence
<220> FEATURE:
<223> OTHER INFORMATION: Synthetic polynucleotide

<400> SEQUENCE: 9
cattctgtgg tctgatcatc ctgtggtttc gtcgccgcca tcctcgtcgc gacacgctgt      60
tttcggttct cggcccgacg agccatcgcc atcctacagc caacaacttg tctcgctccg     120
gggaacgctc ggaaactccc ggccgccgcc acccgcgtct gttctgttac acaagggaag    180
aaaagccgct gccgcactcc gagtgt                                          206

<210> SEQ ID NO 10
<211> LENGTH: 206
<212> TYPE: DNA
<213> ORGANISM: Artificial Sequence
<220> FEATURE:
<223> OTHER INFORMATION: Synthetic polynucleotide

<400> SEQUENCE: 10
cttgtctcgc tccggggaac gctcggaaac tcccggccgc cgccacccgc gtctgttctg      60
ttacacaagg gaagaaaagc cgctgccgca ctccgagtgt caacaacact cgcgctgcca     120
tcactcttcc gccgtcttcg ccgccatcct cggcgcgact cgcttctttc ggttctacca    180
ggtagagtcc gccgccatcc tccacc                                          206

<210> SEQ ID NO 11
<211> LENGTH: 206
<212> TYPE: DNA
<213> ORGANISM: Artificial Sequence
<220> FEATURE:
<223> OTHER INFORMATION: Synthetic polynucleotide

<400> SEQUENCE: 11
cattctgtgg tctgatcatc ctgtggtttc gtcgccgcca tcctcgtcgc gacacgctgt      60

```
tttcggttct cggcccgacg agccatcgcc atcctacagc caacaacact cgcgctgcca    120
tcactcttcc gccgtcttcg ccgccatcct cggcgcgact cgcttctttc ggttctacca    180
ggtagagtcc gccgccatcc tccacc                                         206

<210> SEQ ID NO 12
<211> LENGTH: 206
<212> TYPE: DNA
<213> ORGANISM: Artificial Sequence
<220> FEATURE:
<223> OTHER INFORMATION: Synthetic polynucleotide

<400> SEQUENCE: 12
cttgtctcgc tccggggaac gctcggaaac tcccggccgc cgccacccgc gtctgttctg     60
ttacacaagg gaagaaaagc cgctgccgca ctccgagtgt caacaacatt ctgtggtctg    120
atcatcctgt ggtttcgtcg ccgccatcct cgtcgcgaca cgctgttttc ggttctcggc    180
ccgacgagcc atcgccatcc tacagc                                         206

<210> SEQ ID NO 13
<211> LENGTH: 206
<212> TYPE: DNA
<213> ORGANISM: Artificial Sequence
<220> FEATURE:
<223> OTHER INFORMATION: Synthetic polynucleotide

<400> SEQUENCE: 13
cactcgcgct gccatcactc ttccgccgtc ttcgccgcca tcctcggcgc gactcgcttc     60
tttcggttct accaggtaga gtccgccgcc atcctccacc caacaacatt ctgtggtctg    120
atcatcctgt ggtttcgtcg ccgccatcct cgtcgcgaca cgctgttttc ggttctcggc    180
ccgacgagcc atcgccatcc tacagc                                         206
```

SYNTHETIC 5' UTR SEQUENCES, AND HIGH-THROUGHPUT ENGINEERING AND SCREENING THEREOF

RELATED APPLICATION

This application claims priority under 35 U.S.C. § 119(e) to U.S. provisional patent application No. 62/685,421, filed Jun. 15, 2018, the entire contents of which are incorporated herein by reference.

GOVERNMENT SUPPORT

This invention was made with Government support under Grant No. W911NF-11-2-0056 awarded by the Army Research Office (ARO), and Grant Nos. R01 GM113708 and R01 HG004037 awarded by the National Institutes of Health (NIH). The Government has certain rights in the invention.

FIELD

Disclosed herein are novel 5' UTR sequences that can be used to control gene expression in various contexts. Also disclosed herein are methods of engineering 5' UTR sequences and methods and kits for screening 5' UTR sequences for a property of interest.

BACKGROUND

Although in vivo DNA delivery efficiency has been improved significantly as a result of the recent advancements in liposome chemistry and nanoparticles, only a small number of DNA plasmids can enter the nucleus (12-14). To ensure that drug levels produced in vivo are sufficient, either DNA doses can be increased or transfections can be done repeatedly. Either of these approaches, however, increases costs and time of production. Alternatively, protein expression can be enhanced by optimizing the backbone of the DNA vector, such as in the 5' untranslated region (5' UTR) sequences. However, the rational design of 5' UTR sequences to enhance protein expression has remained elusive, even though 5' UTR sequences have been identified that regulate gene expression in certain scenarios (20-24). The design of 5' UTR sequences has been held back by limited knowledge of the relationships between the 5' UTR sequences and protein expression levels.

SUMMARY

Non-viral gene delivery depends on achieving high enough levels of protein expression to have a desired therapeutic effect. Engineering 5' untranslated region (UTR) sequences that enhance protein expression is a great challenge in the study of gene expression because our knowledge of how 5' UTR sequences modulate protein abundance is limited.

Disclosed herein is a comprehensive high-throughput strategy to design, screen, and optimize novel 5' UTR sequences, which can then be used to fine tune protein expression. To eliminate the copy number and position effects in traditional lentiviral screening, a recombinase-mediated library screening strategy was developed. Through this strategy, various synthetic 5' UTR sequences were identified that permit high heterogeneous gene expression in a variety of cell lines. Pairing these 5' UTR sequences enabled higher protein expression than obtained with each 5' UTR individually.

Accordingly, in some aspects, the disclosure relates to synthetic 5' untranslated region (5' UTR) sequences. In some embodiments, the 5' UTR sequences comprises the polynucleotide sequence of:

(SEQ ID NO: 1)
CACTCGCGCTGCCATCACTCTTCCGCCGTCTTCGCCGCCATCCTCGGCG

CGACTCGCTTCTTTCGGTTCTACCAGGTAGAGTCCGCCGCCATCCTCCA

CC;

(SEQ ID NO: 2)
CATTCTGTGGTCTGATCATCCTGTGGTTTCGTCGCCGCCATCCTCGTCG

CGACACGCTGTTTTCGGTTCTCGGCCCGACGAGCCATCGCCATCCTACA

GC;
or (SEQ ID NO: 3)
CTTGTCTCGCTCCGGGGAACGCTCGGAAACTCCCGGCCGCCGCCACCCG

CGTCTGTTCTGTTACACAAGGGAAGAAAAGCCGCTGCCGCACTCCGAGT

GT.

In other aspects, the disclosure relates to polynucleotides comprising SEQ ID NO: 1, SEQ ID NO: 2, or SEQ ID NO: 3. In some embodiments, wherein the polynucleotide comprises two or more 5' UTR sequences, at least two of the 5' UTR sequences are separated by a linker sequence. In some embodiments, at least two of the 5' UTR sequences have different polynucleotide sequences.

In some embodiments, the polynucleotide comprises the polynucleotide sequence of:

(SEQ ID NO: 8)
CACTCGCGCTGCCATCACTCTTCCGCCGTCTTCGCCGCCATCCTCGGCGC

GACTCGCTTCTTTCGGTTCTACCAGGTAGAGTCCGCCGCCATCCTCCACC

CAACAACTTGTCTCGCTCCGGGGAACGCTCGGAAACTCCCGGCCGCCGCC

ACCCGCGTCTGTTCTGTTACACAAGGGAAGAAAAGCCGCTGCCGCACTCC

GAGTGT;

(SEQ ID NO: 9)
CATTCTGTGGTCTGATCATCCTGTGGTTTCGTCGCCGCCATCCTCGTCGC

GACACGCTGTTTTCGGTTCTCGGCCCGACGAGCCATCGCCATCCTACAGC

CAACAACTTGTCTCGCTCCGGGGAACGCTCGGAAACTCCCGGCCGCCGCC

ACCCGCGTCTGTTCTGTTACACAAGGGAAGAAAAGCCGCTGCCGCACTCC

GAGTGT;

(SEQ ID NO: 10)
CTTGTCTCGCTCCGGGGAACGCTCGGAAACTCCCGGCCGCCGCCACCCGC

GTCTGTTCTGTTACACAAGGGAAGAAAAGCCGCTGCCGCACTCCGAGTGT

CAACAACACTCGCGCTGCCATCACTCTTCCGCCGTCTTCGCCGCCATCCT

CGGCGCGACTCGCTTCTTTCGGTTCTACCAGGTAGAGTCCGCCGCCATCC

TCCACC;

-continued (SEQ ID NO: 11)
CATTCTGTGGTCTGATCATCCTGTGGTTTCGTCGCCGCCATCCTCGTCGC

GACACGCTGTTTTCGGTTCTCGGCCCGACGAGCCATCGCCATCCTACAGC

CAACAACACTCGCGCTGCCATCACTCTTCCGCCGTCTTCGCCGCCATCCT

CGGCGCGACTCGCTTCTTTCGGTTCTACCAGGTAGAGTCCGCCGCCATCC

TCCACC;

(SEQ ID NO: 12)
CTTGTCTCGCTCCGGGGAACGCTCGGAAACTCCCGGCCGCCGCCACCCGC

GTCTGTTCTGTTACACAAGGGAAGAAAAGCCGCTGCCGCACTCCGAGTGT

CAACAACATTCTGTGGTCTGATCATCCTGTGGTTTCGTCGCCGCCATCCT

CGTCGCGACACGCTGTTTTCGGTTCTCGGCCCGACGAGCCATCGCCATCC

TACAGC;
or (SEQ ID NO: 13)
CACTCGCGCTGCCATCACTCTTCCGCCGTCTTCGCCGCCATCCTCGGCGC

GACTCGCTTCTTTCGGTTCTACCAGGTAGAGTCCGCCGCCATCCTCCACC

CAACAACATTCTGTGGTCTGATCATCCTGTGGTTTCGTCGCCGCCATCCT

CGTCGCGACACGCTGTTTTCGGTTCTCGGCCCGACGAGCCATCGCCATCC

TACAGC.

In some embodiments, the polynucleotide further comprises a promoter, wherein the promoter is positioned 5' to at least one of the 5' UTR sequences.

In some embodiments, the polynucleotide further comprises a polynucleotide sequence encoding a product of interest, wherein the one or more 5' UTR sequences are operably linked to the polynucleotide sequence encoding the product of interest.

In some aspects, the disclosure relates to compositions comprising a polynucleotide, wherein the polynucleotide comprises SEQ ID NO: 1, SEQ ID NO: 2, and/or SEQ ID NO: 3.

In other aspects, the disclosure relates to methods of expressing a product of interest in a cell. In some embodiments, the method comprises contacting the cell encoding a product of interest, thereby introducing the polynucleotide comprising the polynucleotide sequence encoding the product of interest into the cell, wherein the polynucleotide comprises SEQ ID NO: 1, SEQ ID NO: 2, and/or SEQ ID NO: 3. In some embodiments, the cell is contacted in vitro. In other embodiments, the cell is contacted in vivo.

In yet other aspects, the disclosure relates to methods of generating a population of nucleic acid molecules each comprising a 5' untranslated region (5' UTR) sequence. In some embodiments the method comprises: (a) providing an initial population of nucleic acid molecules each comprising a 5' UTR sequence; (b) calculating a fitness score for each of the 5' UTR sequences in the initial population of polynucleic acid molecules, wherein the fitness score reflects expression level or translation efficiency of a mRNA comprising the 5' UTR sequence; (c) selecting a subset of nucleic acid molecules from the initial population, wherein the subset consists of: (i) the 25 percent of nucleic acid molecules comprising a 5' UTR sequence having the highest fitness score in (b); the 25 percent of nucleic acid molecules comprising a 5' UTR sequence having the lowest fitness score in (b); or a combination thereof; thereby generating a population of nucleic acid molecules each comprising a 5' UTR sequence.

In some embodiments, the initial population in (a) comprises nucleic acid molecules each comprising an endogenous 5' UTR sequence, wherein the endogenous 5' UTR sequences are found in mRNAs expressed in a cell or population of cells. In some embodiments, the cells of the population are the same type of cell. In other embodiments, the population of cells comprises different cell types.

In some embodiments, calculating the fitness scores for the endogenous 5' UTR sequences in (b) comprises: (i) measuring the abundances of a least a subset of the mRNAs in a cell or population of cells, wherein the subset of mRNAs collectively comprise the endogenous 5' UTR sequences; (ii) ranking the mRNAs of (i) according to their expression levels in the cell or population of cells; and (iii) assigning a fitness score to the endogenous 5' UTR sequences according to the ranking of the mRNAs in (ii). In some embodiments, the abundances of the mRNAs are measured in (i) by RT-PCR, real time PCR, or RNA-Seq. In some embodiments, the abundances of the mRNAs are measured by RNA-Seq and the mRNAs are ranked according RPKM, where RPKM represents Reads Per Kilobase of transcript per Million mapped reads.

In some embodiments, the calculating the fitness scores for the endogenous 5' UTR sequences in (b) comprises: (i) measuring the translation efficiencies of a least a subset of the mRNAs in a cell or population of cells, wherein the subset of mRNAs collectively comprise the endogenous 5' UTR sequences; (ii) ranking the mRNAs of (i) according to their translation efficiencies in the cell or population of cells; and (iii) assigning a fitness score to the endogenous 5' UTR sequences according to the ranking of the mRNAs in (ii). In some embodiments, the translation efficiencies of the mRNAs are measured in (i) by Ribo-Seq. In some embodiments, the mRNAs are ranked in (ii) according to RPKM, where RPKM represents Reads Per Kilobase of transcript per Million mapped reads.

In some embodiments, the calculating the fitness score for the endogenous 5' UTR sequences in (b) comprises: (i) measuring the abundances and translation efficiencies of a least a subset of the mRNAs in a cell or population of cells, wherein the subset of mRNAs collectively comprise the endogenous 5' UTR sequences; (ii) ranking the mRNAs of (i) according to their protein expression, wherein protein expression is computed as: mRNA abundance*mRNA translation efficiency; and (iii) assigning a fitness score to the endogenous 5' UTR sequences according to the ranking of the mRNAs in (ii). In some embodiments, the abundances of the mRNAs are measured by RNA-Seq; the translation efficiencies of the mRNAs are measured by Ribo-Seq; or a combination thereof.

In some embodiments, the method further comprises: (d) synthesizing the subset of nucleic acid molecules selected in (c); thereby generating a population of nucleic acid molecules each comprising a 5' UTR sequence.

In some embodiments, the method comprises: (a) providing an initial population of nucleic acid molecules each comprising a 5' UTR sequence; (b) extracting sequence features from the 5' UTR sequences of the initial population of polynucleic acid molecules (a); (c) calculating a fitness score for each of the 5' UTR sequences in the initial population of polynucleic acid molecules of (a), wherein the fitness score reflects expression level or translation efficiency of a mRNA comprising the 5' UTR sequence and, accordingly, one or more of the sequence features of (b); (d) training a machine learning model to learn a function that maps the sequence features of (b) with the fitness score of the 5' UTR comprising the feature in (c); and (e) deriving a set of synthetic 5' UTR sequences from a second population of nucleic acid molecules each comprising a 5' UTR sequence, wherein the synthetic 5' UTR sequences have a higher predicted fitness score than the 5' UTR sequences from which they are derived, wherein the predicted fitness score is calculated according to the function of (d); thereby generating a population of nucleic acid molecules each comprising a 5' UTR sequence.

In some embodiments, the initial population in (a) comprises nucleic acid molecules each comprising an endogenous 5' UTR sequence, wherein the endogenous 5' UTR sequences are found in mRNAs expressed in a cell or population of cells. In some embodiments, the cells of the population are the same type of cell. In other embodiments, the population of cells comprises different cell types.

In some embodiments, the calculating the fitness scores for the endogenous 5' UTR sequences in (c) comprises: (i) measuring the abundances of a least a subset of the mRNAs in a cell or population of cells, wherein the subset of mRNAs collectively comprise the endogenous 5' UTR sequences; (ii) ranking the mRNAs of (i) according to their expression levels in the cell or population of cells; and (iii) assigning a fitness score to the endogenous 5' UTR sequences according to the ranking of the mRNAs in (ii). In some embodiments, the abundances of the mRNAs are measured in (i) by RT-PCR, real time PCR, or RNA-Seq. In some embodiments the abundances of the mRNAs are measured by RNA-Seq, and the mRNAs are ranked according RPKM, where RPKM represents Reads Per Kilobase of transcript per Million mapped reads.

In some embodiments, the calculating the fitness scores for the endogenous 5' UTR sequences in (c) comprises: (i) measuring the translation efficiencies of a least a subset of the mRNAs in a cell or population of cells, wherein the subset of mRNAs collectively comprise the endogenous 5' UTR sequences; (ii) ranking the mRNAs of (i) according to their translation efficiencies in the cell or population of cells; and (iii) assigning a fitness score to the endogenous 5' UTR sequences according to the ranking of the mRNAs in (ii). In some embodiments, the translation efficiencies of the mRNAs are measured in (i) by Ribo-seq. In some embodiments, the mRNAs are ranked in (ii) according to RPKM, where RPKM represents Reads Per Kilobase of transcript per Million mapped reads.

In some embodiments, the calculating the fitness score for the endogenous 5' UTR sequences in (c) comprises: (i) measuring the abundances and translation efficiencies of a least a subset of the mRNAs in a cell or population of cells, wherein the subset of mRNAs collectively comprise the endogenous 5' UTR sequences; (ii) ranking the mRNAs of (i) according to their protein expression, wherein protein expression is computed as: mRNA abundance*mRNA translation efficiency; and (iii) assigning a fitness score to the endogenous 5' UTR sequences according to the ranking of the mRNAs in (ii). In some embodiments, the abundances of the mRNAs are measured by RNA-seq; the translation efficiencies of the mRNAs are measured by Ribo-seq; or a combination thereof.

In some embodiments, the second population of nucleic acid molecules each comprising a 5' UTR sequence in (e) comprises a subset of the initial population of nucleic acid molecules in (a).

In some embodiments, (e) comprises: (i) selecting a population of 5' UTR sequences; (ii) calculating fitness scores for the 5' UTR sequences of the population of (i) according to the function of (d); (iii) introducing mutations in the 5' UTR sequences of the population of (i), thereby generating a population of mutated 5' UTR sequences; (iv) calculating fitness scores for the 5' UTR sequences of the population of mutated 5' UTR sequences according to the function of (d); (v) selecting a subset of 5' UTR sequences from the population of mutated 5' UTR sequences, wherein the subset consists of: 5' UTR sequences having a higher predicted fitness score than the 5' UTR sequences from which they are derived, wherein the predicted fitness score is calculated according to the function of (d). In some embodiments, (i)-(v) are repeated one or more times. In some embodiments, the mutations are introduced in (iii) using a genetic algorithm.

In some embodiments, the sequence features in (b) comprise k-mer frequency, codon usage, RNA folding energy, 5' UTR length, and number of ORFs.

In some embodiments, the method further comprises: (f) synthesizing a population of nucleic acid molecules each comprising a derived synthetic 5' UTR sequence of (e); thereby generating a population of nucleic acid molecules each comprising a 5' UTR sequence.

In some aspects, the disclosure relates to populations of nucleic acid molecules generated according to the methods described herein.

In other aspects, the disclosure relates to methods of screening a library of 5' untranslated region (5' UTR) sequences for a characteristic of interest. In some embodiments, the method comprises: (a) providing a population of donor polynucleotides collectively comprising a library of 5' UTR sequences, optionally wherein the library of 5' UTR sequences comprises the polynucleic acid molecules of claim 43, wherein each donor polynucleotide comprises: (i) a donor cassette comprising a polynucleotide sequence comprising a promoter, a 5' UTR sequence from the library of 5' UTR sequences, and a polynucleotide sequence encoding an output protein; and (ii) a recombinase attachment site; (b) contacting the population of donor polynucleotides of (a) with a population of acceptor cells, wherein each of the acceptor cells comprises a landing pad localized at a common genetic location, wherein the landing pad comprises a recombinase attachment site that is compatible with the recombinase attachment site of a donor polynucleotide; (c) expressing a recombinase in the acceptors cells to induce recombination between the donor polynucleotides of (a) and the acceptor cells of (b), thereby generating a population of recombined cells, wherein each of the recombined cells comprises the donor cassette of a donor polynucleotide; and (d)identifying the 5' UTR sequences having the characteristic of interest according to the level of output protein in the recombined cells.

In some embodiments, the characteristic of interest is a high translation efficiency. In other embodiments, the characteristic of interest is a low translation efficiency.

In some embodiments, the promoter of the donor cassette is a CMV promoter.

In some embodiments, the output protein is a fluorescent protein.

In some embodiments, the recombinase sites of the donor polynucleotides are attB recombinase sites and the recombinase sites of the landing pads of the acceptor cells are attP recombinase sites.

In some embodiments, the recombinase is Bxb1.

In some embodiments, the donor cassette of the donor polynucleotides of (a) further comprise a polynucleotide sequence encoding a selectable marker. In some embodiments, the selectable marker comprises an antibiotic resistance gene. In some embodiments, the selectable marker comprises a fluorescent protein.

In some embodiments, the recombination between the donor polynucleotide and the acceptor cell destroys the recombinase attachment site of the landing pad of the acceptor cell, thereby prohibiting further recombination at the landing pad.

In some aspects, the disclosure relates to kits for performing the methods described herein. In some embodiments, a kit comprises a population of acceptor cells, wherein each of the acceptor cells comprises a landing pad localized at a common genetic location, wherein the landing pad comprises a recombinase attachment site. In some embodiments, the kit further comprises a polynucleotide sequence encoding a recombinase that binds to the recombination site of the landing pad of the acceptor cells. In some embodiments, the acceptor cells further comprise a polynucleotide sequence encoding a recombinase that binds to the recombination site of the landing pad of the acceptor cells.

In other aspects, the disclosure relates to polynucleotides comprising a 5' untranslated region (5' UTR) sequence screened according to a method described herein. In some embodiments, the polynucleotide comprises two or more 5' UTR sequences screened according to a method described herein, and wherein at least two of the 5' UTR sequences are separated by a linker. In some embodiments, at least two of the 5' UTR sequences have different polynucleotide sequences.

In some embodiments, the polynucleotide further comprises a promoter, wherein the promoter is positioned 5' to at least one of the 5' UTR sequences.

In some embodiments, the polynucleotide further comprises a polynucleotide sequence encoding a product of interest, wherein the one or more 5' UTR sequences are operably linked to the polynucleotide sequence encoding the product of interest.

In yet other aspects, the disclosure relates to compositions comprising a polynucleotide comprising a 5' untranslated region (5' UTR) sequence screened according to a method described herein.

In other aspects, the disclosure relates to methods of expressing a product of interest in a cell. In some embodiments, the method comprises contacting the cell with a polynucleotide comprising a polynucleotide sequence encoding a product of interest, thereby introducing the polynucleotide comprising the polynucleotide sequence encoding the product of interest into the cell, wherein the polynucleotide comprises a 5' untranslated region (5' UTR) sequence screened according to a method described herein. In some embodiments, the cell is contacted in vitro. In other embodiments, the cell is contacted in vivo.

These and other aspects of the invention are further described below.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the data illustrated in the drawings in no way limit the scope of the disclosure.

FIG. 3A. The workflow of cell line constructions. FIG. 3B. An illustration of recombinase-based gene integration.

FIG. 8A. The schematic illustration of the reporter plasmid. FIG. 8B. The fold-change of the reporter gene expression, where the ratio of GFP fluorescence and RFP expression was set as 1. Pairs of bars represent two independent sets of experiments.

FIG. 9A. The schematic illustration of the reporter plasmids. FIG. 9B. The fold-change of the reporter gene expression, where the ratio of GFP fluorescence and RFP expression was set as 1.

FIG. 10A. GFP reporter plasmid was placed with a second RFP reporter for normalization, which is on the same plasmid. The ratio of GFP fluorescence and RFP expression was set at 1. Pairs of bars represent two independent sets of experiments. FIG. 10B. GFP reporter was placed in pVAX1 plasmid, while co-transfected with a different plasmid expressing a second reporter. The ratio of GFP fluorescence and BFP expression was set as 1.

FIG. 11A. The illustrated scheme of the recombinase-mediated 5' UTR sequence library screening strategy. FIG. 11B. mRNA counts and ribosome counts can be measured using RNA-Seq and Ribo-Seq, respectively. FIG. 11C. The naturally-occurring (i.e., endogenous) 5' UTR sequence selection.

FIG. 13A. Workflow of the recombinase-based library screening. FIG. 13B. Construction of the 5' UTR sequence library and schematic illustration of recombinase-based gene integration. TAAACTTAAGCTTGGTACCG (SEQ ID NO: 4); GCCACCATGGTGAGCAAGGG (SEQ ID NO: 5). FIG. 13C. High reproducibility for barcode representations between two HEK-LP cell lines transfected with the library and a recombinase-expression plasmid throughout three bins based on GFP expression, which are top 0-2.5%, top 2.5-5%, and top 5-10%. ($\log_2$ values of normalized barcode counts). R is the Pearson correlation coefficient. FIG. 13D. Performance of the naturally occurring and synthetic 5' UTR sequences originated from HEK 293T cell line.

FIG. 14A. The 5' UTR sequences that modulate protein expression were ranked by their mean $\log_2$ ratios of the normalized barcode count in the three bins based on GFP expression. The UTR sequences that have a $\log_2$ ratio greater than 0.52 (which is highlighted as a dotted line) in all three bins were selected for further validation in this study. FIG. 14B. GFP gene was inserted to the pVAX1 plasmid to make the pVAX1-GFP plasmid, which was used as control in GFP expression study. The 5' UTR candidate sequences were inserted directly upstream of the KOZAK sequence of the GFP coding sequencing to make the pVAX1-UTR-GFP plasmids. FIG. 14C. Three 5' UTR candidates that significantly enhanced protein expression were chosen for further testing in this study. FIGS. 14D-14F. The effects of the three 5' UTR sequences on GFP (FIG. 14D), VEGF (FIG. 14E), and (CCL21) (FIG. 14F) expression in RD cells. The relative protein expression was normalized to that of the pVAX1 plasmid, set as 1 and highlighted as a dotted line. NuUTR1 corresponds to SEQ ID NO: 2; NuUTR2 corresponds to SEQ ID NO: 1; NuUTR3 corresponds to SEQ ID NO: 3.

FIG. 15A. Two of the three 5' UTR candidate sequences identified herein were conjugated with a CAACAA linker and inserted into the same position of the pVAX1-GFP plasmid to make the six 5' UTR combination plasmids. FIG. 15B. Test of the effects of the 5' UTR combinations on GFP expression in HEK-293T cells. The solid lines indicate the effect of NuUTR1 (SEQ ID NO: 2), NuUTR2 (SEQ ID NO: 1), and NuUTR3 (SEQ ID NO: 3) on GFP expression. FIG. 15C. Test of the single and combinatorial 5' UTR sequences on GFP expression on various cell lines. The relative protein expression was normalized to that of the pVAX1 plasmid, set as 1 and highlighted as a dotted line. For each cell line, bars are—from left to right—NuUTR1, NuUTR2, NuUTR3, CoNuUTR2-1, CoNuUTR3-1, CoNuUTR1-2, CoNuUTR3-2, CoNuUTR1-3, CoNuUTR2-3, pVAX1.

FIGS. 16A-6B. Workflow of the recombinase-based library screening strategy. FIG. 6A. Evaluation of model.

DETAILED DESCRIPTION

Figure 1:
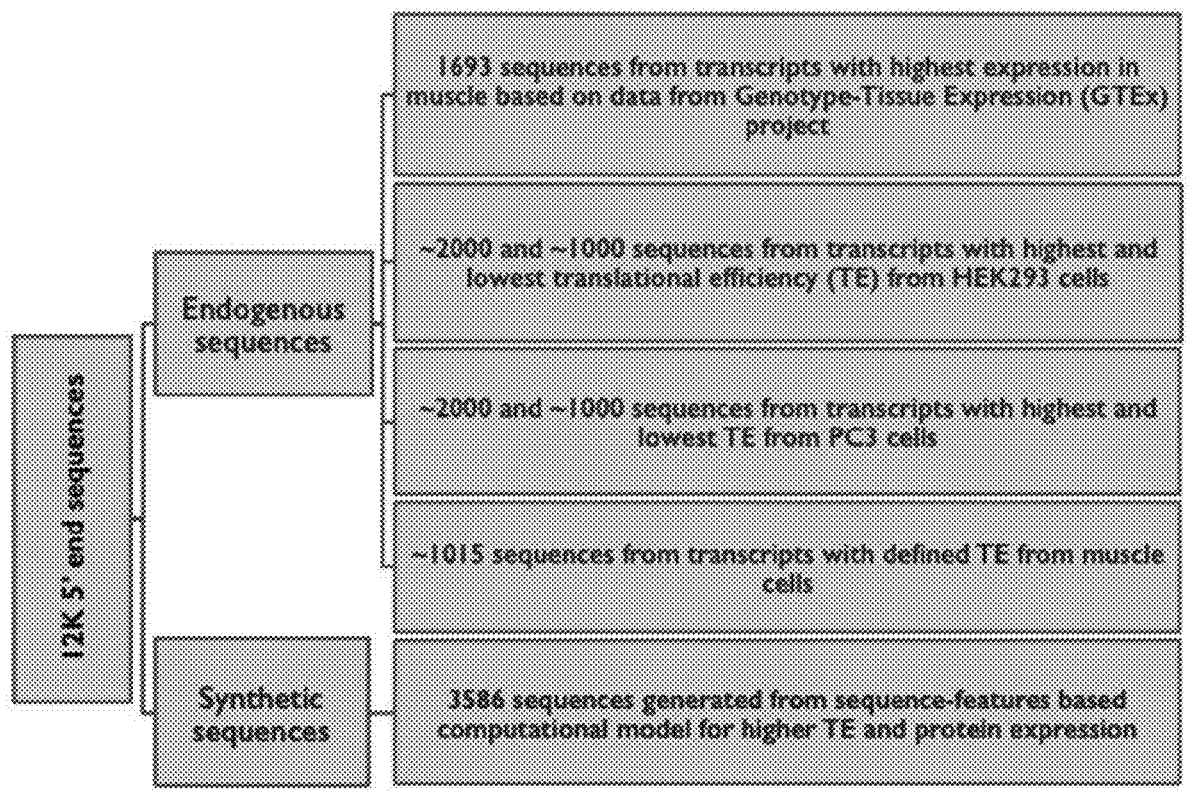
FIG. 1. Schematic depicting the design of a 5' UTR sequence library.

Disclosed herein is a comprehensive high-throughput strategy to design, screen, and optimize novel 5' UTR sequences, which can then be used fine tune protein expression in various contexts (e.g., gene therapy). To eliminate the copy number and position effects in traditional lentiviral screening, a recombinase-mediated library screening strategy was developed. Through this strategy, various synthetic 5' UTR sequences were identified which permit high heterogeneous gene expression in a variety of cell lines. Pairing these 5' UTR sequences enabled higher protein expression than obtained with each 5' UTR sequence individually. These synthetic 5' UTR sequences can be used, for example, to enhance in vivo drug productivity for DNA vaccine and mRNA therapeutics.

I. Methods of Generating a Population of 5' UTR Sequences, and Populations of 5' UTR Sequences Generated Thereby In some aspects, the disclosure relates to methods of generating a population of 5' untranslated region (5' UTR) sequences (or a population of nucleic acid molecules each comprising a 5' UTR sequence). As used herein, the term "5' UTR" refers to a polynucleotide sequence that, when linked to a transcript, is capable of recruiting ribosome complexes and initiating translation of the transcript. Typically, a 5' UTR is positioned directly upstream of the initiation codon of a transcript; specifically, between the cap site and the initiation codon. In other aspects, the disclosure relates to populations of 5' UTR sequences (or populations of nucleic acid molecules each comprising a 5' UTR sequence) generated by these methods.

A method of generating a population of 5' UTR sequences (or a population of nucleic acid molecules each comprising a 5' UTR sequence) may comprise the steps of: (a) providing an initial population of 5' UTR sequences (or an initial population of nucleic acid molecules each comprising a 5' UTR sequence); and (b) calculating a fitness score for each of the 5' UTR sequences in the initial population, wherein the fitness score reflects expression level or translation efficiency of a mRNA comprising the 5' UTR sequence.

The initial population of 5' UTR sequences (or initial population of nucleic acid molecules each comprising a 5' UTR sequence) in (a) may comprise one or more unique 5' UTR sequences. For example, in some embodiments, the initial population comprises at least 10, at least 20, at least 30, at least 40, at least 50, at least 60, at least 70, at least 80, at least 90, at least 100, at least 150, at least 200, at least 300, at least 400, at least 500, at least 600, at least 700, at least 800, at least 900, at least 1000, at least 1500, at least 2000, at least 2500, at least 3000, at least 3500, at least 4000, at least 4500, at least 5000, at least 5500, at least 6000, at least 6500, at least 7000, at least 7500, at least 8000, at least 8500, at least 9000, at least 9500, or at least 10,000 unique 5' UTR sequences.

One or more of the 5' UTR sequences (or nucleic acid molecules each comprising a 5' UTR sequence) in the initial population in (a) may comprise a synthetic sequence (i.e., a sequence that is not found in nature).

One or more of the 5' UTR sequences (or nucleic acid molecules each comprising a 5' UTR sequence) in the initial population in (a) may comprise an endogenous 5' UTR sequence (i.e., a 5' UTR sequence that is used in nature to recruit ribosome complexes and initiate translation of a transcript). For example, an endogenous 5' UTR sequence may be part of a mRNA expressed in a cell or population of cells. The cells in the population of cells may be the same type of cell (e.g., HEK-293 cells, PC3 cells, or muscle cells). Alternatively, the population of cells may comprise different cell types (e.g., HEK-293 cells, PC3 cells, and muscle cells). Methods of identifying mRNAs expressed in a cell or population of cells, and of identifying the 5' UTR sequences of the mRNAs, are known to those having skill in the art. Indeed, various public databases contain cellular mRNA expression and/or 5' UTR sequence information.

The length of the 5' UTR sequences (or the nucleic acid molecules each comprising a 5' UTR sequence) in the initial population of (a) may vary. For example, in some embodiments, at least two of the 5' UTR sequences in the initial population have different lengths. In some embodiments, at least two of the 5' UTR sequences in the initial population have the same length. In some embodiments, each of the 5' UTR sequences in the initial population of (a) have the same length.

In some embodiments, the length of at least one of the 5' UTR sequences in the initial population of (a) is 3, 4, 5, 6, 7, 8, 9, or 10 base pairs in length. In some embodiments, each of the 5' UTR sequences in the initial population of (a) is 3, 4, 5, 6, 7, 8, 9, or 10 base pairs in length.

In some embodiments, the length of at least one of the 5' UTR sequences (or the nucleic acid molecules each comprising a 5' UTR sequence) in the initial population of (a) is at least 10, at least 20, at least 30, at least 40, at least 50, at least 60, at least 70, at least 80, at least 90, at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, at least 1000, at least 1500, at least 2000, or at least 3000 base pairs in length. In some embodiments, the length of each of the 5' UTR sequences (or the nucleic acid molecules each comprising a 5' UTR sequence) in the initial population of (a) is at least 10, at least 20, at least 30, at least 40, at least 50, at least 60, at least 70, at least 80, at least 90, at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, at least 1000, at least 1500, at least 2000, or at least 3000 base pairs in length.

In some embodiments, the length of at least one of the 5' UTR sequences (or the nucleic acid molecules each comprising a 5' UTR sequence) in the initial population of (a) is 10-20, 10-30, 10-40, 10-50, 10-50, 10-60, 10-70, 10-80, 10-90, 10-100, 10-150, 10-200, 10-250, 10-300, 10-350, 10-400, 10-450, 10-500, 10-550, 10-600, 10-650, 10-700, 10-750, 10-800, 10-850, 10-900, 10-950, 10-1000, 20-30, 20-40, 20-50, 20-50, 20-60, 20-70, 20-80, 20-90, 20-100, 20-150, 20-200, 20-250, 20-300, 20-350, 20-400, 20-450, 20-500, 20-550, 20-600, 20-650, 20-700, 20-750, 20-800, 20-850, 20-900, 20-950, 20-1000, 30-40, 30-50, 30-50, 30-60, 30-70, 30-80, 30-90, 30-100, 30-150, 30-200, 30-250, 30-300, 30-350, 30-400, 30-450, 30-500, 30-550, 30-600, 30-650, 30-700, 30-750, 30-800, 30-850, 30-900, 30-950, 30-1000, 50-60, 50-70, 50-80, 50-90, 50-100, 50-150, 50-200, 50-250, 50-300, 50-350, 50-400, 50-450, 50-500, 50-550, 50-600, 50-650, 50-700, 50-750, 50-800, 50-850, 50-900, 50-950, 50-1000, 70-80, 70-90, 70-100, 70-150, 70-200, 70-250, 70-300, 70-350, 70-400, 70-450, 70-500, 70-550, 70-600, 70-650, 70-700, 70-750, 70-800, 70-850, 70-900, 70-950, 70-1000, 90-100, 90-150, 990-200, 90-250, 90-300, 90-350, 90-400, 90-450, 90-500, 90-550, 90-600, 90-650, 90-700, 90-750, 90-800, 90-850, 90-900, 90-950, or 90-1000 base pairs in length. In some embodiments, the length of each of the 5' UTR sequences (or the nucleic acid molecules each comprising a 5' UTR sequence) in the initial population of (a) is 10-20, 10-30, 10-40, 10-50, 10-50, 10-60, 10-70, 10-80, 10-90, 10-100, 10-150, 10-200, 10-250, 10-300, 10-350, 10-400, 10-450, 10-500, 10-550, 10-600, 10-650, 10-700, 10-750, 10-800, 10-850, 10-900, 10-950, 10-1000, 20-30, 20-40, 20-50, 20-50, 20-60, 20-70, 20-80, 20-90, 20-100, 20-150, 20-200, 20-250, 20-300, 20-350, 20-400, 20-450, 20-500, 20-550, 20-600, 20-650, 20-700, 20-750, 20-800, 20-850, 20-900, 20-950, 20-1000, 30-40, 30-50, 30-50, 30-60, 30-70, 30-80, 30-90, 30-100, 30-150, 30-200, 30-250, 30-300, 30-350, 30-400, 30-450, 30-500, 30-550, 30-600, 30-650, 30-700, 30-750, 30-800, 30-850, 30-900, 30-950, 30-1000, 50-60, 50-70, 50-80, 50-90, 50-100, 50-150, 50-200, 50-250, 50-300, 50-350, 50-400, 50-450, 50-500, 50-550, 50-600, 50-650, 50-700, 50-750, 50-800, 50-850, 50-900, 50-950, 50-1000, 70-80, 70-90, 70-100, 70-150, 70-200, 70-250, 70-300, 70-350, 70-400, 70-450, 70-500, 70-550, 70-600, 70-650, 70-700, 70-750, 70-800, 70-850, 70-900, 70-950, 70-1000, 90-100, 90-150, 990-200, 90-250, 90-300, 90-350, 90-400, 90-450, 90-500, 90-550, 90-600, 90-650, 90-700, 90-750, 90-800, 90-850, 90-900, 90-950, or 90-1000 base pairs in length.

In some embodiments, wherein the initial population of (a) comprises one or more endogenous 5' UTR sequences, the length of at least one endogenous 5' UTR sequence in the initial population is increased to a length of interest by added nucleotides to one or both ends (e.g., by adding repeats of a motif that does not have known secondary structure, such as CAA). Nucleotides may be added to the 5' end, the 3' end, or both the 5' and 3' ends of a 5' UTR sequence. In some embodiments, the length of one or more endogenous 5' UTR sequence in the initial population is decreased to a length of interest by removing nucleotides to one or both ends. Nucleotides may be removed from the 5' end, the 3' end, or both the 5' and 3' ends of a 5' UTR sequence.

In some embodiments, the fitness score for the 5' UTR sequences (e.g., the endogenous 5' UTR sequences) in (b) comprises: (i) measuring the abundances of a least a subset of the mRNAs in a cell or population of cells, wherein the subset of mRNAs collectively comprise the 5' UTR sequences; (ii) ranking the mRNAs of (i) according to their expression levels in the cell or population of cells; and (iii) assigning a fitness score to the 5' UTR sequences according to the ranking of the mRNAs in (ii). Methods of measuring mRNA abundances in a cell or population of cells are known to those having skill in the art and include but are not limited to RT-PCR, real time PCR, and RNA-Seq. When mRNAs are measured by RNA-Seq, the mRNAs may be ranked according to RPKM, where RPKM represents Reads Per Kilobase of transcript per Million mapped reads.

In other embodiments, the fitness score for the 5' UTR sequences (e.g., the endogenous 5' UTR sequences) in (b) comprises: (i) measuring the translation efficiencies of a least a subset of the mRNAs in a cell or population of cells, wherein the subset of mRNAs collectively comprise the endogenous 5' UTR sequences; (ii) ranking the mRNAs of (i) according to their translation efficiencies in the cell or population of cells; and (iii) assigning a fitness score to the endogenous 5' UTR sequences according to the ranking of the mRNAs in (ii). "Translation efficiency" refers to the rate at which a mRNA is translated into a protein. Translation efficiency may be measured directly, such as by measuring changes in protein levels (in vitro or in vivo) over time (e.g., by mass spectrometry). Alternatively, translation efficiency may be measured indirectly, such as by analyzing a mRNA's ribosome footprints (e.g., by Ribo-Seq). When translation efficiency is measured by Ribo-Seq, mRNAs may be ranked according to RPKM, where RPKM represents Reads Per Kilobase of transcript per Million mapped reads.

In yet other embodiments, the fitness score for the 5' UTR sequences (e.g., the endogenous 5' UTR sequences) in (b) comprises: (i) measuring the abundances and translation efficiencies of a least a subset of the mRNAs in a cell or population of cells, wherein the subset of mRNAs collectively comprise the endogenous 5' UTR sequences; (ii) ranking the mRNAs of (i) according to their protein expression, wherein protein expression is computed as: mRNA abundance*mRNA translation efficiency; and (iii) assigning a fitness score to the endogenous 5' UTR sequences according to the ranking of the mRNAs in (ii). mRNA abundance and mRNA translation efficiency may be measured as described above.

A method of generating a population of 5' UTR sequences (or a population of nucleic acid molecules each comprising a 5' UTR sequence) may comprise a step of selecting a subset of the 5' UTR sequences of the initial population (or a subset of the nucleic acid molecules from the initial population). For example, in some embodiments, a method of generating a population of 5' UTR sequences (or a population of nucleic acid molecules each comprising a 5' UTR sequence) comprises the steps of: (a) providing an initial population of 5' UTR sequences (or an initial population of initial population of nucleic acid molecules each comprising a 5' UTR sequence); (b) calculating a fitness score for each of the 5' UTR sequences in the initial population, wherein the fitness score reflects expression level or translation efficiency of a mRNA comprising the 5' UTR sequence; and (c) selecting a subset of the 5' UTR sequences of the initial population (or a subset of the nucleic acid molecules from the initial population).

A subset of the 5' UTR sequences of the initial population (or a subset of the nucleic acid molecules from the initial population) may comprise about the 40 percent, about the 39 percent, about the 38 percent, about the 37 percent, about the 36 percent, about the 35 percent, about the 34 percent, about the 33 percent, about the 32 percent, about the 31 percent, about the 30 percent, about the 29 percent, about the 28 percent, about the 27 percent, about the 26 percent, about the 25 percent, about the 24 percent, about the 23 percent, about the 22 percent, about the 21 percent, about the 20 percent, about the 19 percent, about the 18 percent, about the 17 percent, about the 16 percent, about the 15 percent, about the 14 percent, about the 13 percent, about the 12 percent, about the 11 percent, about the 10 percent, about the 9 percent, about the 8 percent, about the 7 percent, about the 6 percent, about the 5 percent, about the 4 percent, about the 3 percent, about the 2 percent, about the 1 percent, about the 0.9 percent, about the 0.8 percent, about the 0.6 percent, about the 0.5 percent, about the 0.4 percent, about the 0.3 percent, about the 0.2 percent, about the 0.1 percent, or about the 0.05 percent of 5' UTR sequences having the highest fitness score in (b).

A subset of the 5' UTR sequences of the initial population (or a subset of the nucleic acid molecules from the initial population) may comprise about the 40 percent, about the 39 percent, about the 38 percent, about the 37 percent, about the 36 percent, about the 35 percent, about the 34 percent, about the 33 percent, about the 32 percent, about the 31 percent, about the 30 percent, about the 29 percent, about the 28 percent, about the 27 percent, about the 26 percent, about the 25 percent, about the 24 percent, about the 23 percent, about the 22 percent, about the 21 percent, about the 20 percent, about the 19 percent, about the 18 percent, about the 17 percent, about the 16 percent, about the 15 percent, about the 14 percent, about the 13 percent, about the 12 percent, about the 11 percent, about the 10 percent, about the 9 percent, about the 8 percent, about the 7 percent, about the 6 percent, about the 5 percent, about the 4 percent, about the 3 percent, about the 2 percent, about the 1 percent, about the 0.9 percent, about the 0.8 percent, about the 0.6 percent, about the 0.5 percent, about the 0.4 percent, about the 0.3 percent, about the 0.2 percent, about the 0.1 percent, or about the 0.05 percent of 5' UTR sequences having the lowest fitness score in (b).

A subset of the 5' UTR sequences of the initial population (or a subset of the nucleic acid molecules from the initial population) may comprise about the 40 percent, about the 39 percent, about the 38 percent, about the 37 percent, about the 36 percent, about the 35 percent, about the 34 percent, about the 33 percent, about the 32 percent, about the 31 percent, about the 30 percent, about the 29 percent, about the 28 percent, about the 27 percent, about the 26 percent, about the 25 percent, about the 24 percent, about the 23 percent, about the 22 percent, about the 21 percent, about the 20 percent, about the 19 percent, about the 18 percent, about the 17 percent, about the 16 percent, about the 15 percent, about the 14 percent, about the 13 percent, about the 12 percent, about the 11 percent, about the 10 percent, about the 9 percent, about the 8 percent, about the 7 percent, about the 6 percent, about the 5 percent, about the 4 percent, about the 3 percent, about the 2 percent, about the 1 percent, about the 0.9 percent, about the 0.8 percent, about the 0.6 percent, about the 0.5 percent, about the 0.4 percent, about the 0.3 percent, about the 0.2 percent, about the 0.1 percent, or about the 0.05 percent of 5' UTR sequences having the highest fitness score in (b) and about the 40 percent, about the 39 percent, about the 38 percent, about the 37 percent, about the 36 percent, about the 35 percent, about the 34 percent, about the 33 percent, about the 32 percent, about the 31 percent, about the 30 percent, about the 29 percent, about the 28 percent, about the 27 percent, about the 26 percent, about the 25 percent, about the 24 percent, about the 23 percent, about the 22 percent, about the 21 percent, about the 20 percent, about the 19 percent, about the 18 percent, about the 17 percent, about the 16 percent, about the 15 percent, about the 14 percent, about the 13 percent, about the 12 percent, about the 11 percent, about the 10 percent, about the 9 percent, about the 8 percent, about the 7 percent, about the 6 percent, about the 5 percent, about the 4 percent, about the 3 percent, about the 2 percent, about the 1 percent, about the 0.9 percent, about the 0.8 percent, about the 0.6 percent, about the 0.5 percent, about the 0.4 percent, about the 0.3 percent, about the 0.2 percent, about the 0.1 percent, or about the 0.05 percent of 5' UTR sequences having the lowest fitness score in (b).

A method of generating a population of 5' UTR sequences (or a population of nucleic acid molecules each comprising a 5' UTR sequence) may comprise a step of extracting sequence features from the initial population of 5' UTR sequences. As used herein, a "sequence feature" refers to discrete characteristics of a 5' UTR sequence that individually impacts its ability to recruit ribosome complexes and/or initiate transcription. Examples of sequence features include, but are not limited to, k-mer frequency (i.e., the number of times a distinct k-mer is found in the sequence), codon usage, RNA folding energy, 5' UTR sequence length, and number of open reading frames (such as upstream open reading frames).

As used herein, the term "k-mer" refers to all of a particular sequence's length k subsequences. For example, the sequence AGAT would have four monomers (A, G, A, and T), three 2-mers (AG, GA, AT), two 3-mers (AGA and GAT) and one 4-mer (AGAT).

The term "codon usage" refers to the presence of specific trimers in the 5' UTR sequence. For example, upstream AUGs (or ATGs)—in particular out-of-frame upstream AUGs—and upstream termination sequences are functional elements in 5' UTR sequences that are known to affect the efficiency of translation.

A sequence feature may be RNA folding energy. RNA folding energy provides insights into secondary structure. For example, a highly negative folding free energy ($\Delta G$) level of a 5' UTR can be used to predict 5' UTR RNA secondary structures, which can impact translation efficiency. Examples of 5' UTR secondary structures that can impact translation efficiencies are known to those having skill in the art. Leppek K. et al., Nat. Rev. Mol. Cell Biol. 2018 March; 19(3): 158-174.

A method of generating a population of 5' UTR sequences (or a population of nucleic acid molecules each comprising a 5' UTR sequence) may comprise a step of training a machine learning model to learn a function that maps 5' UTR sequence features with fitness scores. For example, in some embodiments, a method of generating a population of 5' UTR sequences (or a population of nucleic acid molecules each comprising a 5' UTR sequence) comprises the steps of: (a) providing an initial population of 5' UTR sequences (or an initial population of initial population of nucleic acid molecules each comprising a 5' UTR sequence); (b) extracting sequence features from the 5' UTR sequences of the initial population of (a); (c) calculating a fitness score for each of the 5' UTR sequences in the initial population, wherein the fitness score reflects expression level or translation efficiency of a mRNA comprising the 5' UTR sequence and, accordingly, one or more of the sequence features of (b); and (d) training a machine learning model to learn a function that maps the sequence features of (b) with the fitness score of the 5' UTR comprising the feature in (c). Examples of machine learning models (e.g., random forest models) are known to those having skill in the art.

A method of generating a population of 5' UTR sequences (or a population of nucleic acid molecules each comprising a 5' UTR sequence) may comprise a step deriving a set of synthetic 5' UTR sequences. For example, in some embodiments, a method of generating a population of 5' UTR sequences (or a population of nucleic acid molecules each comprising a 5' UTR sequence) comprises the steps of: (a) providing an initial population of 5' UTR sequences (or an initial population of initial population of nucleic acid molecules each comprising a 5' UTR sequence); (b) extracting sequence features from the 5' UTR sequences of the initial population of (a); (c) calculating a fitness score for each of the 5' UTR sequences in the initial population, wherein the fitness score reflects expression level or translation efficiency of a mRNA comprising the 5' UTR sequence and, accordingly, one or more of the sequence features of (b); (d) training a machine learning model to learn a function that maps the sequence features of (b) with the fitness score of the 5' UTR comprising the feature in (c); and (e) deriving a set of synthetic 5' UTR sequences from a second population of 5' UTR sequences (or population of nucleic acid molecules each comprising a 5' UTR sequence), wherein the synthetic 5' UTR sequences have a different predicted fitness score than the 5' UTR sequences from which they are derived, wherein the predicted fitness score is calculated according to the function of (d). The second population of 5' UTR sequences (or population of nucleic acid molecules each comprising a 5' UTR sequence) in (e) may comprise a subset of the initial population of (a) and/or 5' UTR sequences (or population of nucleic acid molecules each comprising a 5' UTR sequence) not found in the initial population of (a).

The step of deriving a set of synthetic 5' UTR sequences from a second population of 5' UTR sequences (or population of nucleic acid molecules each comprising a 5' UTR sequence) may comprise: (i) selecting a population of 5' UTR sequences; (ii) calculating fitness scores for the 5' UTR sequences of the population of (i) according to the function of (d); (iii) introducing mutations in the 5' UTR sequences of the population of (i), thereby generating a population of mutated 5' UTR sequences; (iv) calculating fitness scores for the 5' UTR sequences of the population of mutated 5' UTR sequences according to the function of (d); (v) selecting a subset of 5' UTR sequences from the population of mutated 5' UTR sequences, wherein the subset consists of: 5' UTR sequences having a higher predicted fitness score than the 5' UTR sequences from which they are derived, wherein the predicted fitness score is calculated according to the function of (d).

The mutations may be introduced in (iii) using a genetic algorithm. Examples of genetic algorithms are known to those having skill in the art. See e.g., Scrucca, L. GA: A Package for Genetic Algorithms in R. J. Stat. Softw. (2015). doi:10.18637/jss.v053.i04. The number of mutations introduced into each of the 5' UTR sequences of the population of (i) may vary. In some embodiments, at least two of the 5' UTR sequences are mutated to a different extent. In some embodiments, at least two of the 5' UTR sequences are mutated to the same extent. In some embodiments, each of the 5' UTR sequences are mutated to the same extent.

In some embodiments, at least one 5' UTR sequence is mutated at 1, 2, 3, 4, 5, 6, 7, 8, 9, 10, 11, 12, 13, 14, 15, 16, 17, 18, 19, or 20 nucleotide positions. In some embodiments, each 5' UTR sequence is mutated at 1, 2, 3, 4, 5, 6, 7, 8, 9, 10, 11, 12, 13, 14, 15, 16, 17, 18, 19, or 20 nucleotide positions. A mutation may comprise a base pair substitution, a deletion, or an insertion.

In some embodiments, at least one 5' UTR sequence is mutated at 1-2, 1-3, 1-4, 1-5, 1-6, 1-7, 1-8, 1-9, 1-10, 2-3, 2-4, 2-5, 2-6, 2-7, 2-8, 2-9, 2-10, 3-4, 3-5, 3-6, 3-7, 3-8, 3-9, 3-10, 4-5, 4-6, 4-7, 4-8, 4-9, 4-10, 5-6, 5-7, 5-8, 5-9, 5-10, 6-7, 6-8, 6-9, 6-10, 7-8, 7-9, 7-10, 8-9, 8-10, or 9-10 nucleotide positions. In some embodiments, each 5' UTR sequence is mutated at 1-2, 1-3, 1-4, 1-5, 1-6, 1-7, 1-8, 1-9, 1-10, 2-3, 2-4, 2-5, 2-6, 2-7, 2-8, 2-9, 2-10, 3-4, 3-5, 3-6, 3-7, 3-8, 3-9, 3-10, 4-5, 4-6, 4-7, 4-8, 4-9, 4-10, 5-6, 5-7, 5-8, 5-9, 5-10, 6-7, 6-8, 6-9, 6-10, 7-8, 7-9, 7-10, 8-9, 8-10, or 9-10 nucleotide positions.

Steps (i)-(v) (of the deriving methods described above) may be repeated one or more times. For example, in some embodiments, steps (i)-(v) are repeated 2, 3, 4, 5, 6, 7, 8, 9, 10, 11, 12, 13, 14, 15, 16, 17, 18, 19, 20, about 25, about 30, about 35, about 40, about 45, about 50, about 55, about 60, about 65, about 70, about 75, about 80, about 85, about 90, about 95, about 100, about 110, about 120, about 130, about 140, about 150, about 160, about 170, about 180, about 190, about 200, about 250, about 300, about 350, about 400, about 450, about 500, about 600, about 700, about 800, about 900, or about 1000 times. In some embodiments, steps (i)-(v) are repeated at least 2, at least 3, at least 4, at least 5, at least 6, at least 7, at least 8, at least 9, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 150, at least 200, at least 250, at least 300, at least 350, at least 400, at least 450, at least 500, or at least 1000 times.

In some embodiments, the synthetic 5' UTR sequences have a higher predicted fitness score than the 5' UTR sequences from which they are derived. For example, in some embodiments, the predicted fitness scores of the synthetic 5' UTR sequences are higher than the 5' UTR sequences from which they are derived by at least 1.5 or 2 fold. In some embodiments, the predicted fitness scores of the synthetic 5' UTR sequences are higher than the 5' UTR sequences from which they are derived by about 2, 3, 4, 5, 6, 7, 8, 9, or 10 fold. In some embodiments, the predicted fitness scores of the synthetic 5' UTR sequences are higher than the 5' UTR sequences from which they are derived by about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, or 100 percent.

In other embodiments, the synthetic 5' UTR sequences have a lower predicted fitness score than the 5' UTR sequences from which they are derived. For example, in some embodiments, the predicted fitness scores of the synthetic 5' UTR sequences are lower than the 5' UTR sequences from which they are derived by about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, or 95 percent.

A method of generating a population of 5' UTR sequences (or a population of nucleic acid molecules each comprising a 5' UTR sequence) may comprise a step of synthesizing a population of 5' UTR sequences (or a population of nucleic acid molecules each comprising a 5' UTR sequence). A method of generating a population of 5' UTR sequences (or a population of nucleic acid molecules each comprising a 5' UTR sequence) may also comprise validating the translation efficiency of one or more of the 5' UTR sequences (or nucleic acid molecules each comprising a 5' UTR sequence) in a cell.

In some aspects, the disclosure relates to populations of 5' UTR sequences (or a population of nucleic acid molecules each comprising a 5' UTR sequence) synthesized according to the methods described herein.

The population of 5' UTR sequences that are synthesized may comprise one or more unique 5' UTR sequences. For example, in some embodiments, one, two, three, four, five, six, seven, eight, nine, or ten unique 5' UTR sequences are synthesized. In other embodiments, at least 10, at least 20, at least 30, at least 40, at least 50, at least 60, at least 70, at least 80, at least 90, at least 100, at least 150, at least 200, at least 300, at least 400, at least 500, at least 600, at least 700, at least 800, at least 900, at least 1000, at least 1500, at least 2000, at least 2500, at least 3000, at least 3500, at least 4000, at least 4500, at least 5000, at least 5500, at least 6000, at least 6500, at least 7000, at least 7500, at least 8000, at least 8500, at least 9000, at least 9500, or at least 10,000 unique 5' UTR sequences are synthesized.

The length of the 5' UTR sequences (or the nucleic acid molecules each comprising a 5' UTR sequence) that are synthesized may vary. For example, in some embodiments, at least two of the 5' UTR sequences that are synthesized have different lengths. In some embodiments, at least two of the 5' UTR sequences that are synthesized have the same length. In some embodiments, each of the 5' UTR sequences that are synthesized have the same length.

In some embodiments, the length of at least one of the 5' UTR sequence (or the nucleic acid molecules each comprising a 5' UTR sequence) that is synthesized is at least 10, at least 20, at least 30, at least 40, at least 50, at least 60, at least 70, at least 80, at least 90, at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, at least 1000, at least 1500, at least 2000, or at least 3000 base pairs in length. In some embodiments, the length of each of the 5' UTR sequences (or the nucleic acid molecules each comprising a 5' UTR sequence) that is synthesized is at least 10, at least 20, at least 30, at least 40, at least 50, at least 60, at least 70, at least 80, at least 90, at least 100, at least 150, at least 200, at least 250, at least 300, at least 350, at least 400, at least 450, at least 500, at least 550, at least 600, at least 650, at least 700, at least 750, at least 800, at least 850, at least 900, at least 950, at least 1000, at least 1500, at least 2000, or at least 3000 base pairs in length.

In some embodiments, the length of at least one of the 5' UTR sequences is 10-20, 10-30, 10-40, 10-50, 10-50, 10-60, 10-70, 10-80, 10-90, 10-100, 10-150, 10-200, 10-250, 10-300, 10-350, 10-400, 10-450, 10-500, 10-550, 10-600, 10-650, 10-700, 10-750, 10-800, 10-850, 10-900, 10-950, 10-1000, 20-30, 20-40, 20-50, 20-50, 20-60, 20-70, 20-80, 20-90, 20-100, 20-150, 20-200, 20-250, 20-300, 20-350, 20-400, 20-450, 20-500, 20-550, 20-600, 20-650, 20-700, 20-750, 20-800, 20-850, 20-900, 20-950, 20-1000, 30-40, 30-50, 30-50, 30-60, 30-70, 30-80, 30-90, 30-100, 30-150, 30-200, 30-250, 30-300, 30-350, 30-400, 30-450, 30-500, 30-550, 30-600, 30-650, 30-700, 30-750, 30-800, 30-850, 30-900, 30-950, 30-1000, 50-60, 50-70, 50-80, 50-90, 50-100, 50-150, 50-200, 50-250, 50-300, 50-350, 50-400, 50-450, 50-500, 50-550, 50-600, 50-650, 50-700, 50-750, 50-800, 50-850, 50-900, 50-950, 50-1000, 70-80, 70-90, 70-100, 70-150, 70-200, 70-250, 70-300, 70-350, 70-400, 70-450, 70-500, 70-550, 70-600, 70-650, 70-700, 70-750, 70-800, 70-850, 70-900, 70-950, 70-1000, 90-100, 90-150, 990-200, 90-250, 90-300, 90-350, 90-400, 90-450, 90-500, 90-550, 90-600, 90-650, 90-700, 90-750, 90-800, 90-850, 90-900, 90-950, or 90-1000 base pairs in length. In some embodiments, the length of each of the 5' UTR sequences is 10-20, 10-30, 10-40, 10-50, 10-50, 10-60, 10-70, 10-80, 10-90, 10-100, 10-150, 10-200, 10-250, 10-300, 10-350, 10-400, 10-450, 10-500, 10-550, 10-600, 10-650, 10-700, 10-750, 10-800, 10-850, 10-900, 10-950, 10-1000, 20-30, 20-40, 20-50, 20-50, 20-60, 20-70, 20-80, 20-90, 20-100, 20-150, 20-200, 20-250, 20-300, 20-350, 20-400, 20-450, 20-500, 20-550, 20-600, 20-650, 20-700, 20-750, 20-800, 20-850, 20-900, 20-950, 20-1000, 30-40, 30-50, 30-50, 30-60, 30-70, 30-80, 30-90, 30-100, 30-150, 30-200, 30-250, 30-300, 30-350, 30-400, 30-450, 30-500, 30-550, 30-600, 30-650, 30-700, 30-750, 30-800, 30-850, 30-900, 30-950, 30-1000, 50-60, 50-70, 50-80, 50-90, 50-100, 50-150, 50-200, 50-250, 50-300, 50-350, 50-400, 50-450, 50-500, 50-550, 50-600, 50-650, 50-700, 50-750, 50-800, 50-850, 50-900, 50-950, 50-1000, 70-80, 70-90, 70-100, 70-150, 70-200, 70-250, 70-300, 70-350, 70-400, 70-450, 70-500, 70-550, 70-600, 70-650, 70-700, 70-750, 70-800, 70-850, 70-900, 70-950, 70-1000, 90-100, 90-150, 990-200, 90-250, 90-300, 90-350, 90-400, 90-450, 90-500, 90-550, 90-600, 90-650, 90-700, 90-750, 90-800, 90-850, 90-900, 90-950, or 90-1000 base pairs in length.

II. Methods of Screening 5' UTR Sequences for a Characteristic of Interest

In some aspects, the disclosure relates to methods of screening a library of 5' untranslated region (5' UTR) sequences for a characteristic of interest (e.g., a desired translation efficiency level). The characteristic of interest may be any range of translation efficiency. In some embodiments, a characteristic of interest is a high translation efficiency. In other embodiments, a characteristic of interest may be a low translation efficiency.

In some embodiments, a method of screening 5' UTR sequences comprises: (a) providing (e.g., synthesizing) a population of donor polynucleotides collectively comprising a library of 5' UTR sequences, wherein each donor polynucleotide comprises: (i) a donor cassette; and (ii) a recombinase attachment site; (b) contacting the population of donor polynucleotides of (a) with a population of acceptor cells, wherein each of the acceptor cells comprises a landing pad localized at a common genetic location (i.e., the landing pad is localized at the same genomic location in each cell), wherein the landing pad comprises a recombinase attachment site that is compatible with the recombinase attachment site of a donor polynucleotide; (c) expressing a recombinase in the acceptors cells to induce recombination between the donor polynucleotides of (a) and the acceptor cells of (b), thereby generating a population of recombined cells, wherein each of the recombined cells comprises the donor cassette of a donor polynucleotide; and (d) identifying the 5' UTR sequences having the characteristic of interest according to the level of output protein in the recombined cells.

As used herein, "polynucleotide" or "polynucleotides" is used interchangeably with "nucleic acid molecules" or "nucleic acid molecules," respectively.

An acceptor cell may comprise one or more landing pad. As used herein, the term "landing pad" refers to an exogenous polynucleotide sequence (i.e., a non-natural polynucleotide sequence) that facilitates the targeted insertion of transgenes (e.g., a donor cassette) into the cell's genome. Accordingly, a landing pad is integrated into the genome of the cell.

A donor polynucleotide and/or a landing pad may comprise one or more recombinase attachment site. Recombinases are enzymes that catalyze site-specific recombination events within DNA at specific nucleotide sequences (i.e., recombinase attachments sites). Examples of recombinases (and recombinase attachment site corresponding to the recombinases) are known to those having skill in the art and include, but are not limited to, serine recombinases, such as Bxb1 integrase, lambda-integrase, Cre recombinase, Flp recombinase, gamma-delta resolvase, Tn3 resolvase, φC31 integrase, and R4 integrase. Exemplary attachment site sequences include but are not limited to attP, attB, attR, attL, Lox, and Frt.

The recombinase attachment site(s) of the donor polynucleotides and the recombinase attachment site(s) of a landing pad are compatible. For example, the recombinase attachment site(s) of the donor polynucleotides and the recombinase attachment site(s) may comprise attachment sites corresponding to a Bxb1 integrase, lambda-integrase, Cre recombinase, Flp recombinase, gamma-delta resolvase, Tn3 resolvase, φC31 integrase, or R4 integrase. In some embodiments, the recombinase attachment sites correspond to a Bxb1 integrase. See e.g., FIG. 3B, FIG. 13B. In some embodiments, the recombinase sites of the donor polynucleotides are attB recombinase sites and the recombinase sites of the landing pads of the acceptor cells are attP recombinase sites (e.g., mutant attP site with enhanced integration efficiency).

The recombinase attachment sites may mediate excision/insertion, inversion, translocation or cassette exchange. In some embodiments, the donor polynucleotide is integrated into the genome of the cell. In some embodiments, only a fraction of the donor polynucleotide (e.g., the donor cassette) is integrated into the genome of the cell.

In some embodiments, recombination between the donor polynucleotide and the acceptor cell destroys the recombinase attachment site of the landing pad of the acceptor cell, thereby prohibiting further recombination at the landing pad.

A donor cassette may comprise a promoter, a 5' UTR sequence from a library of 5' UTR sequences, and a polynucleotide sequence encoding an output protein. As used herein, the term "promoter" refers to a polynucleotide sequence that is capable of initiating transcription of a polynucleotide sequence to which it is attached (e.g., a polynucleotide sequence encoding a gene). Examples of promoter sequences are known to those having skill in the art. A promoter may be a constitutive promoter or an inducible promoter. In some embodiments, the promoter is a CMV promoter.

The output protein may comprise a reporter protein, such as a fluorescent protein. Non-limiting exemplary reporter proteins can be wt-GFP, green fluorescent protein (e.g., EGFP, Emerald, Superfolder GFP, Azami Green, mWasabi, TagGFP, TurboGFP, AcGFP, ZsGreen, T-Sapphire, etc.), blue fluorescent protein, (e.g., EBFP, EBFP2, Azurite, mTagBFP, etc.), cyan fluorescent protein (e.g., ECFP, mECFP, Cerulean, mTurquoise, CyPet, AmCyan1, Midori-Ishi Cyan, TagCFP, mTFP1 (Teal), etc.), yellow fluorescent protein (e.g., EYFP, Topaz, Venus, mCitrine, YPet, TagYFP, PhiYFP, ZsYellow1, mBanana, etc.), orange fluorescent protein (e.g., Kusabira Orange, Kusabira Orange2, mOrange, mOrange2, dTomato, dTomato-Tandem, TagRFP, TagRFP-T, DsRed, DsRed2, DsRed-Express (T1), DsRed-Monomer, mTangerine, etc.), or red fluorescent protein (e.g., mRuby, mApple, mStrawberry, AsRed2, mRFP1, JRed, mCherry, HcRed1, mRaspberry, dKeima-Tandem, HcRed-Tandem, mPlum, AQ143, etc.), luciferase, or b-galactosidase.

In some embodiments, the output protein may comprise a therapeutic protein (e.g., VEGF, CCL21, etc.).

The donor cassette may further comprise a polynucleotide sequence encoding a selectable marker. In some embodiments, a selectable marker comprises an antibiotic resistance protein. Examples of antibiotic resistance proteins are known to those having skill in the art and include, but are not limited to, puromycin and hygromycin. In some embodiments, the selectable marker comprises a fluorescent protein. In some embodiments, a selectable maker comprises a polynucleotide sequence encoding an antibiotic resistance protein and a fluorescent protein, wherein the polynucleotide sequences are separated by a polynucleotide sequence encoding a polycistronic expression element (e.g., a viral 2a peptide).

A donor cassette may further comprise a sequence encoding a 3' UTR and/or a polyadenylation signal (e.g., a bovine growth hormone polyadenylation signal).

A recombinase may be expressed in an acceptor cell naturally or transgenically. In some embodiments, an acceptor cell comprises a genomic integration of a polynucleotide sequence encoding a recombinase protein (e.g., Bxb1), wherein the sequence encoding the recombinase protein is operably linked to a promoter sequence (e.g., a constitutive or inducible promoter). In some embodiments, an acceptor cell comprises a non-integrated polynucleotide sequence encoding a recombinase protein (e.g., Bxb1), wherein the sequence encoding the recombinase protein is operably linked to a promoter sequence (e.g., a constitutive or inducible promoter). Methods of introducing polynucleotide sequences into a cell are known to those having skill in the art.

In some embodiments, the step of identifying the 5' UTR sequences having the characteristic of interest according to the level of output protein in the recombined cells comprises: (i) dividing the cells into at least two bins according to the level of output protein in the recombined cells; (ii) isolated genomic DNA from the recombined cells of one or more of the bins; and (iii) sequencing the genomic DNA to identify the 5' UTR sequences having the characteristic of interest (e.g., by high throughput sequencing).

The number of bins that the recombined cells are divided into may vary. For example, in some embodiments the recombined cells are divided into 2, 3, 4, 5, 6, 7, 8, 9, 10, 11, 12, 13, 14, 15, 16, 17, 18, 19, 20, 21, 22, 23, 24, 25, 26, 27, 28, 29, or 30 bins. In some embodiments, the recombined cells are divided into at least 2, at least 3, at least 4, at least 5, at least 6, at least 7, at least 8, at least 9, at least 10, at least 11, at least 12, at least 13, at least 14, at least 15, at least 20, at least 25, or at least 30 bins.

The sizes of the bins (i.e., as a percentage of the total number of recombined cells) may vary. For example, in some embodiments, at least two of the bins differ in size. In some embodiments, at least two of the bins are the same size. In some embodiments, each of the bins are the same size.

In some embodiments, at least one bin comprises about 1 percent, about 2 percent, about 3 percent, about 4 percent, about 5 percent, about 6 percent, about 7 percent, about 8 percent, about 9 percent, about 10 percent, about 11 percent, about 12 percent, about 13 percent, about 14 percent, about 15 percent, about 16 percent, about 17 percent, about 18 percent, about 19 percent, about 20 percent, about 21 percent, about 22 percent, about 23 percent, about 24 percent, about 25 percent, about 26 percent, about 27 percent, about 28 percent, about 29 percent, or about 30 percent of the total recombined cells. In some embodiments, each bin comprises about 1 percent, about 2 percent, about 3 percent, about 4 percent, about 5 percent, about 6 percent, about 7 percent, about 8 percent, about 9 percent, about 10 percent, about 11 percent, about 12 percent, about 13 percent, about 14 percent, about 15 percent, about 16 percent, about 17 percent, about 18 percent, about 19 percent, about 20 percent, about 21 percent, about 22 percent, about 23 percent, about 24 percent, about 25 percent, about 26 percent, about 27 percent, about 28 percent, about 29 percent, or about 30 percent of the total recombined cells.

In some embodiments, at least one bin comprises about 1-2, 1-3, 1-4, 1-5, 1-6, 1-7, 1-8, 1-9, 1-10, 1-15, 1-20, 1-25, 1-30, 1-40, 1-50, 2-3, 2-4, 2-5, 2-6, 2-7, 2-8, 2-9, 2-10, 2-15, 2-20, 2-25, 2-30, 2-40, 2-50, 3-4, 3-5, 3-6, 3-7, 3-8, 3-9, 3-10, 3-15, 3-20, 3-25, 3-30, 3-40, 3-50, 4-5, 4-6, 4-7, 4-8, 4-9, 4-10, 4-15, 4-20, 4-25, 4-30, 4-40, 4-50, 5-6, 5-7, 5-8, 5-9, 5-10, 5-15, 5-20, 5-25, 5-30, 5-40, 5-50, 6-7, 6-8, 6-9, 6-10, 6-15, 6-20, 6-25, 6-30, 5-40, 6-50, 7-8, 7-9, 7-10, 7-15, 7-20, 7-25, 7-30, 7-40, 7-50, 8-9, 8-10, 8-15, 8-20, 8-25, 8-30, 8-40, 8-50, 9-10, 9-15, 9-20, 9-25, 9-30, 9-40, 9-50, 10-15, 10-20, 10-25, 10-30, 10-40, 10-50, 15-20, 15-25, 15-30, 15-40, 15-50, 20-25, 20-30, 20-40, 20-50, 25-30, 25-40, 25-50, 30-40, 30-50, or 40-50 percent of the total recombined cells. In some embodiments, each bin comprises about 1-2, 1-3, 1-4, 1-5, 1-6, 1-7, 1-8, 1-9, 1-10, 1-15, 1-20, 1-25, 1-30, 1-40, 1-50, 2-3, 2-4, 2-5, 2-6, 2-7, 2-8, 2-9, 2-10, 2-15, 2-20, 2-25, 2-30, 2-40, 2-50, 3-4, 3-5, 3-6, 3-7, 3-8, 3-9, 3-10, 3-15, 3-20, 3-25, 3-30, 3-40, 3-50, 4-5, 4-6, 4-7, 4-8, 4-9, 4-10, 4-15, 4-20, 4-25, 4-30, 4-40, 4-50, 5-6, 5-7, 5-8, 5-9, 5-10, 5-15, 5-20, 5-25, 5-30, 5-40, 5-50, 6-7, 6-8, 6-9, 6-10, 6-15, 6-20, 6-25, 6-30, 5-40, 6-50, 7-8, 7-9, 7-10, 7-15, 7-20, 7-25, 7-30, 7-40, 7-50, 8-9, 8-10, 8-15, 8-20, 8-25, 8-30, 8-40, 8-50, 9-10, 9-15, 9-20, 9-25, 9-30, 9-40, 9-50, 10-15, 10-20, 10-25, 10-30, 10-40, 10-50, 15-20, 15-25, 15-30, 15-40, 15-50, 20-25, 20-30, 20-40, 20-50, 25-30, 25-40, 25-50, 30-40, 30-50, or 40-50 percent of the total recombined cells.

III. Kits

In some embodiments, the disclosure relates to kits for screening a library of 5' untranslated region (5' UTR) sequences for a characteristic of interest (e.g., a desired translation efficiency level), for example as described above. The characteristic of interest may be any range of translation efficiency. In some embodiments, a characteristic of interest is a high translation efficiency. In other embodiments, a characteristic of interest may be a low translation efficiency.

A kit may comprise one or more population of acceptor cells (i.e., lines of acceptor cells), wherein each of the acceptor cells in a population comprises a landing pad localized at a common genetic location (i.e., the landing pad is localized at the same genomic location in each cell), wherein the landing pad comprises a recombinase attachment site. The kit may comprise one, two, three, four, five, six, seven, eight, nine, or then lines of acceptor cells. The acceptor cells may be prokaryotic cells or eukaryotic cells.

The acceptor cells of the kit may further comprise a polynucleotide sequence encoding a recombinase that binds to the recombination site of the landing pad of the acceptor cells. Alternatively or in addition, the kit may further comprise a polynucleotide sequence encoding a recombinase that binds to the recombination site of the landing pad of the acceptor cells.

IV. Synthetic 5' UTR Sequences

In other aspects, the disclosure relates to synthetic 5' untranslated region (5' UTR) sequences. The synthetic 5' UTR sequences may have been synthesized or screened according to the methods described herein.

In some embodiments, a synthetic 5' untranslated region (5' UTR) sequence comprises the polynucleotide sequence of:

```
                                             (SEQ ID NO: 1)
CACTCGCGCTGCCATCACTCTTCCGCCGTCTTCGCCGCCATCCTCGGCG

CGACTCGCTTCTTTCGGTTCTACCAGGTAGAGTCCGCCGCCATCCTCCA

CC;
                                             (SEQ ID NO: 2)
CATTCTGTGGTCTGATCATCCTGTGGTTTCGTCGCCGCCATCCTCGTCG

CGACACGCTGTTTTCGGTTCTCGGCCCGACGAGCCATCGCCATCCTACA

GC;
or
                                             (SEQ ID NO: 3)
CTTGTCTCGCTCCGGGGAACGCTCGGAAACTCCCGGCCGCCGCCACCCG

CGTCTGTTCTGTTACACAAGGGAAGAAAAGCCGCTGCCGCACTCCGAGT

GT.
```

In other aspects, the disclosure relates to polynucleotides comprising a synthetic 5' UTR sequence. The synthetic 5' UTR sequences may have been synthesized or screened according to the methods described herein.

In some embodiments, a polynucleotide comprises one or more 5' UTR sequences, at least one of which is a synthetic 5' UTR sequence. In some embodiments, at least one of the synthetic 5' UTR sequences comprises the polynucleotide sequence of:

```
                                             (SEQ ID NO: 1)
CACTCGCGCTGCCATCACTCTTCCGCCGTCTTCGCCGCCATCCTCGGCG

CGACTCGCTTCTTTCGGTTCTACCAGGTAGAGTCCGCCGCCATCCTCCA

CC;
                                             (SEQ ID NO: 2)
CATTCTGTGGTCTGATCATCCTGTGGTTTCGTCGCCGCCATCCTCGTCG

CGACACGCTGTTTTCGGTTCTCGGCCCGACGAGCCATCGCCATCCTACA

GC;
``` or (SEQ ID NO: 3)
CTTGTCTCGCTCCGGGGAACGCTCGGAAACTCCCGGCCGCCGCCACCCG

CGTCTGTTCTGTTACACAAGGGAAGAAAAGCCGCTGCCGCACTCCGAGT

GT.

In some embodiments, a polynucleotide comprises two or more synthetic 5' UTR sequences. For example, in some embodiment, a polynucleotide comprises, two, three, four, five, six, seven, eight, nine, or ten synthetic 5' UTR sequences. In some embodiments, at least two of the synthetic 5' UTR sequences have the same sequence. In some embodiments, at least two of the synthetic 5' UTR sequences have different sequences. In some embodiments, at least two of the 5' UTR sequences are separated by a linker sequence (e.g., a CACCACA linker). Exemplary combinations of synthetic 5' UTR sequences are provided in FIG. 15C and in Example 2 (SEQ ID NOs: 8-13). In some embodiments, the 5' UTR sequence having the higher translation efficiency is positioned at the 3' end (i.e., closest to the translation initiation site).

A polynucleotide comprising one or more 5' UTR sequences, at least one of which is a synthetic 5' UTR sequence, may further comprise a promoter, wherein the promoter is positioned 5' to at least one of the synthetic 5' UTR sequences. The promoter may be a constitutive promoter or an inducible promoter. In some embodiments, the promoter is a CMV promoter.

A polynucleotide comprising one or more 5' UTR sequences, at least one of which is a synthetic 5' UTR sequence, may further comprise a polynucleotide sequence encoding a product of interest, wherein at least one of the synthetic 5' UTR sequences is operably linked to the polynucleotide sequence encoding the product of interest.

In yet other aspects, the disclosure relates to compositions comprising a polynucleotide comprising a synthetic 5' UTR sequence as described herein.

V. Methods of Expressing a Product of Interest in a Cell

In other aspects, the disclosure relates to methods of expressing a product of interest in a cell (e.g., gene therapy). A product of interest may be, for example, a therapeutic molecule.

A therapeutic molecule may be a protein. In some embodiments, the therapeutic protein is an antibody, a single chain antibody, an antibody fragment, an intrabody, an aptamer, an immunomodulatory protein, an enzyme, a cofactor, a receptor, a ligand, a transcription regulatory protein, a DNA editing protein, translational regulatory protein, an antigen, a growth factor, a hormone, a cytokine, a chemokine, a clotting factor, a signaling protein, a biosynthetic pathway component or the like. These peptide-based therapeutic molecules may or may not be naturally occurring.

Non-limiting exemplary therapeutic proteins include interferon-γ (IFN-γ), IFN-α, Interleukin-1 (IL-1), IL-2, IL-3, IL-4, IL-5, IL-6, IL-7, IL-10, IL-12, IL-13, IL-17, IL-18, CCL14, CCL19, CCL20, CCL21, CCL25, CCL27, CXCL12, CXCL13, CXCL-8, CCL2, CCL3, CCL4, CCL5, CCL11, CXCL10, Adrenomedullin (AM), Angiopoietin (Ang), Autocrine motility factor, Bone morphogenetic proteins (BMPs), Ciliary neurotrophic factor (CNTF), Leukemia inhibitory factor (LIF), Interleukin-6 (IL-6), Macrophage colony-stimulating factor (m-CSF), Granulocyte colony-stimulating factor (G-CSF), Granulocyte macrophage colony-stimulating factor (GM-CSF), Epidermal growth factor (EGF), Ephrin A1, Ephrin A2, Ephrin A3, Ephrin A4, Ephrin A5, Ephrin B1, Ephrin B2, Ephrin B3, Erythropoietin (EPO), Fibroblast growth factor 1 (FGF1), Fibroblast growth factor 2 (FGF2), Fibroblast growth factor 3 (FGF3), Fibroblast growth factor 4 (FGF4), Fibroblast growth factor 5 (FGF5), Fibroblast growth factor 6 (FGF6), Fibroblast growth factor 7 (FGF7), Fibroblast growth factor 8 (FGF8), Fibroblast growth factor 9 (FGF9), Fibroblast growth factor 10 (FGF10), Fibroblast growth factor 11 (FGF11), Fibroblast growth factor 12 (FGF12), Fibroblast growth factor 13 (FGF13), Fibroblast growth factor 14 (FGF14), Fibroblast growth factor 15 (FGF15), Fibroblast growth factor 16 (FGF16), Fibroblast growth factor 17 (FGF17), Fibroblast growth factor 18 (FGF18), Fibroblast growth factor 19 (FGF19), Fibroblast growth factor 20 (FGF20), Fibroblast growth factor 21 (FGF21), Fibroblast growth factor 22 (FGF22), Fibroblast growth factor 23 (FGF23), Fetal Bovine Somatotropin (FBS), Glial cell line-derived neurotrophic factor (GDNF), Neurturin, Persephin, Artemin, Growth differentiation factor-9 (GDF9), Hepatocyte growth factor (HGF), Hepatoma-derived growth factor (HDGF), Insulin, Insulin-like growth factor-1 (IGF-1), Insulin-like growth factor-2 (IGF-2), Keratinocyte growth factor (KGF), Migration-stimulating factor (MSF), Macrophage-stimulating protein (MSP), Myostatin (GDF-8), Neuregulin 1 (NRG1), Neuregulin 2 (NRG2), Neuregulin 3 (NRG3), Neuregulin 4 (NRG4), Brain-derived neurotrophic factor (BDNF), Nerve growth factor (NGF), Neurotrophin-3 (NT-3), Neurotrophin-4 (NT-4), Placental growth factor (PGF), Platelet-derived growth factor (PDGF), Renalase (RNLS), T-cell growth factor (TCGF), Thrombopoietin (TPO), Transforming growth factor alpha (TGF-α), Transforming growth factor beta (TGF-β), Tumor necrosis factor-alpha (TNF-α), Vascular endothelial growth factor (VEGF), antibodies, or peptide based inhibitors.

A therapeutic molecule may be an RNA. In some embodiments, the therapeutic molecule is a non-coding RNA (i.e., does not code for a protein). For example, in some embodiments the therapeutic molecule is a rRNA, tRNA, tmRNA, snRNA, snoRNA, scaRNA, gRNA, RNase P, RNase MRP, antisense RNA, crRNA, lncRNA, miRNA, piRNA, siRNA, or shRNA. Other forms of non-coding RNA are known to those having skill in the art. In some embodiments, a therapeutic molecule is an mRNA.

A product of interest may be a reporter protein, such as a fluorescent protein. Non-limiting exemplary reporter proteins can be wt-GFP, green fluorescent protein (e.g., EGFP, Emerald, Superfolder GFP, Azami Green, mWasabi, TagGFP, TurboGFP, AcGFP, ZsGreen, T-Sapphire, etc.), blue fluorescent protein, (e.g., EBFP, EBFP2, Azurite, mTagBFP, etc.), cyan fluorescent protein (e.g., ECFP, mECFP, Cerulean, mTurquoise, CyPet, AmCyan1, Midori-Ishi Cyan, TagCFP, mTFP1 (Teal), etc.), yellow fluorescent protein (e.g., EYFP, Topaz, Venus, mCitrine, YPet, TagYFP, PhiYFP, ZsYellow1, mBanana, etc.), orange fluorescent protein (e.g., Kusabira Orange, Kusabira Orange2, mOrange, mOrange2, dTomato, dTomato-Tandem, TagRFP, TagRFP-T, DsRed, DsRed2, DsRed-Express (T1), DsRed-Monomer, mTangerine, etc.), or red fluorescent protein (e.g., mRuby, mApple, mStrawberry, AsRed2, mRFP1, JRed, mCherry, HcRed1, mRaspberry, dKeima-Tandem, HcRed-Tandem, mPlum, AQ143, etc.), luciferase, or b-galactosidase.

In some embodiments, the method comprises contacting a cell with a polynucleotide comprising a polynucleotide sequence encoding a product of interest, wherein the sequence encoding the product of interest is operably linked to a synthetic 5' UTR sequence (and optionally a promoter sequence), thereby introducing the polynucleotide comprising the polynucleotide sequence encoding the product of interest into the cell. The cell may be contacted in vitro or in vivo.

EXAMPLES

Example 1. High-Throughput Untranslated Region Engineering and Screening

Introduction

Biological targets or drug targets are mostly proteins or nucleic acids, whose activity can be modified when interacting with a drug. Although a number of drug targets have been identified via experimental or computational methods, only a small portion of them (about 20%) are actually "druggable" (1, 3). Classical small-molecule drugs can penetrate the cell membrane—and can target not only cell surface targets, but also intracellular targets. However, due to their small molecular weights and few functional groups, small-molecule drugs can only interact with drug targets with hydrophobic pockets, which account for only 10% of the total putative drug targets (43-46). Another emerging type of drug, biologics, can instead potentially interact with virtually any drug target. However, biologics cannot penetrate the cell membrane—and thus can only interact with extracellular targets, which account for another 10% of the total putative drug targets (46-48). Therefore, the two major existing drugs can be used for only 20% of the total putative drug targets, leaving 80% of the targets "undruggable". Moreover, drugs mostly downregulate the activities of the target proteins, especially in the case of intracellular targets.

Recently, several efforts have been done to implement in vivo production of therapeutics to explore the therapeutic potential of targeting "undruggable" targets and restoring the activities of the undermined intracellular proteins. Gene therapies typically rely on adeno-associated virus (AAV) or lentivirus infection, which are efficient in delivery and expression, but generally considered much riskier than traditional drugs, because the foreign DNAs might integrate into critical positions of the genome, resulting in adverse side effects such as inflammation or cancer (49). In contrast, the delivery of mRNAs into cells has recently attracted attention due to their enhanced delivery efficiency and safety (50). However, the costs of mRNA manufacturing are much higher, and additional efforts are needed to address various issues such as mRNA intracellular stability, size limitations, low expression levels, and short expression durations. To overcome these limitations (e.g., to increase safety, payload, stability, and versatility of genetic elements capable of executing complex functions), direct delivery of DNA plasmids was used herein (51, 52).

Others have developed plasmid constructs with high protein expression levels and improved safety, whose design is consistent with the Food and Drug Administration (FDA) document (42). The plasmid used in this study contains a human CMV promoter for high-level protein expression, a multiple clonal site (MCS) for foreign gene insertion, and a bovine growth hormone polyadenylation signal for transcriptional termination. It allows the insertion of the 5' untranslated region (5' UTR), coding sequence, and 3' untranslated region (3'UTR) into the MCS for protein expression.

Protein expression is comprised of two steps: in the first step, DNA is transcribed into mRNA, and in the second step mRNA is translated into protein. Unlike prokaryotic cells, transcription and translation are uncoupled in eukaryotic cells. Protein expression levels are highly dependent on transcript levels (which is governed by the transcription machinery) and translation efficiency of the transcripts (which is governed by the translation machinery) (25, 26). Thus, given an identical transcription rate of two transcripts, the differences in the final amount of protein are mainly determined by features found in the 5' UTR sequences, which will dictate the recruitment of ribosomes for its proper translation.

As described herein, a comprehensive strategy was developed to identify novel 5' UTR sequences that can enhance protein expression from a human CMV promoter. A library of 12,000 5' UTR sequences was designed based on genomic searches and in silico computations. Screening strategies were then developed to screen the library in human rhabdomyosarcoma cells (RD cells). Next-generation sequencing (NGS) analysis methods were also developed that allow one to investigate the correlation between 5' UTR sequences and protein expression. The top 5' UTR candidate sequences are then experimentally validated in RD cells.

Library Design

To identify 5' UTR sequences having a high translational efficiency (TE), a library was built consisting of: i) endogenous 5' UTR sequences extracted from the human genome; and ii) synthetic 5' UTR sequences from computational models, previously trained on endogenous sequences (FIG. 1).

To select the endogenous sequences, publicly available matched RNA-Seq and Ribo-Seq datasets were used, from three different human cell lines/tissues, which included: human embryonic kidney 293 (HEK293) cells, human prostate cancer (PC3) cells, and human muscle tissue. The RNA-Seq and Ribo-Seq datasets were then analyzed to determine translation efficiency rates and mRNA levels. TE was defined as Ribo-Seq RPKM/RNA-Seq RPKM, where RPKM represents Reads Per Kilobase of transcript per Million mapped reads. Transcripts with insufficient RNA-Seq or Ribo-Seq coverage were discarded. The final selection of endogenous 5' UTR sequences consisted of:
i) the top 2000 sequences and bottom 1000 sequences from transcripts with highest and lowest TE from human embryotic kidney 293 (HEK293) cells;
ii) the top-2000 and bottom-1000 sequences from transcripts with highest and lowest TE from human prostate cancer (PC3) cells;
iii) the top 1015 sequences from transcripts that displayed maximum TE for muscle tissue;
iv) transcripts with highest mRNA expression levels in muscle tissue, using the data from Genotype-Tissue Expression (GTEx) project, which was based on the RPKM filtering schemes and corresponded to 1693 sequences.

As a second approach, to further explore the potential of the effects of 5' UTR sequences on protein expression, synthetic sequences were included, which may maximize the translation efficiency of transcripts. For this aim, a computational model was designed and trained to predict the TE based on 5' UTR sequence characteristics (or features). To establish this model, sequence features of 5' UTR sequences corresponding to mRNAs with increased gene expression levels and TE were identified. These sequence features included k-mer frequency, codon usage, RNA folding energy, 5' UTR length, and number of ORFs. The computational model was trained on sequence features to predict translation efficiency and mRNA expression on different cell conditions. The model was trained on experimentally determined translation efficiency rates and mRNA levels, which were obtained from analyzing publically available RNA-Seq and Ribo-Seq data of endogenous genes from three human cell types: HEK293 cells, PC3 cells, and human muscle tissue.

The workflow consisted of the following steps:
  i) extracting sequence features from the 5' UTR sequences, including those nucleotides surrounding the AUG region, i.e., the whole 5' UTR+15bp of the CDS sequences, for each of the expressed transcripts in each cell line or tissue;
  ii) training a Random Forest machine learning method for each cell type/tissue (55), to learn a function that maps sequence features to mRNA expression and TE;
  iii) designing a set of 100-bp synthetic sequences that maximize TE and protein expression (where protein expression is computed as RNA levels*TE)—Given that searching for all $4^{100}$ possible 100-bp sequences would be too computationally demanding, we applied a genetic algorithm (GA) (32), which simulates the evolution process, to search the optimal sequences by mutating and recombining the endogenous sequences. For each GA run, we randomly sampled 100 endogenous 5' UTR sequences as "initial population" prior to undergoing evolution, and selecting them or their offspring based on their fitness, which is defined by their TE or protein expression from the previous trained model;
  iv) from the GA results, the top 5 sequences with at least 5 bp differences in each run were selected;
  v) validate the accuracy of the model, by selecting sequences with a small number of mutations relative to its endogenous origin, but large increase/decrease of TE or RNA expression comparing to its endogenous sequence.

Overall, a total of 3586 synthetic sequences were selected for oligo synthesis through 100 GA runs per cell line/tissue, and per TE and protein expression dataset.

Lentiviral-Based Screening

Lentiviral-based library screening is the most commonly used method for the screening of cis- and trans-genetic elements. The library is cloned to a lentiviral carrier plasmid and transfected into HEK-293 cells with packaging and envelope plasmids to produce lentiviral library, which is then infected into the cells of interest. A multiplicity of infection (MOI) of 0.1 to 0.3 is widely used to ensure most of the infected cells with only one copy of the element of interest. However, even at 0.1 MOI, 10% of cells receive two or more copies. Moreover, the lentivirus inserts the element of interest to random positions on the cell genome, which results in anomalies due to position effects (39, 41). Therefore, the phenotype of the cell depends not only on the effect of the genetic element itself, but also its position and copy number on the genome. If the combination of the copy number effect and position effect is close to or surpass the differences between the genetic element library, the selection is likely to fail.

To eliminate the position and copy number effects, two different strategies were developed: i) co-expressing a second reporter under a constitutive promoter within the same lentiviral construct; and ii) increasing the library coverage in a single reporter system. In the two-reporter system, a truncated version of CMV promoter was also constructed to extend the expression range of the protein, which is weaker than the full-length CMV promoter.
  i) EF1alpha-RFP and truncated CMV-library-GFP: The construct of EF1alpha-RFP and truncated CMV-library-GFP was inserted between 5'LTR and WPRE on pFUGW plasmid to make the backbone of the lentiviral expression plasmid. The lentiviral particles were produced in HEK-293 cells and infected RD cells with low MOIs. Cells of high GFP/RFP ratios were harvested via fluorescence-activated cell sorting (FACS). Genomic DNA was then extracted, and 5' UTR sequences were amplified for NGS sequencing (FIG. 2).
  ii) EF1alpha-RFP and full-length CMV-library-GFP: The lentiviral particles were produced in HEK293 cells and infected RD cells with low MOIs. Cells of high GFP expression were harvested via FACS. Genomic DNA was then extracted, and 5' UTR sequences were amplified for NGS sequencing.
  iii) Full-length CMV-library-GFP: The lentiviral particles will be produced in HEK-293 cells and infect RD cells with low MOIs. Cells of high GFP expression were harvested via FACS. Genomic DNA was then extracted, and 5' UTR sequences were amplified for NGS sequencing.

Figure 2:
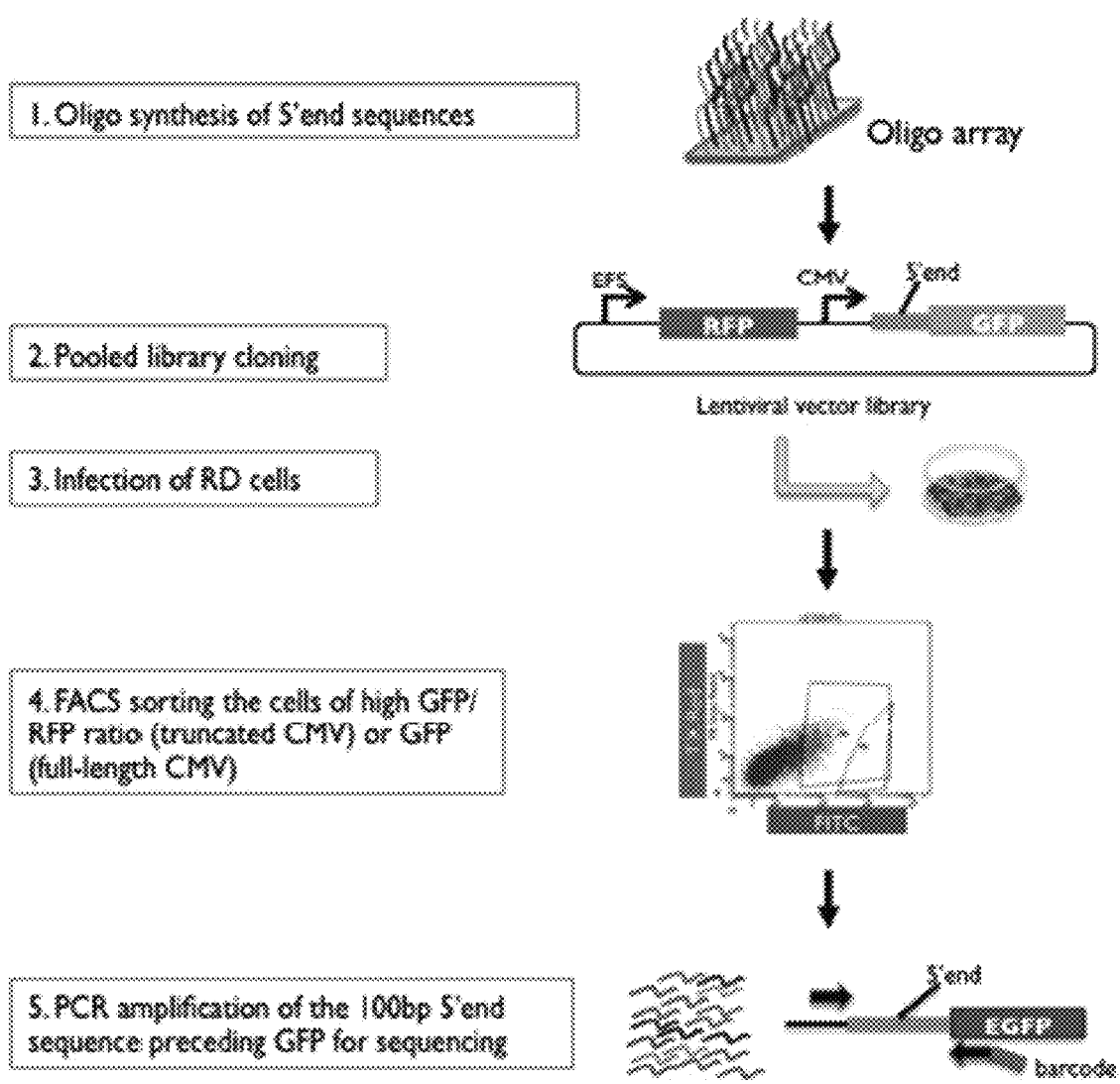
FIG. 2. Schematic depicting a procedure for lentiviral-based screening.

Conventional library-based screening was performed with the 5' UTR sequence library, and as predicted, the reproducibility was too low to select candidates (FIG. 2).

Screening Via Recombinase-Based Gene Integration

Figure 3A:
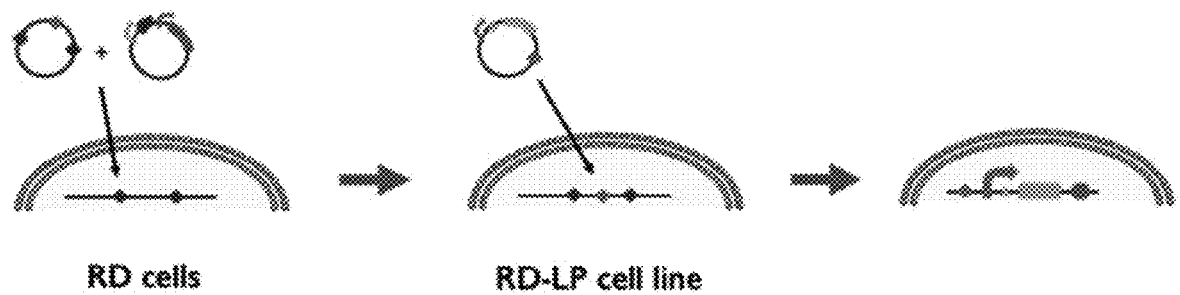
FIGS. 3A-3B. Schematic depicting a procedure for screening via recombinase-based gene integration.
Figure 3B:
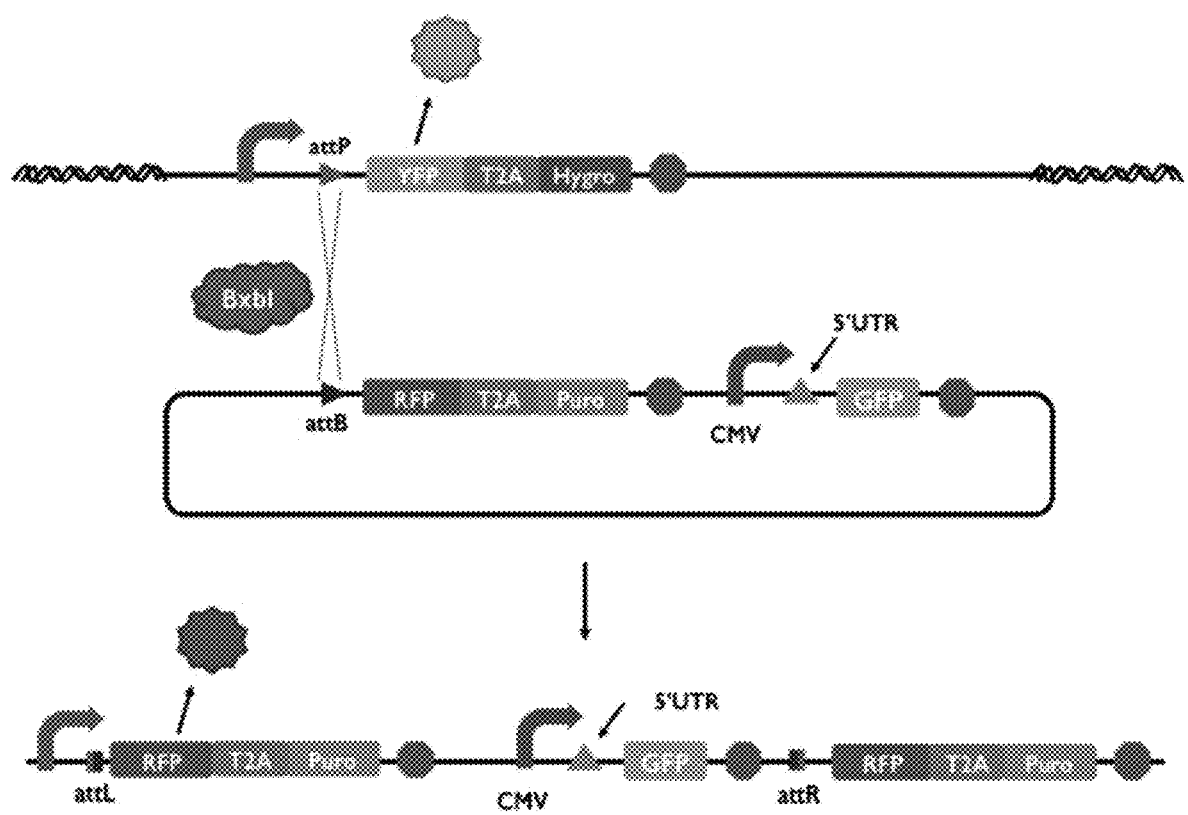

To address this issue, a new method was developed to screen the 5' UTR sequence libraries using recombinase-based gene integration. The serine recombinase Bxb1 recognizes Bxb1 attP sites in the genome and Bxb1 attB sites in the plasmid carrying the payload and inserts the whole plasmid into the Bxb1 attP site while destroying the Bxb1 attP site to prevent additional insertion—thus ensuring the insertion of a single copy of genetic element into the same position in all cells and eliminating the position and gene copy number effects (FIGS. 3A-3B).

Cell lines were constructed with a landing pad by lentiviral infection. The landing pad is a DNA fragment consisting of a constitutive promoter, a mutant BxbI attP site with enhanced integration efficiency and a yellow fluorescent protein (YFP). Nine cell clones were sorted, while two of them with different YFP expression levels were used for library screening. The 12K synthetic 5' UTR sequence library was cloned to the payload plasmid consisting of a BxB1 attB site and an RFP and puromycin duo selection marker. The library was the transfected to the parental cells with landing pads. When the payload plasmid was inserted to the cell genome, the expression of RFP and puromycin was activated, while the expression of YFP was repressed. To ensure the a high-quality of library screening with high-coverage, >24-fold more cells with integration than the size of the library were used. The transfected cells were grown for one week, then subjected to puromycin selection for another 4 days. The selected cells were sorted into different bins of top 2.5%, 2.5-5%, 5-10%, and 0-100% using flow cytometry.

Genomic DNA was then extracted from the cells from the different pools. PCR conditions were optimized for amplicon amplification for unbiased amplification. The amplicons were then barcoded and sequenced using Illumina NextSeq platform.

NGS Data Analysis Fitting of UTR Scores With NGS Data and Candidate Selection

Figure 4:
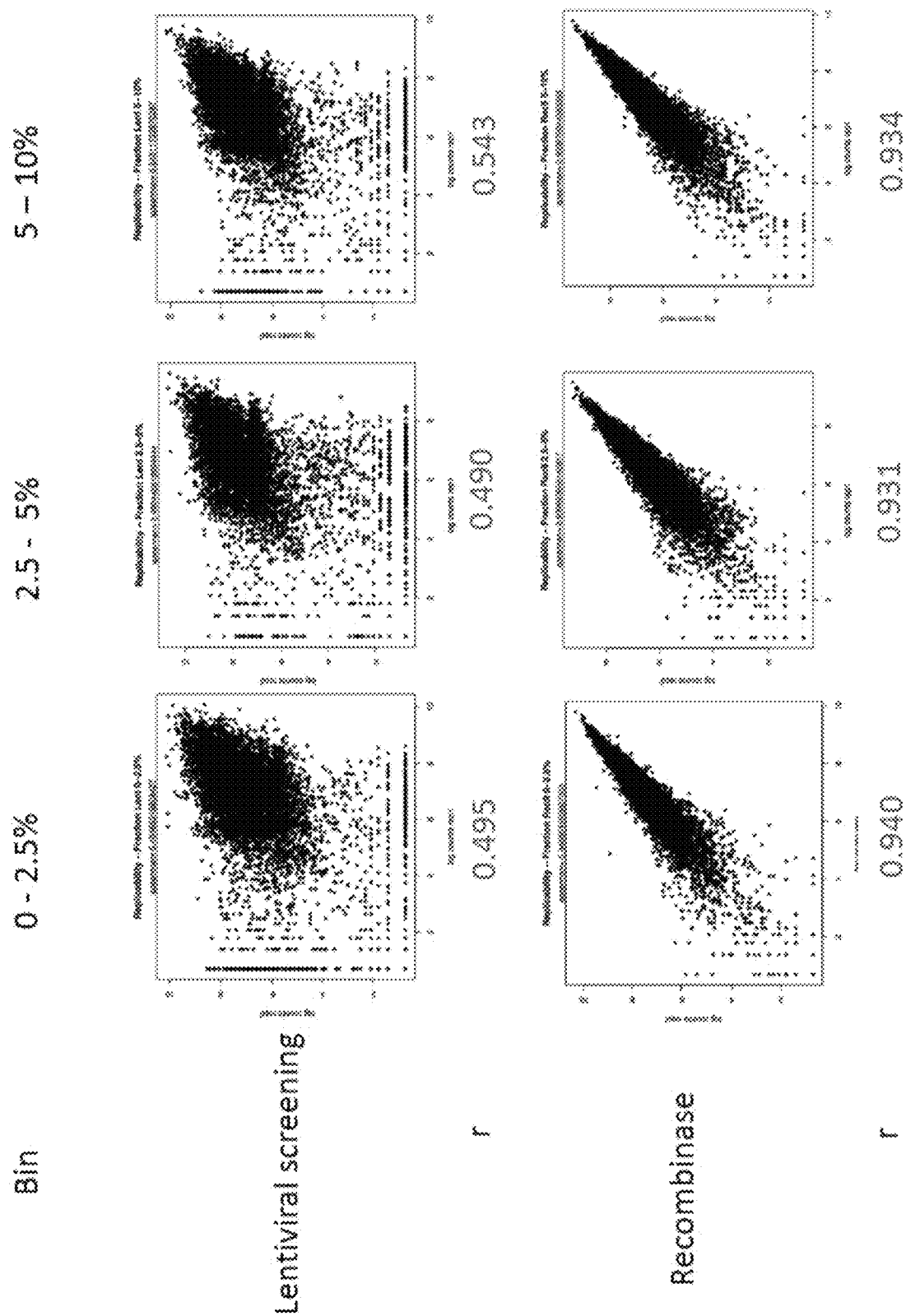
FIG. 4. Recombinase-based library screening showed higher reproducibility.

Fastq reads were trimmed to remove their adaptor sequences (AACTTAAGCTTGGTACCG (SEQ ID NO: 6)

and CTCGCCCTTGCTCACCATGGTGGC) (SEQ ID NO: 7) using Cutadapt v1.21 in a paired-end mode, and with the flag-nextseq-trim, which allows for NextSeq-specific quality trimming. The quality of the trimmed reads was verified using FastQC. Trimmed reads were mapped against the 12K fasta sequences, using Bowtie2. Count occurrences were counted from SAM files using an in-house script. The matrix of counts was normalized using rlog transformation, and the different pools (0-2.5%, 2.5-5%, 5-10%) were analyzed for differential expression using the DESeq2 package in R, relative to the total pool (0-100%). As predicted, the recombinase-based library screening had a much higher r value than that of traditional lentiviral-based library screening (FIG. 4).

Figure 5:
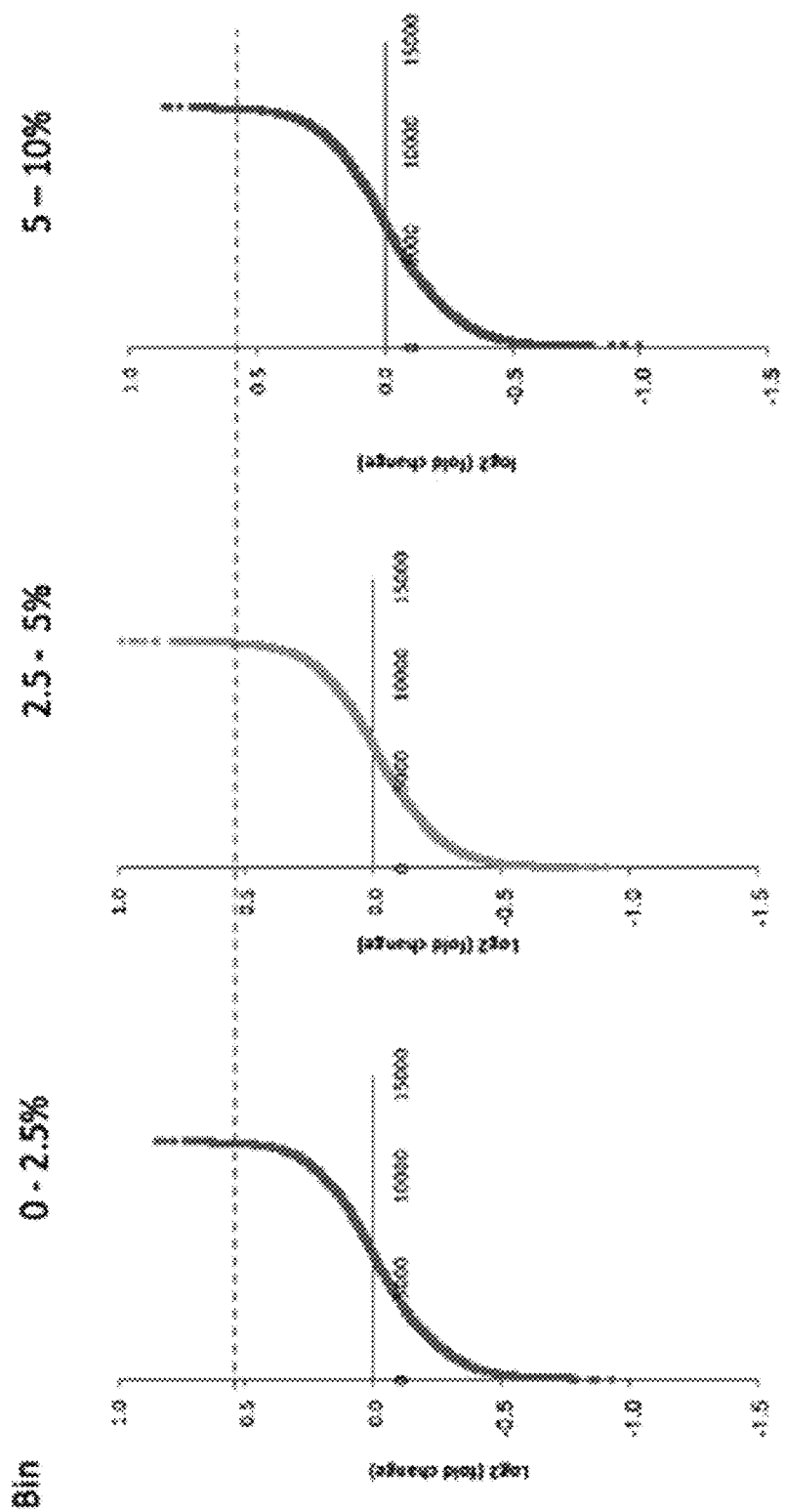
FIG. 5. Selection of the candidates with criteria of $\log_2$ (fold change)>0.52 while P<0.05 in all three bins.

Candidate 5' UTR sequences were selected with the following criteria: $\log_2$ (fold change) is greater than 0.52, while p value is less than 0.05 in all three bins_(0-2.5%, 2.5-5%, 5-10%). Thirteen 5' UTR candidates were found using this method (FIG. 5).

Figure 6:
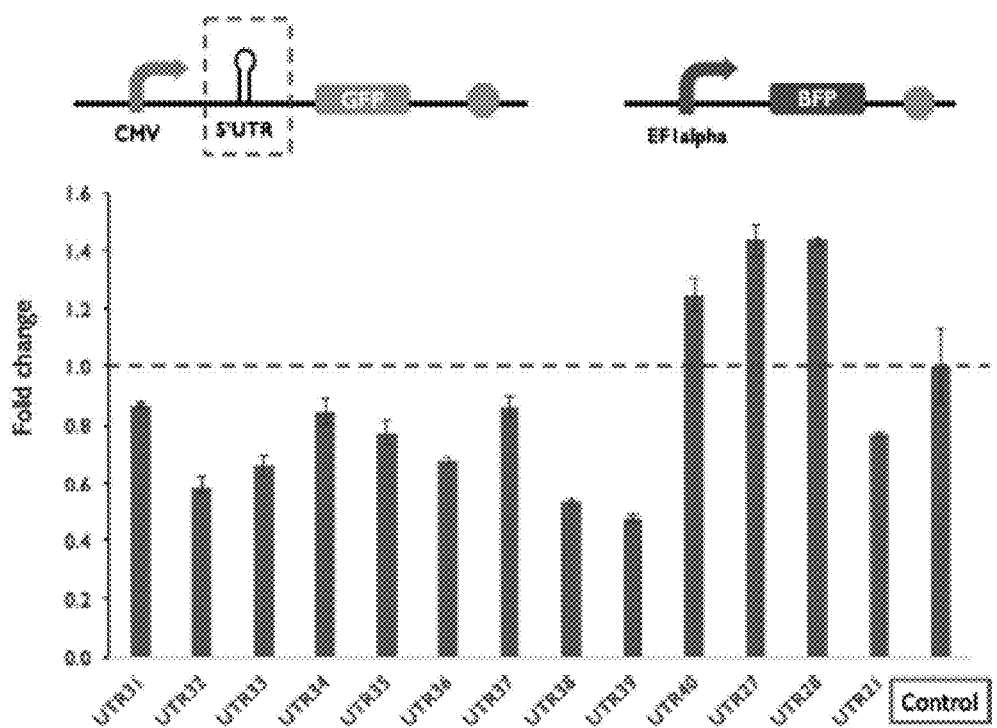
FIG. 6. Validation of 5' UTR candidate sequences, where the GFP reporter is placed in the pVAX1 plasmid, while the cell is co-transfected with a different plasmid expressing a second BFP reporter. UTR40 corresponds to SEQ ID NO: 3; UTR27 corresponds to SEQ ID NO: 1; UTR 28 corresponds to SEQ ID NO: 2.
Figure 8A:
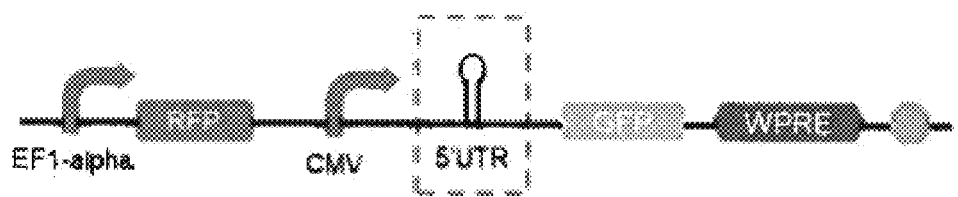
FIGS. 8A-8B. Validation of 5' UTR candidate sequences, where the GFP reporter is placed with a second RFP reporter for normalization, which is on the same plasmid.
Figure 8B:
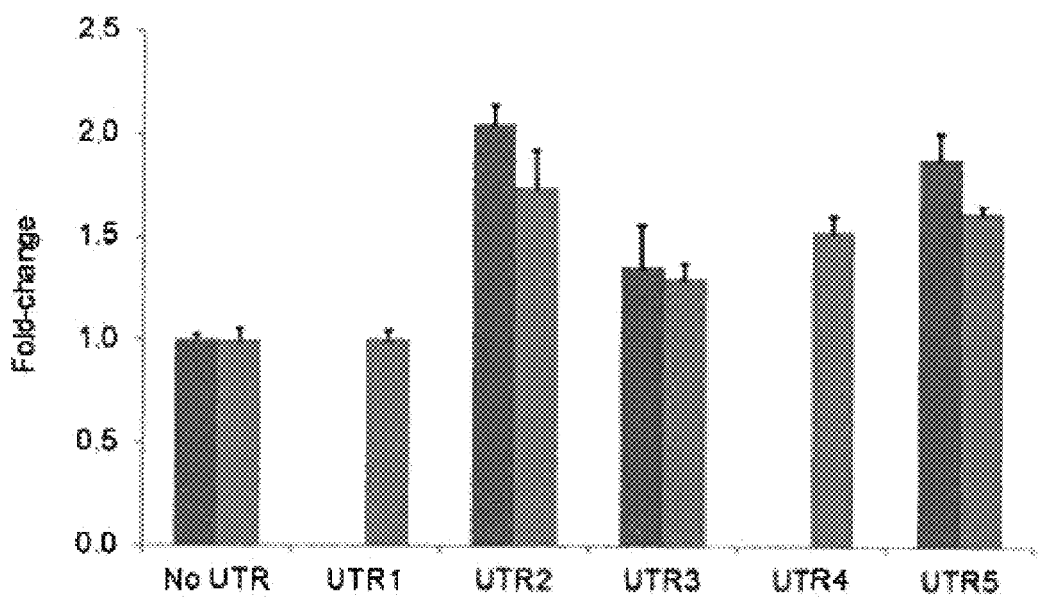
Figure 9A:
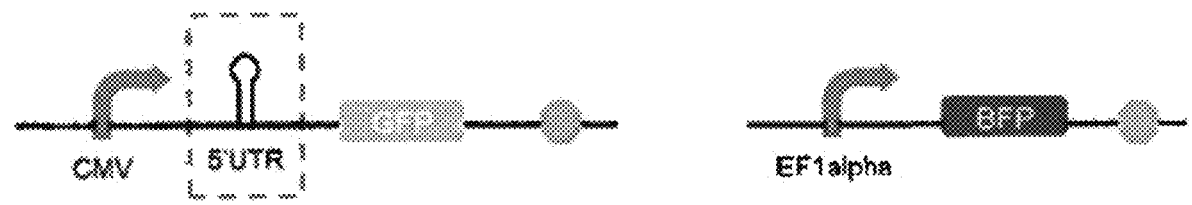
FIGS. 9A-9B. Validation of 5' UTR candidate sequences, where the GFP reporter was placed in the pVAX1 plasmid, while the cells were co-transfected with a different plasmid expressing a second BFP reporter.
Figure 9B:
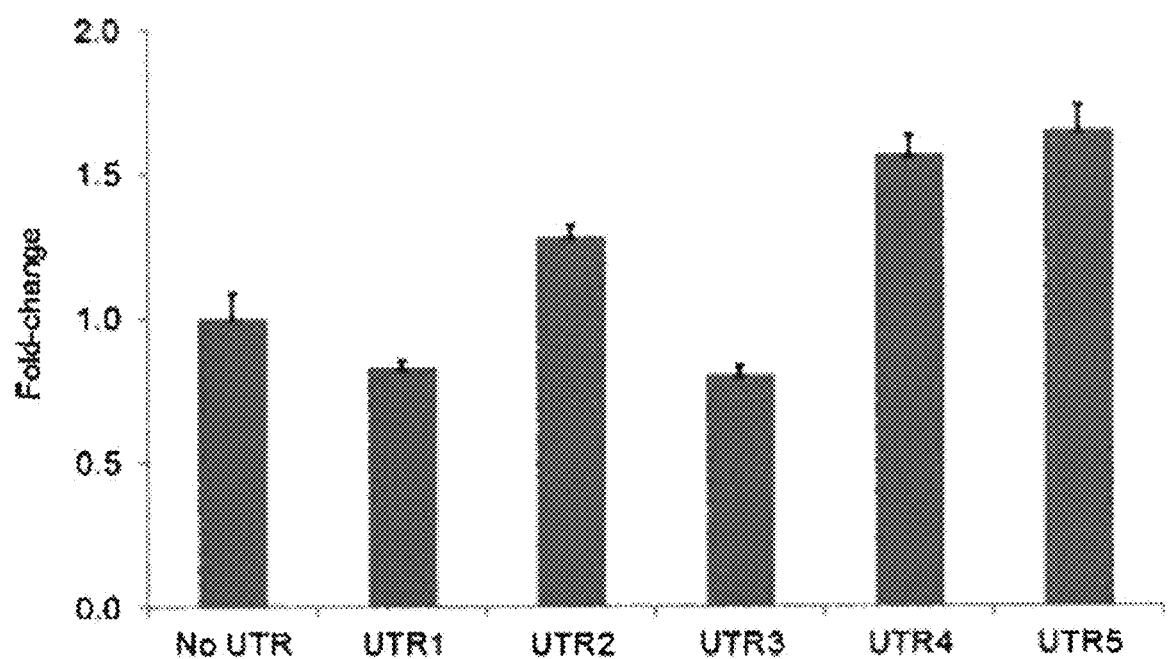
Figure 10A:
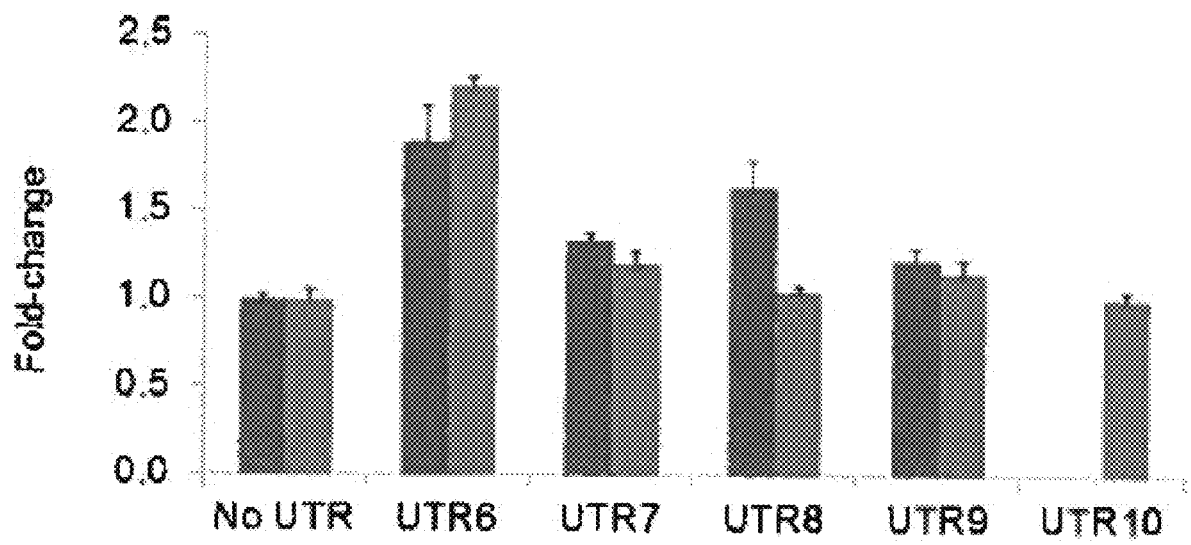
FIGS. 10A-10B. Validation of 5' UTR candidate sequences derived from CHO experiments.
Figure 10B:
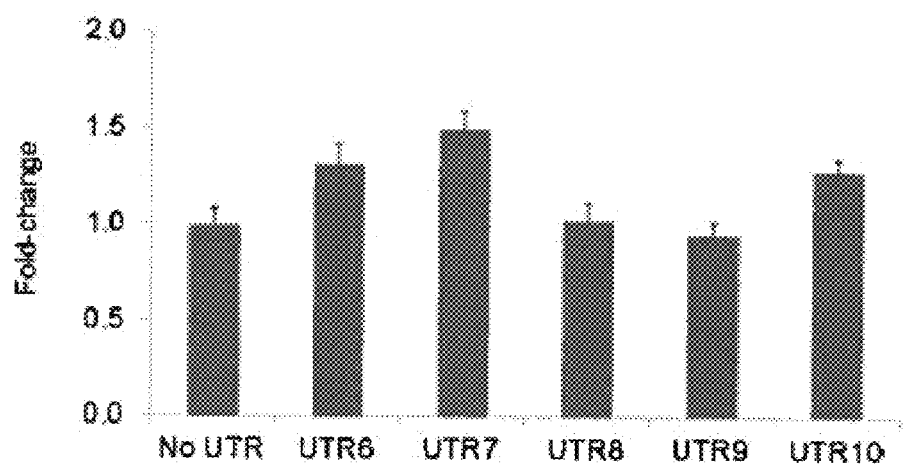

Hits Tested in Different Cell Lines, Comparison With Introns, Combination of UTRs Two methods were designed to validate the effects of the 5' UTR sequences on protein expression: 1) the GFP reporter was placed with a second RFP reporter for normalization, which is on the same plasmid (FIGS. 8A-8B); and ii) the GFP reporter was placed in the pVAX1 plasmid, while co-transfected with a different plasmid expressing a second BFP reporter (FIG. 6 and FIGS. 9A-9B). 5' UTR sequences were also validated in CHO cells. Two candidates showed an increase of 43% in GFP expression compared to the control (FIG. 6).

Figure 7:
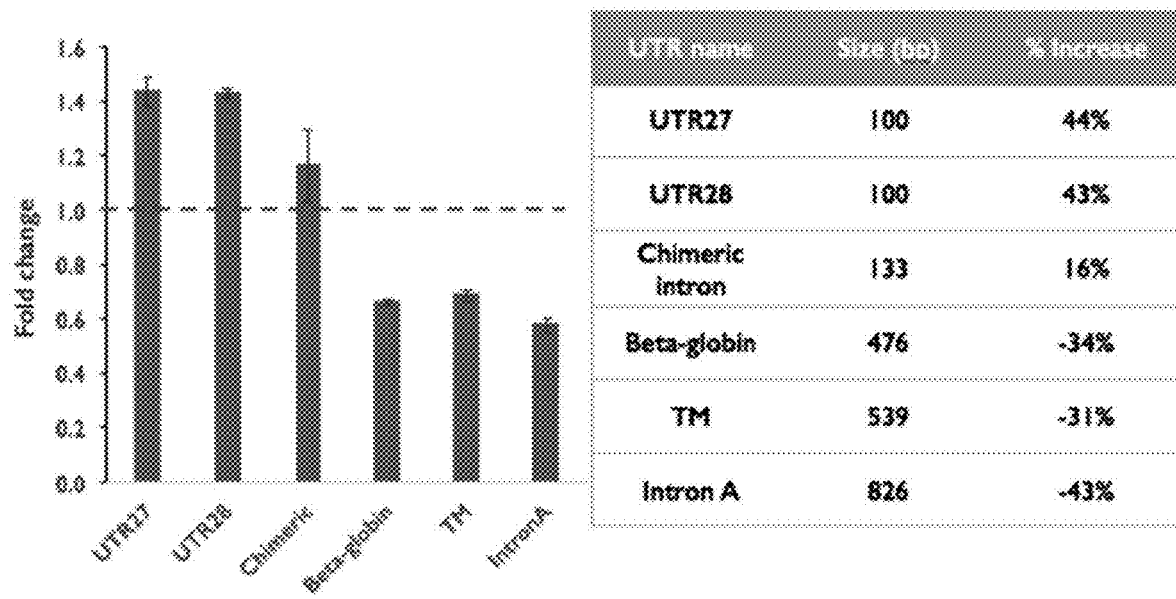
FIG. 7. Comparison of 5' UTR sequences with previously described introns and UTR sequences. UTR27 corresponds to SEQ ID NO: 1; UTR 28 corresponds to SEQ ID NO: 2.

Various 5' UTR sequences were then compared with commonly used introns and previously described 5' UTR sequences. A common method of enhancing gene expression levels is to insert introns at the 5' UTR. Introns can increase RNA export rate and translational efficiency, and thus increase gene expression. Three commonly used introns were compared with the 5' UTR sequences identified herein in RD cells: i) a chimeric intron from pmaxCloning plasmid; ii) the first intron of human CMV immediate early gene (Intron A); and iii) intron 2 of human beta-globin. A 5' UTR sequence found in previous studies that can significantly enhance gene expression in HEK-293 and CHO-K1 cells was also analyzed, which is the tripartite leader sequence of human adenovirus mRNA linked with a major late promoter enhancer (TM) (FIG. 7). The synthetic UTRs identified herein outperformed those four in both size and gene expression enhancement.

Example 2. High-Throughput 5' UTR Engineering for Enhanced Protein Production in Non-Viral Gene Therapy Introduction Most drug targets are proteins whose activities are modified by interactions with drugs. Although a number of drug targets have been identified via experimental or computational methods, only a fraction of them are actually "druggable" with small molecule drugs or monoclonal antibodies (1-3), which greatly limits our arsenal of treatments for important human diseases. Gene therapy, which implements the in vivo production of therapeutics, can address virtually all disease targets and even restore the activities of intracellular proteins.

Non-viral DNA therapy, a disruptive technology using DNA plasmids to produce therapeutic proteins or vaccine antigens in vivo, offers significant advantages over traditional virus-mediated gene therapies (4-6). First, non-viral DNA therapy is potentially safer than lentiviral therapies as the odds of gene integration into the genome are reduced, and it is much less immunogenic (7-9). Second, the drug payload achieved with non-viral DNA delivery can be very large, because multiple genes and even sophisticated genetic circuits can be delivered at the same time into the cells to carry out complex functions, i.e., there is no restriction based on viral packaging requirements. Third, compared with viruses, the plasmids are easy and economical to produce at both the lab and the industrial scale (10), and loss of viral infective potency during manufacturing and storage does not need to be taken into consideration (11).

Although in vivo DNA delivery efficiency has been improved significantly as a result of recent advancements in liposome chemistry and nanoparticle design, only a small number of DNA plasmids can enter the nucleus (12-14). To ensure that drug levels produced in vivo are sufficient, either DNA doses can be increased or transfections can be done repeatedly. Either of these approaches, however, increases costs and time of production. Alternatively, protein expression can be enhanced by optimizing the backbone of the DNA vector. In DNA plasmids, gene expression cassettes consist of five elements: promoter, 5' untranslated region (5' UTR), protein coding region, 3' UTR, and polyadenylation (PolyA) signal (15). Synthetic biology and machine learning offer genetic toolboxes to engineer the non-coding regions for gene expression regulation [REFs]. Of all known naturally occurring and synthetic promoters, the human cytomegalovirus (CMV) promoter permits the most efficient, highest level of expression across a variety of mammalian cell types. The CMV promoter is much shorter than artificial promoters, making it the most commonly used promoter for gene expression in human cells (16, 17). One can gradually reduce gene expression by either truncating the CMV promoter at its 5' end or inserting a hairpin near the 5' cap of the transcript (18, 19). The real challenge for modulating gene expression, then, is how to enhance gene expression.

The rational design of 5' UTR sequences to enhance protein expression remains elusive, even though 5' UTR sequences have been identified that regulate gene expression in certain scenarios (20-24). The design of 5' UTR sequences has been held back by limited knowledge of the relationships between the 5' UTR sequences and protein expression levels. In this study, key features of 5' UTR sequences were identified by exploring a gene expression dataset of naturally occurring 5' UTR sequences to design synthetic 5' UTR sequences whose translation efficiency lies beyond the range of the training set. To efficiently capture and screen the relatively minor differences in expression levels of 5' UTR sequences in the library, a recombinase-based library screening strategy was developed that can eliminate the copy number and position effects commonly seen in traditional lentiviral-based library screening technologies. Various synthetic 5' UTR sequences were identified that outperform natural 5' UTR sequences and 5' UTR sequences of a commercial gene expression plasmid. Combinatorial 5' UTR sequences were found to further enhance gene expression. Moreover, the synthetic 5' UTR sequences disclosed herein enhance protein expression in a variety of cell types; thus, they can be used for non-viral gene therapy.

Data Collection and Analysis, and Library Design

Figure 11A:
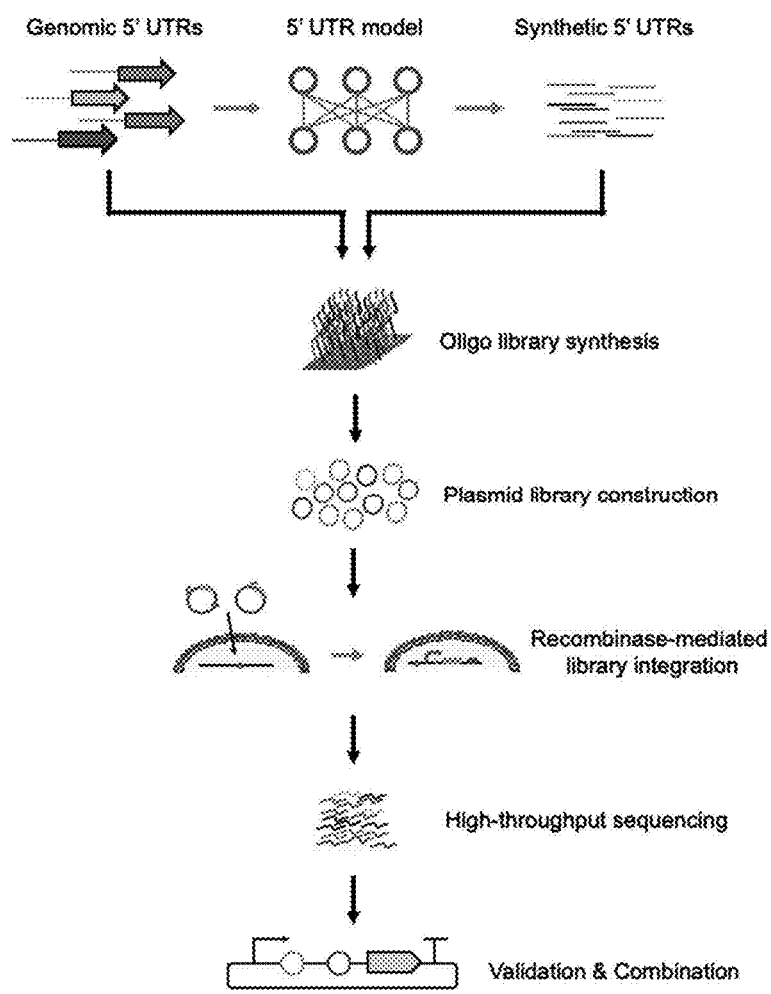
FIGS. 11A-11C. Overview of the strategies developed to design the 5' UTR sequence library.
Figure 11B:
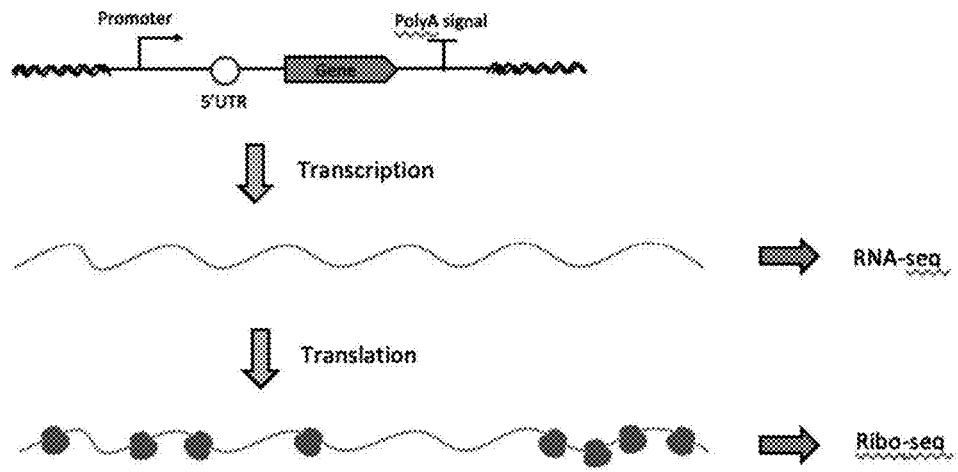

Protein expression comprises two steps: first, DNA is transcribed into mRNA; and second, mRNA is translated into protein. These two steps, transcription and translation, are coupled in prokaryotic cells, but uncoupled in eukaryotic cells. In eukaryotic cells, protein expression levels are highly dependent on mRNA levels, which are governed by the transcription machinery, as well as on the translation efficiency (TE) of the transcripts, which is governed by the translation machinery (25, 26). Thus, given an identical transcription rate for two transcripts, the differences in the final amount of protein are mainly determined by features found in the 5' UTR sequence, which dictate the recruitment of ribosomes for proper translation. Because the TE of a gene is the rate of mRNA translation into protein, it can be calculated as the ratio of the number of copies of ribosomes on the mRNA of interest to the number of the mRNA (FIG. 11B). RNA-Seq can be used to measure the number of mRNA transcripts while Ribo-Seq can be used to measure the number of ribosomes on the mRNAs, to obtain the TE of each gene or a certain RNA fragment.

Figure 11C:
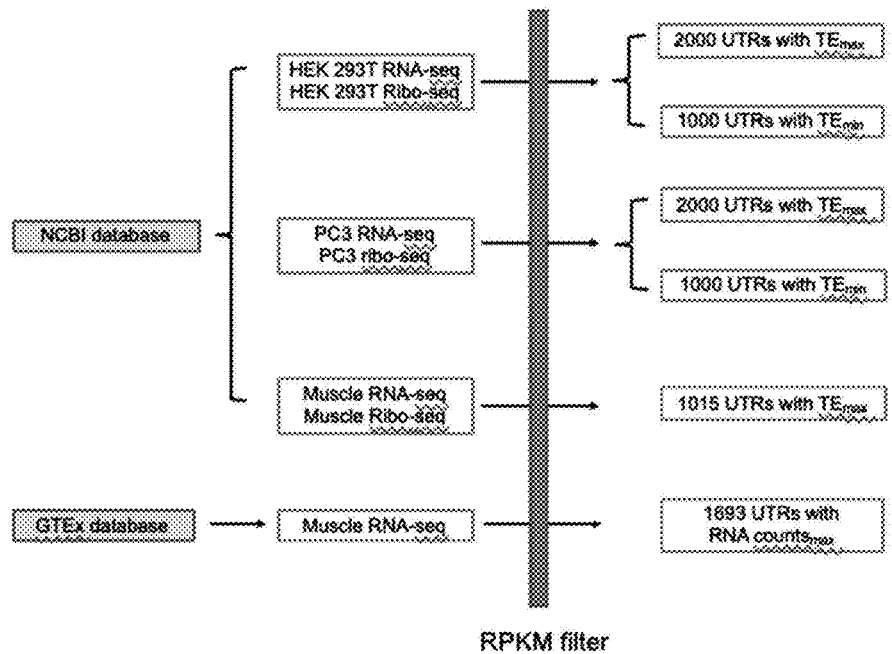

To systematically screen for 5' UTR sequences that enhance protein expression, the effects on translation of naturally occurring 5' UTR sequences was investigated (FIG. 11C). The public datasets of Ribo-seq and RNA-seq of two human cell lines, human embryonic kidney 293T (HEK 293T) (27) and human prostate cancer cell line PC3 (28), were used to compute the TEs of the genes. 5' UTR sequences of 2000 and 1000 transcripts with the highest and lowest TEs were extracted, respectively. As muscle tissue is a common tissue for non-viral gene therapy, such as DNA vaccines and cancer vaccines, 1015 5' UTR sequences with high TEs were also included in the library (29). In addition, based on the Genotype-Tissue Expression (GTEx) database, 1693 5' UTR sequences were extracted from genes with high expression in muscle cells. For 5' UTR sequences that were longer than 100 bp, sequences were extracted from the 5' end and the 3' end; those shorter than 100 bp were filled up with repeats of a CAA motif that does not have known secondary structure to create two versions of sequences (30), one having a shift of one nucleotide relative to the other. All RNA-triplet AUGs were removed by randomly mutating one of the three nucleotides to avoid generating unwanted upstream open reading frames.

Figure 12:
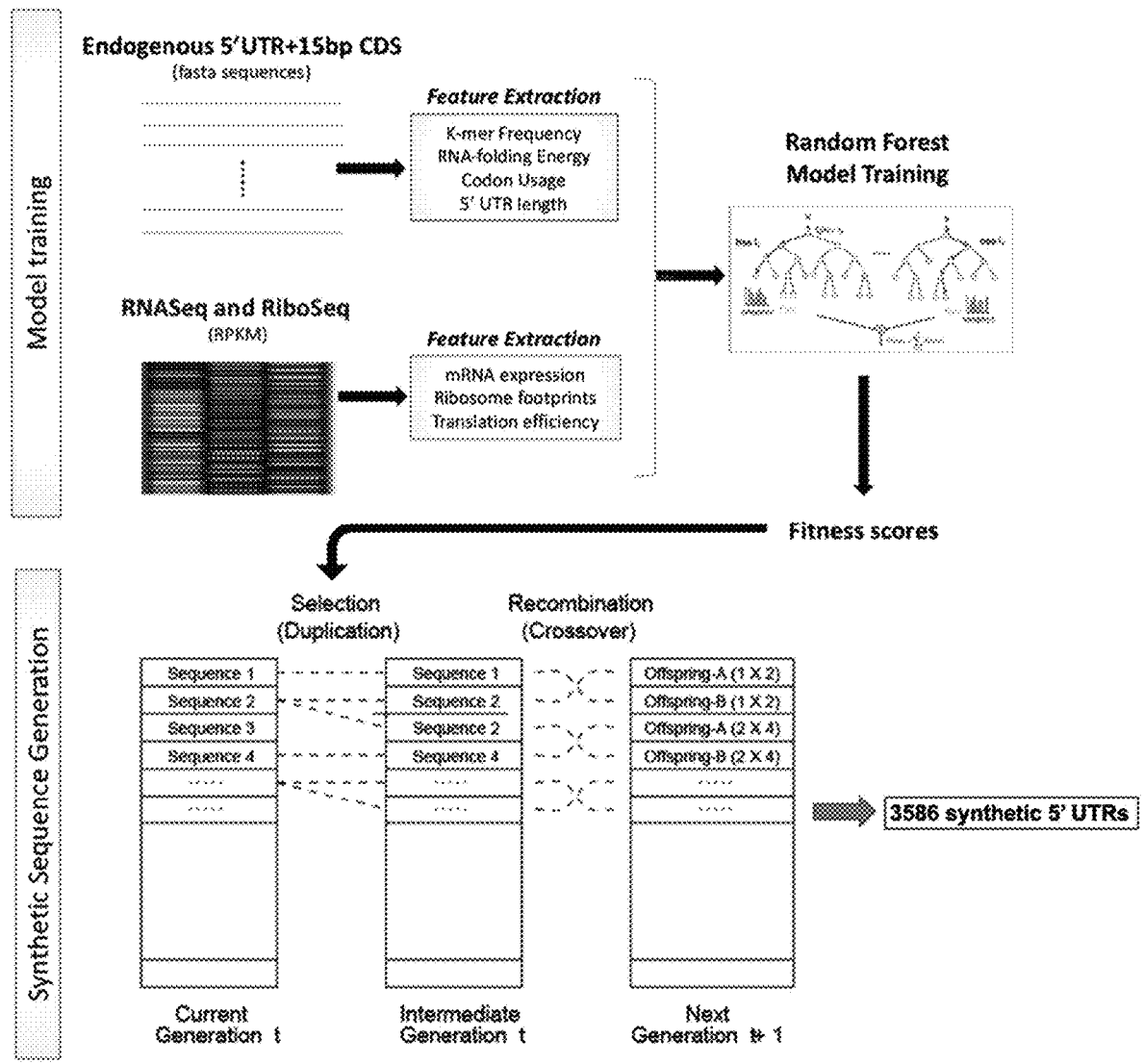
FIG. 12. The machine learning model to calculate translational efficiencies (TEs), which was used to evaluate the effects of the natural-occurring 5' UTR sequences and to predict synthetic 5' UTR sequences.

To further explore the potential of the effects of 5' UTR sequences on protein expression, synthetic sequences were included in in the library, which may maximize the TE of transcripts. For this aim, a computational model was developed and trained to predict the TE based on its 5' UTR characteristics (FIG. 12). To establish this model, sequence features of 5' UTR sequences corresponding to mRNAs with increased gene expression levels and TE were identified. The sequence features investigated included k-mer frequency, codon usage, RNA folding energy, 5' UTR length, and number of ORFs. A computational model trained on sequence features was developed to predict TE and mRNA expression under various cell conditions. The model was trained on experimentally determined TE rates and mRNA levels, which were obtained from analyzing publicly available RNA-Seq and Ribo-Seq data of endogenous genes from three human cell types: HEK-293T cells, PC3 cells, and human muscle tissue (31). Given that searching for all $4^{100}$ possible 100-bp sequences would be too computationally demanding, a genetic algorithm was applied (32), which simulates the evolution process, to search for the optimal sequences by mutating and recombining the endogenous sequences. Overall, a total of 3586 synthetic sequences of 100 bp were selected, and these were combined with the 8414 natural-occurring sequences for the library synthesis in this study.

Recombinase-Based Library Screening

Lentiviral-based library screening is the most commonly used method of genetic screening (33-35). The library is cloned into a lentiviral carrier plasmid and transfected into a virus-producing cell line with packaging and envelope plasmids to produce a lentiviral library, which is then used to infect the cells of interest. A multiplicity of infection (MOI) of 0.1 to 0.3 is widely used to ensure that most of the cells are infected with only one copy of the element of interest. However, even at 0.1 MOI, 10% of the cells receive two or more copies. Moreover, the lentivirus inserts the element of interest at random positions on the cell genome, which may lower gene expression due to position effects (36, 37). Therefore, the phenotype of the cell depends not only on the effect of the genetic element itself, but also on its position in the genome and its copy number in the cell.

Figure 13A:
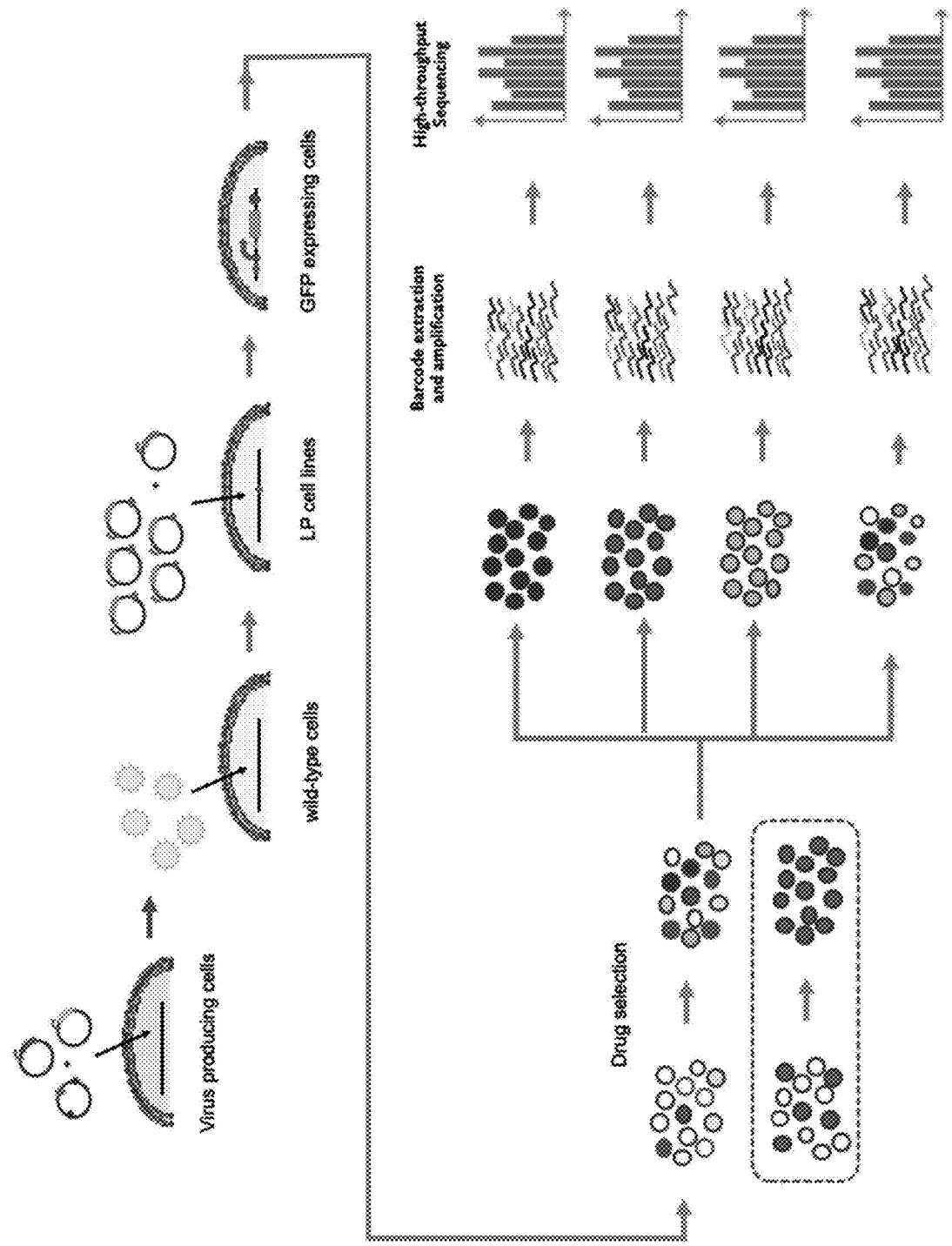
FIGS. 13A-13D. Strategy for constructing cell lines with landing pads and screening the 5' UTR sequence libraries using recombinase-based gene integration.

To address this issue, a new method was developed for screening the 5' UTR sequence library using recombinase-based gene integration (FIG. 13A). The serine recombinase Bxb1 recognizes the Bxb1 attP site in the genome and the Bxb1 attB site in the plasmid carrying the payload; therefore, one can insert the whole plasmid into the Bxb1 attP site in the genome while destroying the Bxb1 attP site to prevent additional insertion (38-41), thus ensuring the insertion of a single copy of the genetic element into the same position in all cells and eliminating the position and gene copy number effects.

Figure 13B:
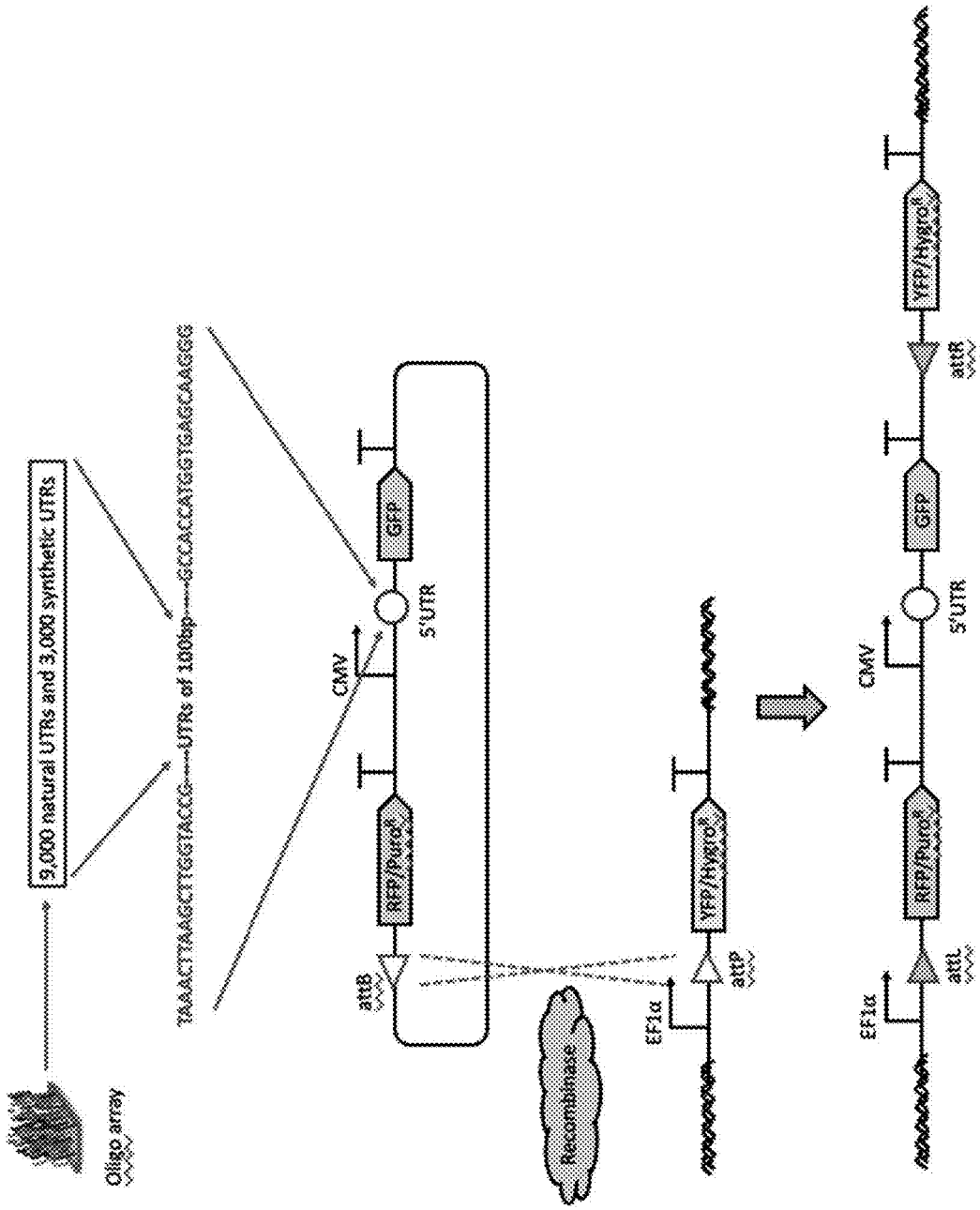

Cell lines were constructed with a landing pad using lentiviral infection. In these cell lines, the landing pad was a DNA fragment consisting of a constitutive promoter, a mutant BxbI attP site with enhanced integration efficiency, and a yellow fluorescent protein (YFP) as reporter (39). Nine cell clones with only one landing pad insertion were identified and expanded. To further reduce the potential interactions between the specific genomic loci and the 5' UTR sequences, two cell lines were chosen with different YFP expression levels as biological replicates for library screening. The library, consisting of 12,000 synthetic 5' UTR sequences, was cloned into the GFP reporter on the payload plasmid consisting of a BxB1 attB site and a red fluorescent protein (RFP) and puromycin duo selection marker (FIG. 13B). The parental cells, which had the landing pad, were then transfected with the library. When the payload plasmid was inserted into the cell genome, the expression of RFP and puromycin was activated while the expression of YFP was repressed. To ensure a high-quality of library screening with high-coverage, >24-fold more cells with integration than the size of the library were used. The transfected cells were grown for one week, then subjected to puromycin selection for another 4 days. Using flow cytometry, the selected cells were sorted into four bins based on GFP expression: top 2.5%, 2.5-5%, 5-10%, and 0-100%. Genomic DNA was then extracted from the different bins, and PCR conditions were optimized for unbiased amplicon amplification. The amplicons were then barcoded and sequenced using Illumina NextSeq platform.

Figure 13C:
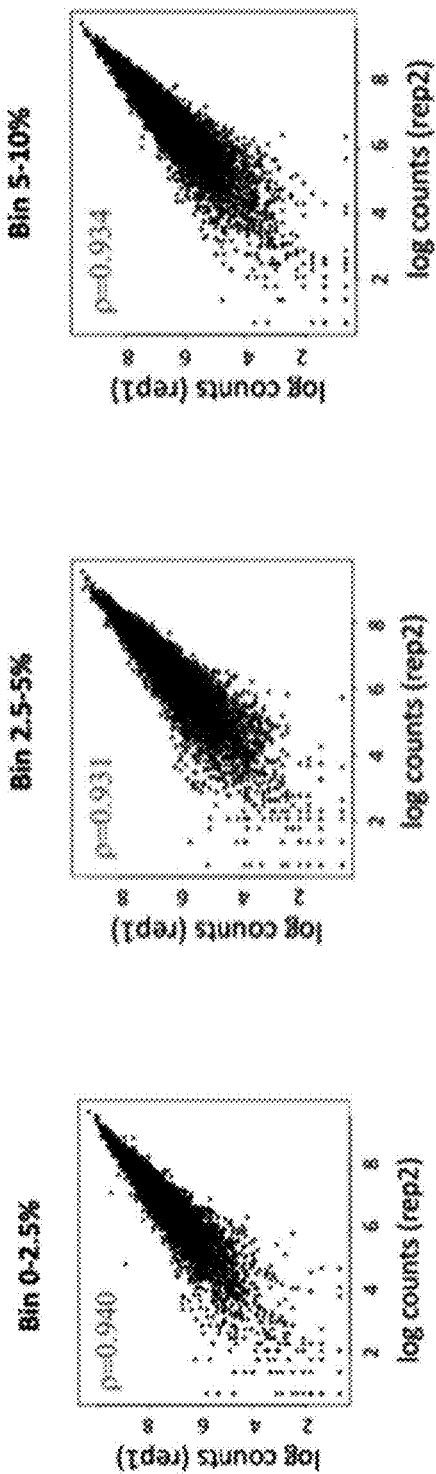

The numbers of the counts of each 5' UTR sequence in the bins of top 2.5%, 2.5-5%, and 5-10% were calculated and normalized to the counts in the control bin, 0-100%. The $\log_2$ ratios were used to represent the enrichment of the 5' UTR sequences in each bin. As proposed, the recombinase-based library screening, which eliminated the copy number and position effects, had r values that were greater than 93% throughout all three bins, indicating high reproducibility of the screening process (FIG. 13C), which was not achieved with traditional lentiviral-based library screening.

Figure 13D:
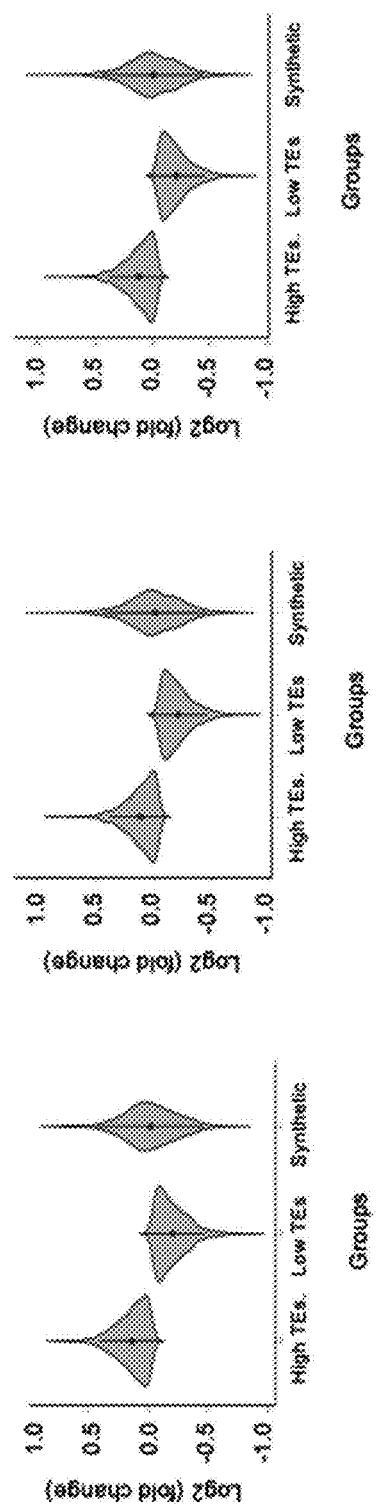

Furthermore, for the natural 5' UTR sequences extracted based on the TEs of the HEK-293T cell line, the mean $\log_2$ ratios of the 5' UTR sequences with high TEs were much higher than those of the 5' UTR sequences with low TEs, which indicates that the new library screening platform can effectively distinguish 5' UTR sequences based on their TEs (FIG. 13D). Interestingly, the mean log₂ ratios of the 5' UTR sequences were smaller than those of the natural ones with high TEs, but displayed a broader range of TEs. Some of the 5' UTR sequences were even better than the natural 5' UTR sequences. These results indicate that the model captures several key features that regulate 5' UTR translation and is able to generate 5' UTR sequences that outperform the ones from the corresponding training set. Thus, overall performance can be improved by an iterative machine learning strategy. It was also found that for the PC3 cell line, the 5' UTR sequences displayed patterns similar to those in HEK-293T cells, but for the muscle tissues, all the same groups looked similar. These observations indicate that cell type may have affect mRNA translation.

Figure 14A:
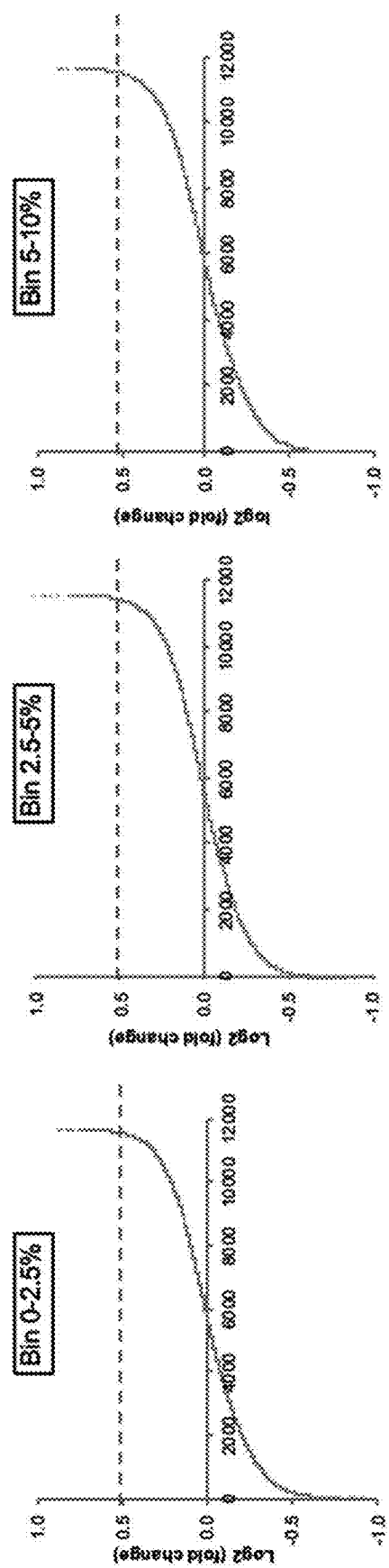
FIGS. 14A-14F. Selection and validation of the 5' UTR candidate sequences from the screening.

Validation of the 5' UTR Hits in HEK-293T Cells and Their Adaptability to Non-Viral DNA Therapy To select candidates for further validation, the 5' UTR sequences were ranked based on their mean log₂ ratios from the two repeats. The top leads were defined as 5' UTR sequences with log₂ ratios that are greater than 0.52 with p values that are less than 0.05 versus control (FIG. 14A). Thirteen 5' UTR sequences that were observed to have log₂ ratios greater than 0.52 in all three bins were used for further validation.

Figure 14B:
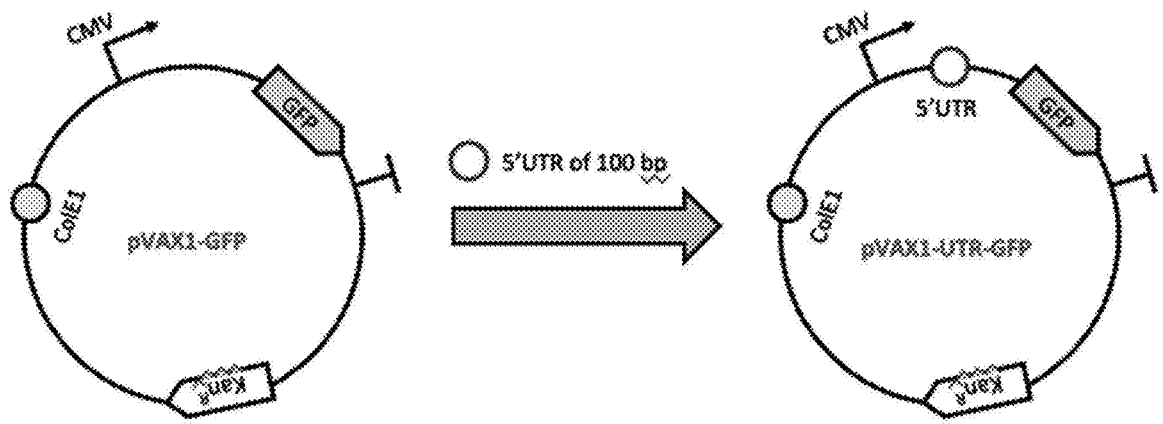
Figure 14C:
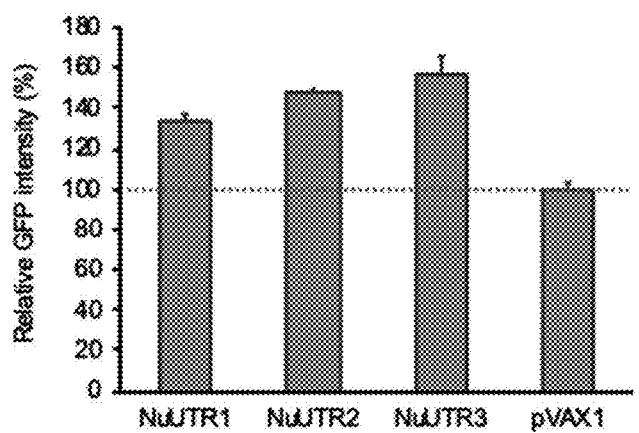

Others have developed DNA plasmid constructs with high protein expression levels and improved safety, whose design is consistent with the Food and Drug Administration (FDA) document (42). The plasmid pVAX1 was considered to be an ideal plasmid for DNA delivery in non-viral gene therapy, because it contains a human CMV promoter for high-level protein expression, a multiple cloning site for foreign gene insertion, and a bovine growth hormone (bGH) polyA signal for transcriptional termination. Candidate 5' UTR sequences of 100 bp and a green fluorescent protein (GFP) reporter (with Kozak sequence) were positioned downstream of the CMV promoter in the pVAX1 plasmid. The GFP only reporter was used as a control (with Kozak sequence; pVAX1-GFP) (FIG. 14B). HEK-293T cells were transfected with a control or an experimental plasmid and a blue fluorescent protein (BFP) expression plasmid to eliminate the noise resulting from transfection efficiency and measured GFP and BFP fluorescence, respectively. Six plasmids showed higher GFP expression than the commercial protein expression plasmid pVAX1 in HEK 293T cells. Of these, three 5' UTR sequences with the very highest GFP expression, which increased the protein abundance of GFP by 37% to 58% (FIG. 14C), were chosen for subsequent study. All three 5' UTR sequences, labeled as NuUTR1 (SEQ ID NO: 2), NuUTR2 (SEQ ID NO: 1), and NuUTR3 (SEQ ID NO: 3), were generated by the machine learning algorithms: NuUTR1 (SEQ ID NO: 2) was generated from the model based on HEK-293T TE; NuUTR2 (SEQ ID NO: 1) was generated from the model based on HEK-293T ribosome abundance; and NuUTR3 (SEQ ID NO: 3) was generated from the model based on PC3 TE. Therefore, even though the 5' UTR sequences generated by the machine learning model do not yield a mean expression higher than that of the best 5' UTR sequences from natural sequences, this model, based on the public databases, does generate some leads that outperform their naturally occurring counterparts.

Figure 14D:
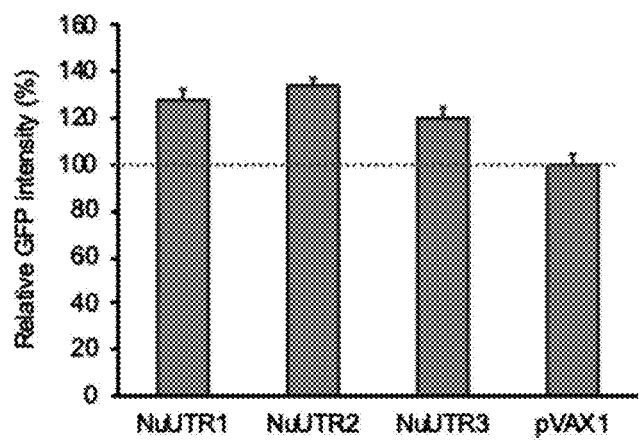
Figure 14E:
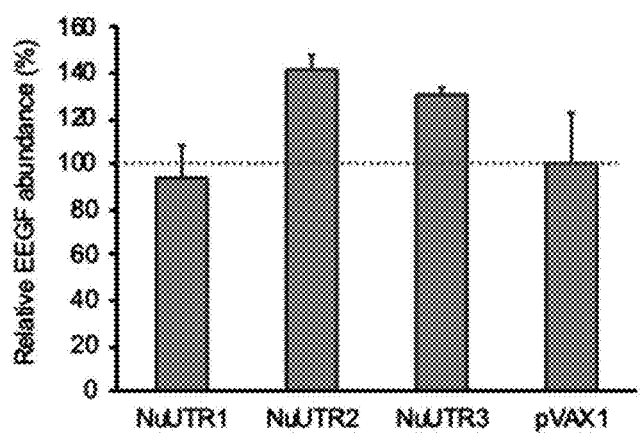
Figure 14F:
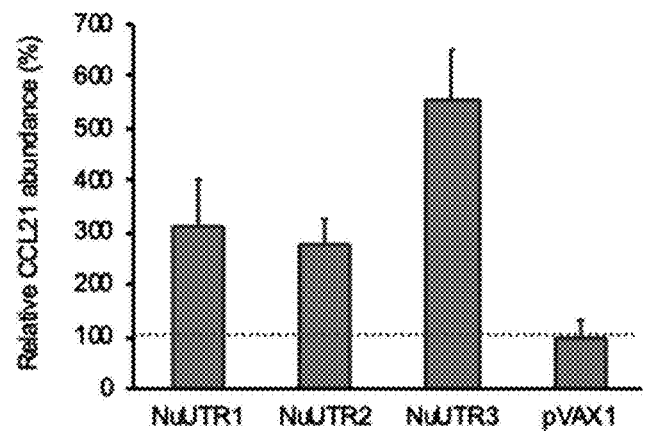

To further evaluate the adaptability of the 5' UTR sequences and their potential to be used as non-viral DNA vectors, their performance in human muscle cells was evaluated. Human rhabdomyosarcoma (RD) cells were chosen, and it was observed that all three 5' UTR sequences enhanced GFP expression in RD cells, as well (FIG. 14D). Next, two therapeutic proteins used in gene therapy were used to evaluate the 5' UTR sequences: vascular endothelial growth factor (VEGF), which stimulates the formation of blood vessels; and C-C motif chemokine ligand 21 (CCL21), which enhances the immune response in cancer therapy. Two of the three 5' UTR sequences increased VEGF expression compared to the commercial plasmid, and NuUTR2 (SEQ ID NO: 1) increased VEGF production by 42% (FIG. 14E), while all three 5' UTR sequences increased CCL21 expression by greater than 100%, and NuUTR3 (SEQ ID NO: 3) showed an impressive increase of 452% (FIG. 14F). These results demonstrate the versatility of the 5' UTR sequences identified in screening and the ability of the 5' UTR sequences to increase therapeutic protein expression to high levels.

Combining the 5' UTR Sequences can Further Enhance GFP Expression

Figure 15A:
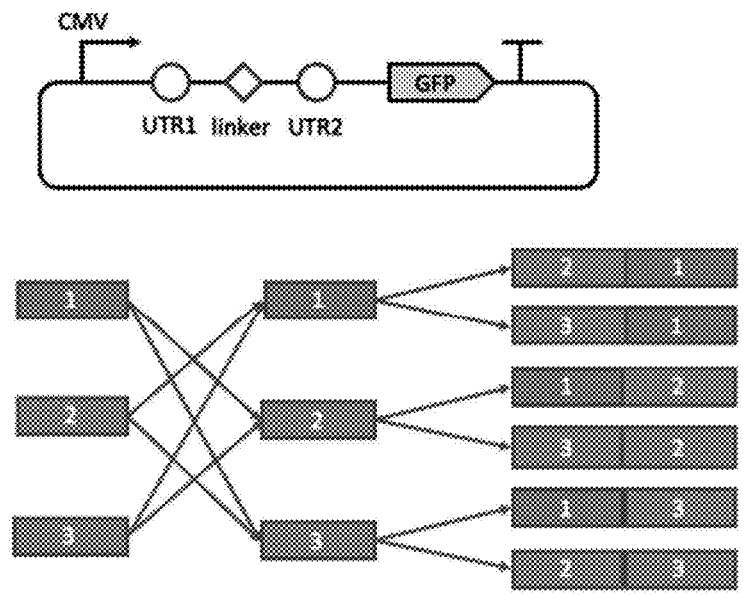
FIGS. 15A-15C. Construction of combinatorial 5' UTR sequences and study of their effects on GFP expression in various cell lines.

These 5' UTR sequences described herein can be used not only to express a fluorescent protein, but also to enhance the expression of therapeutic proteins. One strategy to improve the constructs is to re-train the models with the next generation sequencing (NGS) data, predict new constructs, and repeat the screening (23). To avoid this laborious and time-consuming process, combinatorial 5' UTR sequences were made (FIG. 15A). With the three 5' UTR sequence leads as building blocks, six combinatorial 5' UTR sequences (CoNuUTRs) were constructed by joining two of the NuUTRs with a 6-nt linker (CAACAA). These were labeled as (with the underlined sequences corresponding to the UTR sequences being combined):

CoNuUTR2-3 (NuUTR2-NuUTR3);
(SEQ ID NO: 8))
CACTCGCGCTGCCATCACTCTTCCGCCGTCTTCGCCGCCATCCTCGGCGC

GACTCGCTTCTTTCGGTTCTACCAGGTAGAGTCCGCCGCCATCCTCCACC

CAACAACTTGTCTCGCTCCGGGGAACGCTCGGAAACTCCCGGCCGCCGCC

ACCCGCGTCTGTTCTGTTACACAAGGGAAGAAAAGCCGCTGCCGCACTCC

GAGTGT;

CoNuUTR1-3 (NuUTR1-NuUTR3);
(SEQ ID NO: 9))
CATTCTGTGGTCTGATCATCCTGTGGTTTCGTCGCCGCCATCCTCGTCGC

GACACGCTGTTTTCGGTTCTCGGCCCGACGAGCCATCGCCATCCTACAGC

CAACAACTTGTCTCGCTCCGGGGAACGCTCGGAAACTCCCGGCCGCCGCC

ACCCGCGTCTGTTCTGTTACACAAGGGAAGAAAAGCCGCTGCCGCACTCC

GAGTGT;

CoNuUTR3-2 (NuUTR3-NuUTR2);
(SEQ ID NO: 10))
CTTGTCTCGCTCCGGGGAACGCTCGGAAACTCCCGGCCGCCGCCACCCGC

GTCTGTTCTGTTACACAAGGGAAGAAAAGCCGCTGCCGCACTCCGAGTGT

CAACAACACTCGCGCTGCCATCACTCTTCCGCCGTCTTCGCCGCCATCCT

CGGCGCGACTCGCTTCTTTCGGTTCTACCAGGTAGAGTCCGCCGCCATCC

TCCACC;

CoNuUTR 1-2 (NuUTR1-NuUTR2);
(SEQ ID NO: 11))
CATTCTGTGGTCTGATCATCCTGTGGTTTCGTCGCCGCCATCCTCGTCGC

GACACGCTGTTTTCGGTTCTCGGCCCGACGAGCCATCGCCATCCTACAGC

-continued

CAACAACACTCGCGCTGCCATCACTCTTCCGCCGTCTTCGCCGCCATCCT

CGGCGCGACTCGCTTCTTTCGGTTCTACCAGGTAGAGTCCGCCGCCATCC

TCCACC;

CoNuUTR3-1 (NuUTR3-CNuUTR1);
(SEQ ID NO: 12))
CTTGTCTCGCTCCGGGGAACGCTCGGAAACTCCCGGCCGCCGCCACCCGC

GTCTGTTCTGTTACACAAGGGAAGAAAAGCCGCTGCCGCACTCCGAGTGT

CAACAACATTCTGTGGTCTGATCATCCTGTGGTTTCGTCGCCGCCATCCT

CGTCGCGACACGCTGTTTTCGGTTCTCGGCCCGACGAGCCATCGCCATCC

TACAGC;
and

CoNuUTR2-1 (NuUTR2-NuUTR1);
(SEQ ID NO: 13))
CACTCGCGCTGCCATCACTCTTCCGCCGTCTTCGCCGCCATCCTCGGCGC

GACTCGCTTCTTTCGGTTCTACCAGGTAGAGTCCGCCGCCATCCTCCACC

CAACAACATTCTGTGGTCTGATCATCCTGTGGTTTCGTCGCCGCCATCCT

CGTCGCGACACGCTGTTTTCGGTTCTCGGCCCGACGAGCCATCGCCATCC

TACAGC.

Figure 15B:
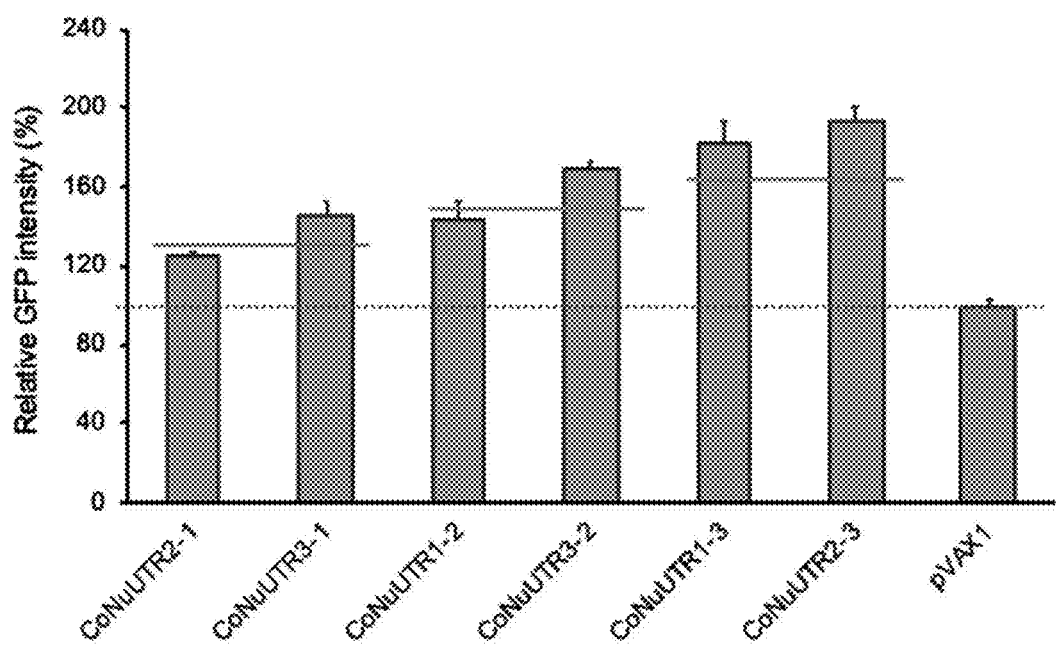

Each of the combinatorial 5' UTR sequences were inserted into the pVAX1-GFP plasmid, co-transfected HEK-293T cells with the resulting plasmids and the BFP expression plasmid. GFP and BFP fluorescence was then measured (FIG. 15B). It was observed that the strength of the 5' UTR sequence combinations positively correlated to the strengths of the two individual 5' UTR sequences: the mean of CoNuUTR1-2 and CoNuUTR2-1<the mean of CoNuUTR1-3, and CoNuUTR3-1<the mean of CoNuUTR2-3 and CoNuUTR3-2. It was also observed that for the CoNuUTRs constructed with the same two NuUTRs, the strength was higher if the stronger NuUTR was placed at the 3' end: CoNuUTR1-2>CoNuUTR2-1, CoNuUTR1-3>CoNuUTR3-1, CoNuUTR2-3>CoNuUTR3-2. It is possible that the sequences close to the coding region have more impact than those located at a distance from the coding region because the former have more chance to interact with the coding region and form secondary structures to modulate the translation. This echoes previous studies on 5' UTR engineering, which also inserted the 5' UTR sequences immediately upstream of the coding region (23, 24).

Figure 15C:
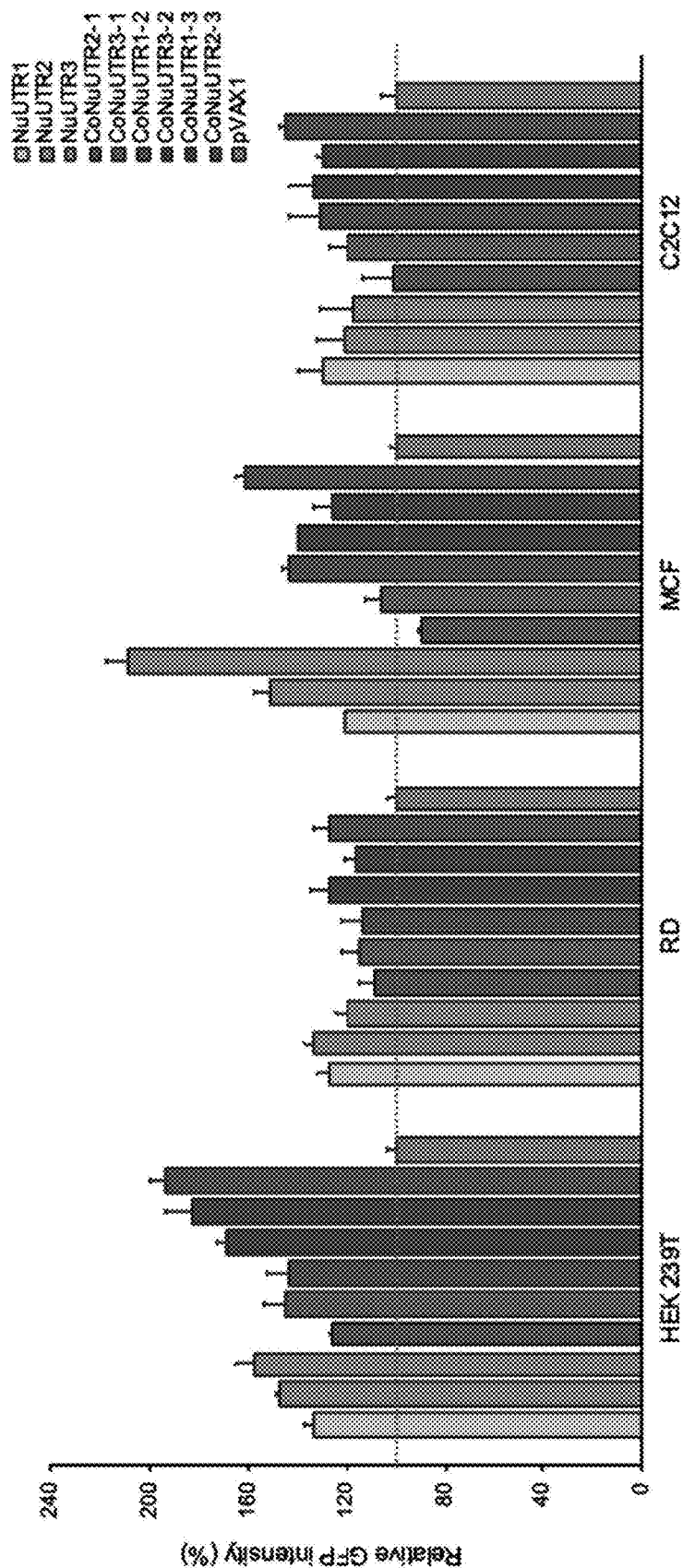
Figure 16A:
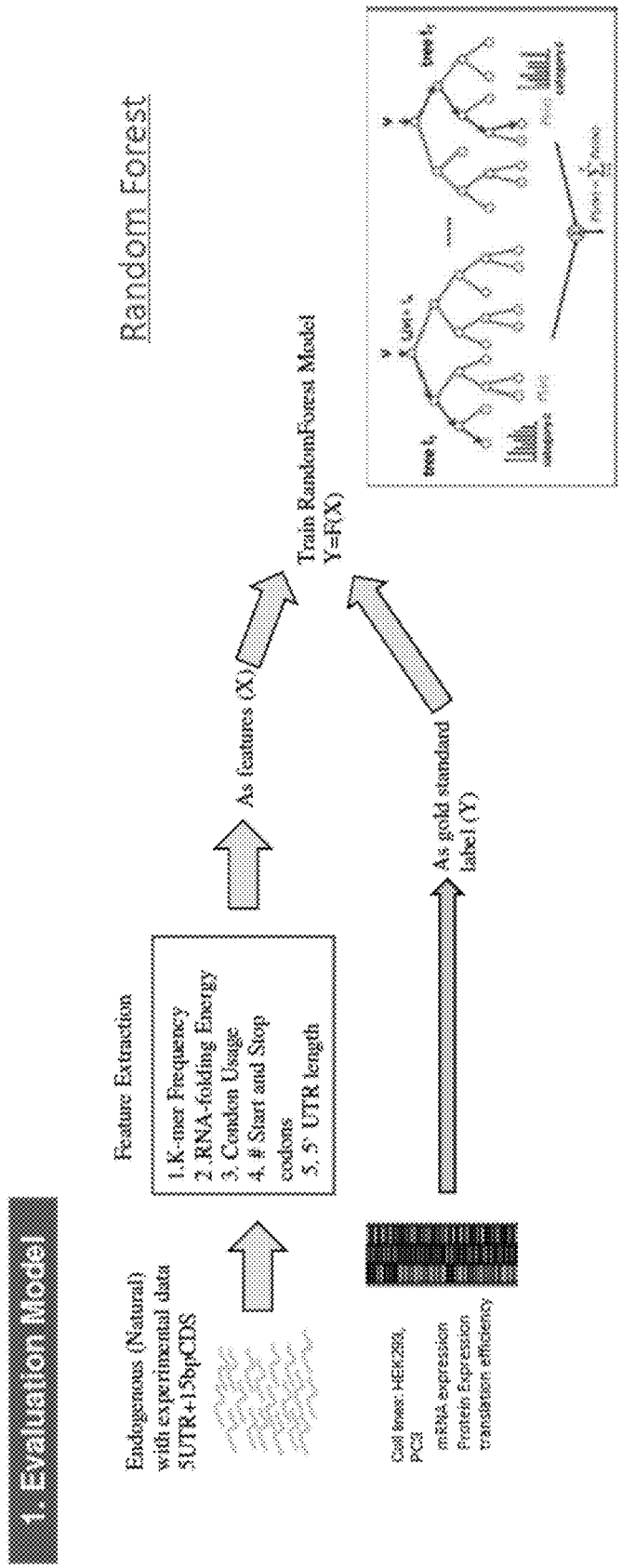
Figure 16B:
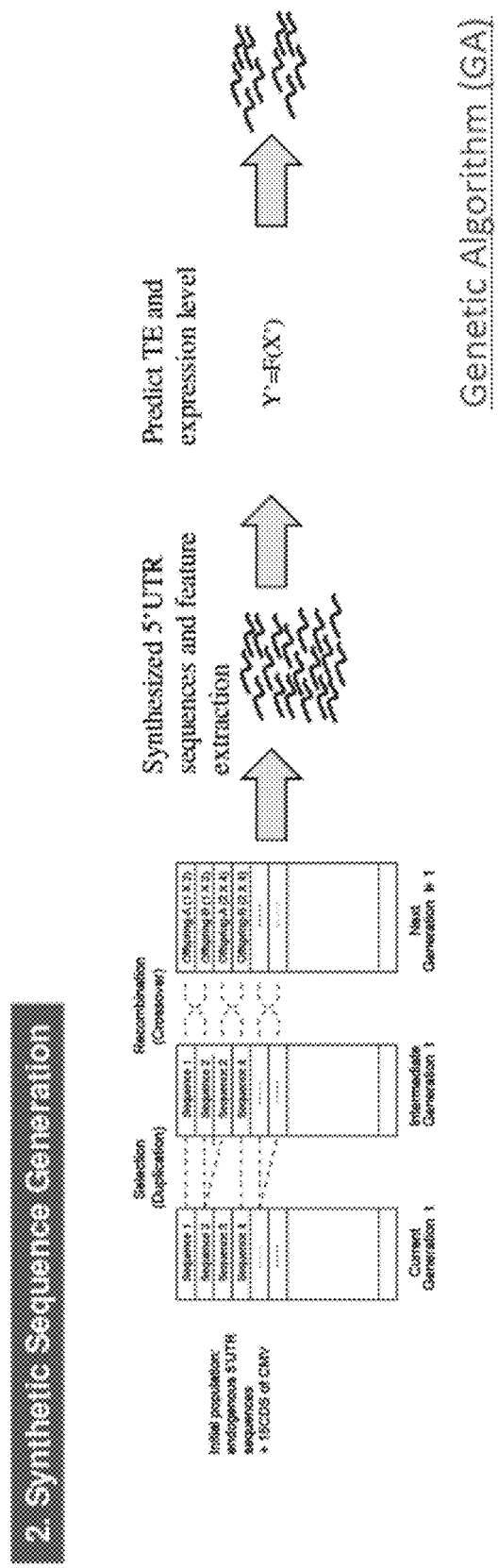
FIG. 16B. Synthetic sequence generation.

How the artificial 5' UTR sequences modulate gene expression in different cell types was next tested. In addition to RD cells, the human breast cancer cell line MCF-7 and the mouse muscle cell line C2C12 were chosen. All three of the 100-bp artificial 5' UTR sequences enhanced protein expression in the four cell types, but the relative strengths of the 5' UTR sequences were different in different cell types (FIG. 15C). Thus, although the strength of the 5' UTR sequences is cell type-dependent to some extent, the 5' UTR combination together with the CMV promoter has great potential, for a variety of cell types, for the expression of genes encoded by non-viral DNA vectors. In addition, it was observed that most of the plasmids with the engineered 5' UTR sequence combinations outperformed the commercial protein expression plasmid. The strengths of the UTR sequences were different in different cell lines, which indicates that the effect of the 5' UTR sequence is partially dependent on cell type. Therefore, the 5' UTR sequences and their combinatorial counterparts identified in this study can enhance protein expression across a variety of mammalian cell types.

REFERENCES

1. Overington, J. P., Al-Lazikani, B. & Hopkins, A. L. How many drug targets are there? Nat. Rev. Drug Discov. (2006). doi:10.1038/nrd2199
2. Imming, P., Sinning, C. & Meyer, A. Drugs, their targets and the nature and number of drug targets. Nat. Rev. Drug Discov. (2006). doi:10.1038/nrd2132
3. Hopkins, A. L. & Groom, C. R. The druggable genome. Nat. Rev. Drug Discov. (2002). doi:10.1038/nrd892
4. Ramamoorth, M. & Narvekar, A. Non viral vectors in gene therapy—An overview. Journal of Clinical and Diagnostic Research (2015). doi:10.7860/JCDR/2015/10443.5394
5. Yin, H. et al. Non-viral vectors for gene-based therapy. Nature Reviews Genetics (2014). doi:10.1038/nrg3763
6. Hardee, C. L., Arévalo-Soliz, L. M., Hornstein, B. D. & Zechiedrich, L. Advances in non-viral DNA vectors for gene therapy. Genes (2017). doi:10.3390/genes8020065
7. Hacein-Bey-Abina, S., Fischer, A. & Cavazzana-Calvo, M. Gene therapy of X-linked severe combined immunodeficiency. Int. J. Hematol. (2002). doi:10.1007/BF02982686
8. Hacein-Bey-Abina, S. et al. A Serious Adverse Event after Successful Gene Therapy for X-Linked Severe Combined Immunodeficiency. N. Engl. J. Med. (2003). doi:10.1056/NEJM200301163480314
9. Escors, D. & Breckpot, K. Lentiviral vectors in gene therapy: Their current status and future potential. Archivum Immunologiae et Therapiae Experimentalis (2010). doi:10.1007/s00005-010-0063-4
10. Schmeer, M., Buchholz, T. & Schleef, M. Plasmid DNA Manufacturing for Indirect and Direct Clinical Applications. Hum. Gene Ther. (2017). doi:10.1089/hum.2017.159
11. Rodrigues, G. A. et al. Pharmaceutical Development of AAV-Based Gene Therapy Products for the Eye. Pharmaceutical Research (2019). doi:10.1007/s11095-018-2554-7
12. Jones, C. H., Hill, A., Chen, M. & Pfeifer, B. A. Contemporary Approaches for Nonviral Gene Therapy. Discov. Med. (2015).
13. Shim, G. et al. Nonviral Delivery Systems For Cancer Gene Therapy: Strategies And Challenges. Curr. Gene Ther. (2018). doi:10.2174/1566523218666180119121949
14. Bai, H., Lester, G. M. S., Petishnok, L. C. & Dean, D. A. Cytoplasmic transport and nuclear import of plasmid DNA. Biosci. Rep. (2017). doi:10.1042/bsr20160616
15. Dronadula, N. et al. Construction of a novel expression cassette for increasing transgene expression in vivo in endothelial cells of large blood vessels. Gene Ther. (2011). doi:10.1038/gt.2010.173
16. Powell, S. K., Rivera-Soto, R. & Gray, S. J. Viral expression cassette elements to enhance transgene target specificity and expression in gene therapy. Discov. Med. (2015). doi:10.1530/ERC-14-0411.Persistent
17. Garmory, H. S., Brown, K. A. & Titball, R. W. DNA vaccines: Improving expression of antigens. Genetic Vaccines and Therapy (2003). doi:10.1186/1479-0556-1-2
18. Babendure, J. R., Babendure, J. L., Ding, J. H. & Tsien, R. Y. Control of mammalian translation by mRNA structure near caps. RNA (2006). doi:10.1261/rna.2309906

19. Sudrik, C., Arha, M., Cao, J., Schaffer, D. V. & Kane, R. S. Translational repression using BIV Tat peptide-TAR RNA interaction in mammalian cells. Chem. Commun. (2013). doi:10.1039/c3cc43086c
20. Asrani, K. H. et al. Optimization of mRNA untranslated regions for improved expression of therapeutic mRNA. RNA Biol. (2018). doi:10.1080/15476286.2018.1450054
21. Weinberger, A. et al. Deciphering the rules by which 5'-UTR sequences affect protein expression in yeast. Proc. Natl. Acad. Sci. (2013). doi:10.1073/pnas.1222534110
22. Decoene, T., Peters, G., De Maeseneire, S. L. & De Mey, M. Toward Predictable 5'UTRs in *Saccharomyces cerevisiae*: Development of a yUTR Calculator. ACS Synth. Biol. (2018). doi:10.1021/acssynbio.7b00366
23. Ding, W. et al. Engineering the 5' UTR-Mediated Regulation of Protein Abundance in Yeast Using Nucleotide Sequence Activity Relationships. ACS Synth. Biol. (2018). doi:10.1021/acssynbio.8b00127
24. Sample, P. J. et al. Human 5' UTR design and variant effect prediction from a massively parallel translation assay. bioRxiv (2018). doi:10.1101/310375
25. Kozak, M. Downstream secondary structure facilitates recognition of initiator codons by eukaryotic ribosomes. Proc. Natl. Acad. Sci. (2006). doi:10.1073/pnas.87.21.8301
26. Kozak, M. An analysis of 5'-noncoding sequences from 699 vertebrate messenger rNAS. Nucleic Acids Res. (1987). doi:10.1093/nar/15.20.8125
27. Andreev, D. E. et al. Translation of 5' leaders is pervasive in genes resistant to eIF2 repression. Elife (2015). doi: 10.7554/eLife.03971
28. Hsieh, A. C. et al. The translational landscape of mTOR signalling steers cancer initiation and metastasis. Nature (2012). doi:10.1038/nature10912
29. Wein, N. et al. Translation from a DMD exon 5 IRES results in a functional dystrophin isoform that attenuates dystrophinopathy in humans and mice. Nat. Med. (2014). doi:10.1038/nm.3628
30. Hanson, S., Berthelot, K., Fink, B., McCarthy, J. E. G. & Suess, B. Tetracycline-aptamer-mediated translational regulation in yeast. Mol. Microbiol. (2003). doi:10.1046/j.1365-2958.2003.03656.x
31. Ho, T. K. The random subspace method for constructing decision forests. IEEE Trans. Pattern Anal. Mach. Intell. (1998). doi:10.1109/34.709601
32. Scrucca, L. GA: A Package for Genetic Algorithms in R. J. Stat. Softw. (2015). doi:10.18637/jss.v053.i04
33. Wong, A. S. L., Choi, G. C. G., Cheng, A. A., Purcell, O. & Lu, T. K. Massively parallel high-order combinatorial genetics in human cells. Nat. Biotechnol. (2015). doi:10.1038/nbt.3326
34. Chang, K., Elledge, S. J. & Hannon, G. J. Lessons from Nature: microRNA-based shRNA libraries. Nat. Methods (2006). doi:10.1038/nmeth923
35. Shalem, O. et al. Genome-scale CRISPR-Cas9 knockout screening in human cells. Science (80-.). (2014). doi: 10.1126/science.1247005
36. Akhtar, W. et al. Chromatin position effects assayed by thousands of reporters integrated in parallel. Cell (2013). doi:10.1016/j.cell.2013.07.018
37. Wilson, C. Position Effects On Eukaryotic Gene Expression. Annu. Rev. Cell Dev. Biol. (2002). doi:10.1146/annurev.cellbio.6.1.679
38. Roquet, N., Soleimany, A. P., Ferris, A. C., Aaronson, S. & Lu, T. K. Synthetic recombinase-based State machines in living cells. Science (80-.). (2016). doi:10.1126/science.aad8559
39. Guye, P., Li, Y., Wroblewska, L., Duportet, X. & Weiss, R. Rapid, modular and reliable construction of complex mammalian gene circuits. Nucleic Acids Res. (2013). doi:10.1093/nar/gkt605
40. Perez-Pinera, P. et al. Synthetic biology and microbioreactor platforms for programmable production of biologics at the point-of-care. Nat. Commun. (2016). doi:10.1038/ncomms12211
41. Brown, W. R. A., Lee, N. C. O., Xu, Z. & Smith, M. C. M. Serine recombinases as tools for genome engineering. Methods (2011). doi:10.1016/j.ymeth.2010.12.031
42. Muthumani, K. et al. Optimized and enhanced DNA plasmid vector based in vivo construction of a neutralizing anti-HIV-1 envelope glycoprotein Fab. Hum. Vaccines Immunother. (2013). doi:10.4161/hv.26498
43. Blundell, T. L. et al. Structural biology and bioinformatics in drug design: opportunities and challenges for target identification and lead discovery. Philos T R Soc B 361, 413-423, doi:10.1098/rstb.2005.1800 (2006).
44. Hoelder, S., Clarke, P. A. & Workman, P. Discovery of small molecule cancer drugs: Successes, challenges and opportunities. Mol Oncol 6, 155-176, doi:10.1016/j.molonc.2012.02.004 (2012).
45. Scott, D. E., Bayly, A. R., Abell, C. & Skidmore, J. Small molecules, big targets: drug discovery faces the protein-protein interaction challenge. Nat Rev Drug Discov 15, 533-550, doi:10.1038/nrd.2016.29 (2016).
46. Verdine, G. L. & Hilinski, G. J. Stapled Peptides for Intracellular Drug Targets. Method Enzymol 503, 3-33, doi:10.1016/B978-0-12-396962-0.00001-X (2012).
47. Leader, B., Baca, Q. J. & Golan, D. E. Protein therapeutics: A summary and pharmacological classification. Nature Reviews Drug Discovery 7, 21-39, doi:10.1038/nrd2399 (2008).
48. Reichert, J. M., Rosensweig, C. J., Faden, L. B. & Dewitz, M. C. Monoclonal antibody successes in the clinic. Nat Biotechnol 23, 1073-1078, doi:DOI 10.1038/nbt0905-1073 (2005).
49. Naldini, L. Gene therapy returns to centre stage. Nature 526, 351-360, doi:10.1038/nature15818 (2015).
50. Sahin, U., Kariko, K. & Tureci, O. mRNA-based therapeutics—developing a new class of drugs. Nature Reviews Drug Discovery 13, 759-780, doi:10.1038/nrd4278 (2014).
51. Ferraro, B. et al. Clinical Applications of DNA Vaccines: Current Progress. Clin Infect Dis 53, 296-302, doi: 10.1093/cid/cir334 (2011).
52. Kutzler, M. A. & Weiner, D. B. DNA vaccines: ready for prime time? Nat Rev Genet 9, 776-788, doi:10.1038/nrg2432 (2008).
53. Lu, Q. L., Bou-Gharios, G. & Partridge, T. A. Non-viral gene delivery in skeletal muscle: a protein factory. Gene Ther 10, 131-142, doi:10.1038/sj.gt.3301874 (2003).
54. Qin, J. Y. et al. Systematic Comparison of Constitutive Promoters and the Doxycycline-Inducible Promoter. Plos One 5, doi:ARTN e1061110.1371/journal.pone.0010611 (2010).
55. Ho, T. K. The random subspace method for constructing decision forests. Ieee T Pattern Anal 20, 832-844 (1998).

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

What is claimed is:

1. A polynucleotide comprising a synthetic 5' untranslated region (5' UTR) comprising the sequence of:

(SEQ ID NO: 1)
CACTCGCGCTGCCATCACTCTTCCGCCGTCTTCGCCGCCATCCTCGGCG

CGACTCGCTTCTTTCGGTTCTACCAGGTAGAGTCCGCCGCCATCCTCCA

CC;

(SEQ ID NO: 2)
CATTCTGTGGTCTGATCATCCTGTGGTTTCGTCGCCGCCATCCTCGTCG

CGACACGCTGTTTTCGGTTCTCGGCCCGACGAGCCATCGCCATCCTACA

GC;
or (SEQ ID NO: 3)
CTTGTCTCGCTCCGGGGAACGCTCGGAAACTCCCGGCCGCCGCCACCCG

CGTCTGTTCTGTTACACAAGGGAAGAAAAGCCGCTGCCGCACTCCGAGT

GT.

2. The polynucleotide of claim 1, wherein the polynucleotide further comprises:
a linker sequence;
a promoter;
a sequence encoding a polypeptide; or
a combination thereof.

3. The polynucleotide of claim 2, wherein the polynucleotide comprises the sequence of:

(SEQ ID NO: 8)
CACTCGCGCTGCCATCACTCTTCCGCCGTCTTCGCCGCCATCCTCGGCG

GACTCGCTTCTTTCGGTTCTACCAGGTAGAGTCCGCCGCCATCCTCCACC

CAACAACTTGTCTCGCTCCGGGGAACGCTCGGAAACTCCCGGCCGCCGCC

ACCCGCGTCTGTTCTGTTACACAAGGGAAGAAAAGCCGCTGCCGCACTCC

GAGTGT;

(SEQ ID NO: 9)
CATTCTGTGGTCTGATCATCCTGTGGTTTCGTCGCCGCCATCCTCGTCGC

GACACGCTGTTTTCGGTTCTCGGCCCGACGAGCCATCGCCATCCTACAGC

CAACAACTTGTCTCGCTCCGGGGAACGCTCGGAAACTCCCGGCCGCCGCC

ACCCGCGTCTGTTCTGTTACACAAGGGAAGAAAAGCCGCTGCCGCACTCC

GAGTGT;

(SEQ ID NO: 10)
CTTGTCTCGCTCCGGGGAACGCTCGGAAACTCCCGGCCGCCGCCACCCGC

GTCTGTTCTGTTACACAAGGGAAGAAAAGCCGCTGCCGCACTCCGAGTGT

```
                                                   (SEQ ID NO: 10)
CAACAACACTCGCGCTGCCATCACTCTTCCGCCGTCTTCGCCGCCATCCT

CGGCGCGACTCGCTTCTTTCGGTTCTACCAGGTAGAGTCCGCCGCCATCC

TCCACC;
                                                   (SEQ ID NO: 11)
CATTCTGTGGTCTGATCATCCTGTGGTTTCGTCGCCGCCATCCTCGTCGC

GACACGCTGTTTTCGGTTCTCGGCCCGACGAGCCATCGCCATCCTACAGC

CAACAACACTCGCGCTGCCATCACTCTTCCGCCGTCTTCGCCGCCATCCT

CGGCGCGACTCGCTTCTTTCGGTTCTACCAGGTAGAGTCCGCCGCCATCC

TCCACC;
                                                   (SEQ ID NO: 12)
CTTGTCTCGCTCCGGGGAACGCTCGGAAACTCCCGGCCGCCGCCACCCGC

GTCTGTTCTGTTACACAAGGGAAGAAAAGCCGCTGCCGCACTCCGAGTGT

CAACAACATTCTGTGGTCTGATCATCCTGTGGTTTCGTCGCCGCCATCCT

CGTCGCGACACGCTGTTTTCGGTTCTCGGCCCGACGAGCCATCGCCATCC

TACAGC;
or
                                                   (SEQ ID NO: 13)
CACTCGCGCTGCCATCACTCTTCCGCCGTCTTCGCCGCCATCCTCGGCGC

GACTCGCTTCTTTCGGTTCTACCAGGTAGAGTCCGCCGCCATCCTCCACC

CAACAACATTCTGTGGTCTGATCATCCTGTGGTTTCGTCGCCGCCATCCT

CGTCGCGACACGCTGTTTTCGGTTCTCGGCCCGACGAGCCATCGCCATCC

TACAGC.
```

4. A composition comprising a plurality of polynucleotides according to claim 3.

5. A composition comprising a plurality of polynucleotides according to claim 2.

6. The polynucleotide of claim 1, wherein the polynucleotide further comprises a promoter.

7. The polynucleotide of claim 6, wherein the promoter is positioned 5' to the 5' UTR sequence.

8. The polynucleotide of claim 6, wherein the polynucleotide comprises the sequence of:

```
                                                    (SEQ ID NO: 8)
CACTCGCGCTGCCATCACTCTTCCGCCGTCTTCGCCGCCATCCTCGGCGC

GACTCGCTTCTTTCGGTTCTACCAGGTAGAGTCCGCCGCCATCCTCCACC

CAACAACTTGTCTCGCTCCGGGGAACGCTCGGAAACTCCCGGCCGCCGCC

ACCCGCGTCTGTTCTGTTACACAAGGGAAGAAAAGCCGCTGCCGCACTCC

GAGTGT;
                                                    (SEQ ID NO: 9)
CATTCTGTGGTCTGATCATCCTGTGGTTTCGTCGCCGCCATCCTCGTCGC

GACACGCTGTTTTCGGTTCTCGGCCCGACGAGCCATCGCCATCCTACAGC

CAACAACTTGTCTCGCTCCGGGGAACGCTCGGAAACTCCCGGCCGCCGCC

ACCCGCGTCTGTTCTGTTACACAAGGGAAGAAAAGCCGCTGCCGCACTCC

GAGTGT;
                                                    (SEQ ID NO: 10)
CTTGTCTCGCTCCGGGGAACGCTCGGAAACTCCCGGCCGCCGCCACCCGC

GTCTGTTCTGTTACACAAGGGAAGAAAAGCCGCTGCCGCACTCCGAGTGT

CAACAACACTCGCGCTGCCATCACTCTTCCGCCGTCTTCGCCGCCATCCT

CGGCGCGACTCGCTTCTTTCGGTTCTACCAGGTAGAGTCCGCCGCCATCC

TCCACC;
                                                    (SEQ ID NO: 11)
CATTCTGTGGTCTGATCATCCTGTGGTTTCGTCGCCGCCATCCTCGTCGC

GACACGCTGTTTTCGGTTCTCGGCCCGACGAGCCATCGCCATCCTACAGC

CAACAACACTCGCGCTGCCATCACTCTTCCGCCGTCTTCGCCGCCATCCT

CGGCGCGACTCGCTTCTTTCGGTTCTACCAGGTAGAGTCCGCCGCCATCC

TCCACC;
                                                    (SEQ ID NO: 12)
CTTGTCTCGCTCCGGGGAACGCTCGGAAACTCCCGGCCGCCGCCACCCGC

GTCTGTTCTGTTACACAAGGGAAGAAAAGCCGCTGCCGCACTCCGAGTGT

CAACAACATTCTGTGGTCTGATCATCCTGTGGTTTCGTCGCCGCCATCCT

CGTCGCGACACGCTGTTTTCGGTTCTCGGCCCGACGAGCCATCGCCATCC

TACAGC;
or
                                                    (SEQ ID NO: 13)
CACTCGCGCTGCCATCACTCTTCCGCCGTCTTCGCCGCCATCCTCGGCGC

GACTCGCTTCTTTCGGTTCTACCAGGTAGAGTCCGCCGCCATCCTCCACC

CAACAACATTCTGTGGTCTGATCATCCTGTGGTTTCGTCGCCGCCATCCT

CGTCGCGACACGCTGTTTTCGGTTCTCGGCCCGACGAGCCATCGCCATCC

TACAGC.
```

9. The polynucleotide of claim 1, wherein the polynucleotide further comprises a sequence encoding a polypeptide.

10. The polynucleotide of claim 9, wherein the 5' UTR sequence is operably liked to the sequence encoding the polypeptide.

11. The polynucleotide of claim 1, wherein the polynucleotide further comprises a promoter and a sequence encoding a polypeptide, wherein the promoter is positioned 5' to the 5' UTR sequence, and wherein the 5' UTR sequence is operably liked to the sequence encoding the polypeptide.

12. The polynucleotide of claim 11, wherein the polynucleotide comprises the sequence of:

```
                                                    (SEQ ID NO: 8)
CACTCGCGCTGCCATCACTCTTCCGCCGTCTTCGCCGCCATCCTCGGCGC

GACTCGCTTCTTTCGGTTCTACCAGGTAGAGTCCGCCGCCATCCTCCACC

CAACAACTTGTCTCGCTCCGGGGAACGCTCGGAAACTCCCGGCCGCCGCC

ACCCGCGTCTGTTCTGTTACACAAGGGAAGAAAAGCCGCTGCCGCACTCC

GAGTGT;
                                                    (SEQ ID NO: 9)
CATTCTGTGGTCTGATCATCCTGTGGTTTCGTCGCCGCCATCCTCGTCGC

GACACGCTGTTTTCGGTTCTCGGCCCGACGAGCCATCGCCATCCTACAGC

CAACAACTTGTCTCGCTCCGGGGAACGCTCGGAAACTCCCGGCCGCCGCC
```

ACCCGCGTCTGTTCTGTTACACAAGGGAAGAAAAGCCGCTGCCGCACTCC

GAGTGT;

(SEQ ID NO: 10)
CTTGTCTCGCTCCGGGGAACGCTCGGAAACTCCCGGCCGCCGCCACCCGC

GTCTGTTCTGTTACACAAGGGAAGAAAAGCCGCTGCCGCACTCCGAGTGT

CAACAACACTCGCGCTGCCATCACTCTTCCGCCGTCTTCGCCGCCATCCT

CGGCGCGACTCGCTTCTTTCGGTTCTACCAGGTAGAGTCCGCCGCCATCC

TCCACC;

(SEQ ID NO: 11)
CATTCTGTGGTCTGATCATCCTGTGGTTTCGTCGCCGCCATCCTCGTCGC

GACACGCTGTTTTCGGTTCTCGGCCCGACGAGCCATCGCCATCCTACAGC

CAACAACACTCGCGCTGCCATCACTCTTCCGCCGTCTTCGCCGCCATCCT

CGGCGCGACTCGCTTCTTTCGGTTCTACCAGGTAGAGTCCGCCGCCATCC

TCCACC;

(SEQ ID NO: 12)
CTTGTCTCGCTCCGGGGAACGCTCGGAAACTCCCGGCCGCCGCCACCCGC

GTCTGTTCTGTTACACAAGGGAAGAAAAGCCGCTGCCGCACTCCGAGTGT

CAACAACATTCTGTGGTCTGATCATCCTGTGGTTTCGTCGCCGCCATCCT

CGTCGCGACACGCTGTTTTCGGTTCTCGGCCCGACGAGCCATCGCCATCC

TACAGC;
or (SEQ ID NO: 13)
CACTCGCGCTGCCATCACTCTTCCGCCGTCTTCGCCGCCATCCTCGGCGC

GACTCGCTTCTTTCGGTTCTACCAGGTAGAGTCCGCCGCCATCCTCCACC

CAACAACATTCTGTGGTCTGATCATCCTGTGGTTTCGTCGCCGCCATCCT

CGTCGCGACACGCTGTTTTCGGTTCTCGGCCCGACGAGCCATCGCCATCC

TACAGC.

13. A polynucleotide comprising a synthetic 5' untranslated region (5' UTR) that is operably linked to a sequence encoding a polypeptide, wherein the 5' UTR comprises the sequence of any one of SEQ ID NOs: 1-3 or a sequence having 1-10 mutations relative to any one of SEQ ID NOs: 1-3.

14. A composition comprising a plurality of polynucleotides according to claim 13.

* * * * *

UNITED STATES PATENT AND TRADEMARK OFFICE
CERTIFICATE OF CORRECTION

PATENT NO. : 11,875,876 B2
APPLICATION NO. : 16/441647
DATED : January 16, 2024
INVENTOR(S) : Timothy Kuan-Ta Lu et al.

It is certified that error appears in the above-identified patent and that said Letters Patent is hereby corrected as shown below:

In the Claims

At Column 47, Claim 5, Lines 39-40:
"...polynucleotides according to claim 2."
Should read:
--...polynucleotides according to claim 1.--

Signed and Sealed this
Second Day of July, 2024

Katherine Kelly Vidal
*Director of the United States Patent and Trademark Office*